(12) United States Patent
Cai et al.

(10) Patent No.: US 6,462,041 B1
(45) Date of Patent: Oct. 8, 2002

(54) GAMBOGIC ACID, ANALOGS AND DERIVATIVES AS ACTIVATORS OF CASPASES AND INDUCERS OF APOPTOSIS

(75) Inventors: Sui Xiong Cai; Han-Zhong Zhang; Yan Wang; Ben Tseng; Shailaja Kasibhatla, all of San Diego; John A. Drewe, Costa Mesa, all of CA (US)

(73) Assignee: Cytovia, Inc., San Diego, CA (US)

( * ) Notice: Subject to any disclaimer, the term of this patent is extended or adjusted under 35 U.S.C. 154(b) by 0 days.

(21) Appl. No.: 09/495,120

(22) Filed: Feb. 1, 2000

Related U.S. Application Data

(60) Provisional application No. 60/135,424, filed on May 21, 1999.

(51) Int. Cl.[7] ...................... A61K 31/45; A61K 31/497; C07D 241/02; C07D 311/78
(52) U.S. Cl. ................. 514/232.5; 514/252.11; 514/316; 514/321; 514/393; 544/109; 544/357; 544/378; 546/187; 546/190; 546/197; 548/303.1; 548/526; 549/260
(58) Field of Search ............... 514/450, 232.5, 514/252.11, 252.13, 316, 321, 338, 393; 544/109, 357, 378; 546/187, 189, 190, 197; 548/303.1, 526; 549/260

(56) References Cited

U.S. PATENT DOCUMENTS 6,284,783 B1    9/2001  Zhou et al.  .................. 514/414

FOREIGN PATENT DOCUMENTS

WO    WO 96/20721    7/1996

OTHER PUBLICATIONS

"Colchicine," The Merck Index, Twelfth Edition, Merck & Co., Inc., Whitehouse Station, N.J., entry 2536, pp. 418–419 (1996).

"Gambogic Acid," The Merck Index, Twelfth Edition, Merck & Co., Inc., Whitehouse Station, N.J., entry 4373, p. 739 (1996).

"Topotecan," The Merck Index, Twelfth Edition, Merck & Co., Inc., Whitehouse Station, N.J., entry 9687, p. 1629 (1996).

"ColBenemid® Tablets (Probenecid–Colchicine), U.S.P.," Physicians' Desk Reference, 54th Edition, Medical Economics Company, Inc., Montvale, N.J., pp. 1759–1760 (2000).

"Hycamtin® (hi–kam–tin) brand of topotecan hydrochloride for injection (for intravenous use)," Physicians' Desk Reference, 54th Edition, Medical Economics Company, Inc., Montvale, N.J., pp. 3006–3010 (2000).

Adawadkar, P.D. et al., "Colouring Matters of *Garcinia morella*: Part VIII–Morellinol Dihydromorelloflavone & Morelloflavone–7"–β–glucoside, *Indian J. Chem.* 14B:19–21 (1976).

(List continued on next page.)

*Primary Examiner*—T. A. Solola
(74) *Attorney, Agent, or Firm*—Sterne, Kessler, Goldstein & Fox P.L.L.C.

(57) ABSTRACT

The present invention is directed to gambogic acid, analogs and derivatives thereof, represented by the general Formulae I–III:

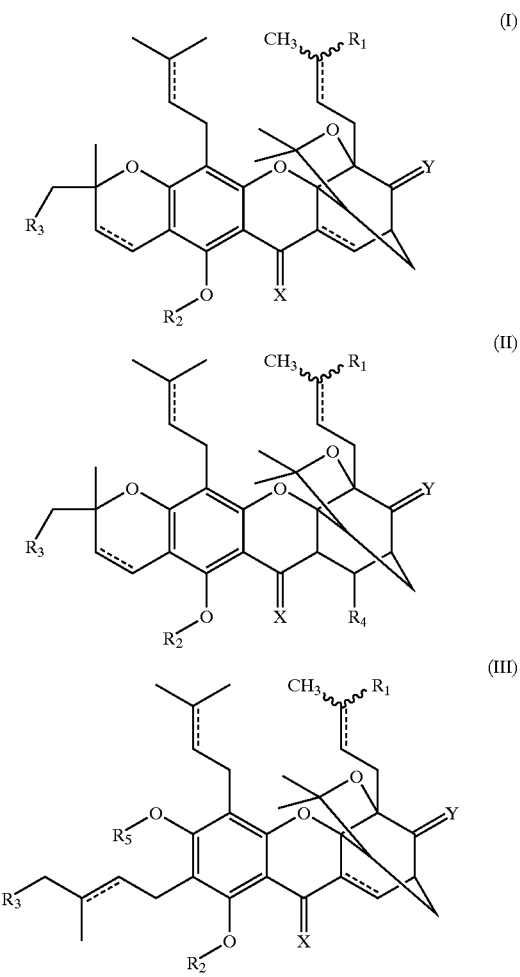

wherein $R_1$–$R_5$ are defined herein. The present invention also relates to the discovery that compounds having Formula I–III are activators of caspases and inducers of apoptosis. Therefore, the activators of caspases and inducers of apoptosis of this invention can be used to induce cell death in a variety of clinical conditions in which uncontrolled cell growth and spread of abnormal cells occurs.

54 Claims, 6 Drawing Sheets

OTHER PUBLICATIONS

Ahmad, S.A. et al., "Gamboge. Part II," *J. Chem. Soc.* C:772–779 (1966).

Asano, J. et al., "Cytotoxic Xanthones from Garcinia Hanburyi," *Phytochem.* 41:815–820 (1996).

Batteux, F. et al., "Gene Therapy of Experimental Autoimmune Thyroiditis by In Vivo Administration of Plasmid DNA Coding for Fas Ligand," *J. Immunol.* 162 :603–608 (Jan. 1999).

Bhat, H.B. et al., "The Colouring Matters of *Garcinia morella*: Part V–Isolation of Desoxymorellin & Dihydroisomorellin," *Indian J. Chem.* 2:405–410 (1964).

Boirivant, M. et al., "Laima Propria T Cells in Crohn's Disease and Other Gastrointestinal Inflammation Show Defective CD2 Pathway–Induced Apoptosis," *Gastroenterol.* 116 :557–565 (Mar. 1999).

Calabresi, P and B.A. Chabner, "Chemotherapy of Neoplastic Diseases," Section X in *Goodman & Gilman's The Pharmacological Basis of Therapeutics, $9^{th}$ Ed.*, The McGraw–Hill Companies, 1996, pp. 1225–1287 (1996).

Cao, S–G. et al., "Novel Cytotoxic Polyprenylated Xanthonoids from *Garcinia gaudichaudii* (Guttiferae)," *Tetrahedron* 54:10915–10924 (1998).

Cao, S–G. et al., "Cytotoxic Caged Tetraprenylated Xanthonoids from *Garcinia gaudichaudii* (Guttiferae)," *Tetrahedron Lett.* 390:3353–3356 (1998).

Coven, T.R. et al., "PUVA–induced lymphocyte apoptosis: Mechanism of action in psoriasis," *Photodermatol. Phytoimmunol. Photomed.* 15 :22–27 (Feb. 1999).

Ellis, R.E. and H.R. Horovitz, "Two C. elegans genes control the programmed deaths of specific cells in the pharnyx," *Development* 112:591–603 (1991).

Ellis, R.E. et al., "Mechanisms and Functions of Cell Death," *Annu. Rev. Cell. Biol.* 7:663–698 (1991).

Friesen, C. et al., "Involvement of the CD95 (APO–1/Fas) receptor/ligand system in drug–induced apoptosis in leukemia cells," *Nature Med.* 2:574–577 (1996).

Glücksmann, A., "Cell Deaths in Normal Vertebrate Ontogeny,"in *Biological Reviews of the Cambridge Philosophical Society*, H.M. Fox, ed., University Press, 1951, pp. 59–86.

Glücksmann, A., "Cell death in normal development,"0 *Arch. Bio.* 76:419–437 (1965).

Heenen, M. et al., "Methotrexate induces apoptotic cell death in human keratinocytes," *Arch. Dermatol. Res.* 290:240–245 (1998).

Infante, A.J. et al., "The clinical spectrum in a large kindred with autoimmune lymphoproliferative syndrome caused by a Fas mutation the impairs lymphocyte apoptosis," *J. Pediatrics* 133:629–633 (1998).

Karanjgaonkar, C.G. et al., "Morellic, Isomorellic and Gambogic Acids," *Tetrahedron Lett.* 687–691 (1966).

Leong, Y.–W. et al., "Forbesione, a Modified Xanthone from *Garcinia forbesii*," *J. Chem. Res. S*:392–393 (1996).

Lin, L.–J. et al., "Isogambogic acid and Isomorellinol from *Garcinia hanburyi*," *Magnetic Resonance Chem.* 31340–347 (1993).

Los, M. et al., "Cross–Resistance of CD95– and Drug–Induced Apoptosis as a Consequence of Deficient Activation of Caspases (ICE/Ced–3 Proteases)," *Blood* 90:3118–3129 (1997).

Lu, G.–B. et al., "Isolation and Structure of Neo–Gambogic Acid From Gamboge *Garcinia hanburyi*)," *Acta Pharmaceutica Sinica* 19:636–639 (1984).

Lu, G. et al., "Isolation and structure of neo–gambogic acid from gamboge (*Garcinia hanburyi*)," *Chem Abs.* 102:21181 (1984).

Ohsako, S. and K.B. Elkon,"Apoptosis in the effector phase of autoimmune diabetes, multiple sclerosis and thyroiditis," *Cell Death Differentiation* 6:13–21 (Jan. 1999).

Ollis, W.D. et al., "The Constitution of Gambogic Acid," *Tetrahedron* 21:1453–1470 (1965).

O'Reilly, L.A. and A. Strasser, "Apoptosis and autoimmune disease," *Inflamm. Res.* 48:5–21 (Jan. 1999).

Orrenius, S., "Apoptosis: molecular mechanisms and implications for human disease," *J. Internal Med.* 237:529–536 (1995).

Ozawa, M. et al., "312–nanometer Ultraviolet B Light (Narrow–Band UVB) Induces Apoptosis of T Cells within Psoriatic Lesions," *J. Exp. Med.* 189:711–718 (Feb. 1999).

Rao, G.S.R.S. et al., "Structure of moreollin, a pigment isolated from *Garcinia morella* Desser," *Proc. Indian Acad. Sci.* 87:75–86 (1978).

Savill, J., "Apoptosis in resolution of inflammation," *J. Leukocyte Biol.* 61:375–380 (1997).

Schmitt, E. et al., "The Bcl–xL and Bax–α control points: modulation of apoptosis induced by cancer chemotherapy and relation to TPCK–sensitive protease and caspase activation," *Biochem. Cell Biol.* 75:301–314 (1997).

Thornberry, N.A., "The capase family of cysteine proteases," *Br. Med. Bull.* 53:478–490 (1996).

Thornberry, N.A., "Caspases: key mediators of apoptosis," *Chemistry & Biology* 5:R97–R103 (1998).

Vaishnaw, A.K. et al., "The molecular basis from apoptotic defects in patients with CD95 (Fas/Apo–1) mutations," *J. Clin. Invest.* 103: 355–363 (Feb. 1999).

Vaux, D. et al. ,"An Evolutionary Perspective on Apoptosis," *Cell* 76:777–779 (1994).

Wakisaka, S. et al., "Modulation by proinflammatory cytokines of Fas.Fas ligand–mediated apoptotic cell death of synovial cells in patients with rheumatoid arthritis (RA)," *Clin. Exp. Immunol.* 114:119–128 (1998).

Wylie, A.H., "Cell Death: a new classification separating apoptosis from necrosis," in *Cell death in biology and pathology*, Bowen, I.D. and R.A. Lockshin, eds., Chapman and Hall, 1981, pp. 9–34.

Wylie, A.H. et al., "Cell Death: The Significance of Apoptosis," *Intl. Rev. Cytol.* 68:251–306 (1980).

Yates, P. et al., "Acetyl–α–Gambogic Acid," *Tetrahedron Lett.* 1623–1629 (1963).

Zhou, T. et al., "Bisindolymaleimide VIII facilitates Fas–mediated apoptosis and Inhibits T cell–mediated autoimmune diseases," *Nature Med.* 5:42–48 (Jan. 1999).

International Search Report for International Application PCT/US00/02332, mailed Jun. 27, 2000.

Uncleaved
Cleaved

Uncleaved
Cleaved

GAMBOGIC ACID, ANALOGS AND DERIVATIVES AS ACTIVATORS OF CASPASES AND INDUCERS OF APOPTOSIS

CROSS-REFERENCE TO RELATED APPLICATIONS

This application claims the benefit of U.S. Provisional Application No. 60/135,424, filed May 21, 1999.

BACKGROUND OF THE INVENTION

1. Field of the Invention

This invention is in the field of medicinal chemistry. In particular, the invention relates to gambogic acid, novel analogs of gambogic acid and derivatives of gambogic acid, and the discovery that these compounds are activators of caspases and inducers of apoptosis. The invention also relates to the use of these compounds as therapeutically effective anti-cancer agents.

2. Description of Background Art

Organisms eliminate unwanted cells by a process variously known as regulated cell death, programmed cell death or apoptosis. Such cell death occurs as a normal aspect of animal development as well as in tissue homeostasis and aging (Glucksmann, A., Biol. Rev. Cambridge Philos. Soc. 26:59–86 (1951); Glucksmann, A., Archives de Biologie 76:419–437 (1965); Ellis, et al., Dev. 112:591–603 (1991); Vaux, et al., Cell 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., J. Internal Medicine 237:529–536 (1995)).

Apoptosis is achieved through an endogenous mechanism of cellular suicide (Wyllie, A. H., in Cell Death in Biology and Pathology, Bowen and Lockshin, eds., Chapman and Hall (1981), pp. 9–34). A cell activates its internally encoded suicide program as a result of either internal or external signals. The suicide program is executed through the activation of a carefully regulated genetic program (Wyllie, et al., Int. Rev. Cyt. 68:251 (1980); Ellis, et al., Ann. Rev. Cell Bio. 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., J. Internal Medicine 237:529–536 (1995)).

It has been found that a group of proteases are a key element in apoptosis (see, e.g. Thornberry, Chemistry and Biology 5:R97–R103 (1998); Thornberry, British Med. Bull. 53:478–490 (1996)). Genetic studies in the nematode Caenorhabditis elegans revealed that apoptotic cell death involves at least 14 genes, two of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (Apoptosis and Cancer Chemotherapy, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9—BCL-like and CED-3—ICE-like gene family products. These are intrinsic proteins that regulate the decision of a cell to survive or die and they execute part of the cell death process itself (see Schmitt, et al., Biochem. Cell. Biol. 75:301–314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los et al., Blood, Vol. 90, No 8:3118–3129 (1997); Friesen, et al., Nat. Med. 2:574 (1996)). The mechanism of action of current antineoplastic drugs frequently involves an attack at specific phases of the cell cycle. In brief, the cell cycle refers to the stages through which cells normally progress during their lifetimes. Normally, cells exist in a resting phase termed $G_o$. During multiplication, cells progress to a stage in which DNA synthesis occurs, termed S. Later, cell division, or mitosis occurs, in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many antineoplastic drugs slow growing tumors. For example, colon cancers exist -primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective toward a slow growing tumor. Other aspects of the chemotherapy of neoplastic diseases are known to those skilled in the art (see, e.g., Hardman, et al., eds., Goodman and Gilman's The Pharmacological Basis of Therapeutics, Ninth Edition, McGraw-Hill, New York (1996), pp. 1225–1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune diseases and certain degenerative diseases also involve the proliferation of abnormal cells, therapeutic treatment for these diseases could also involve the enhancement of the apoptotic process through the administration of appropriate caspase cascade activators and inducers of apoptosis.

Gambogic acid was isolated from gamboge and the structure was deduced from the $^1$H NMR spectrum and by comparison with morellin, which also has the xanthone core of gambogic acid (Ahmad, S. A., et al. *J. Chem. Soc.* (C) 772–779 (1966); Ollis, W. D., et al. *Tetrahedron*, 21:1453–1470 (1965).

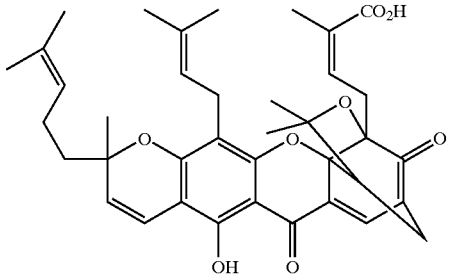

Asano J., et al., *Phytochemistry*, 41:815–820 (1996), reported the isolation of several xanthones, including gambogic acid from gamboge. They reported that gambogic acid is cytotoxic to both HeLa and HEL cells.

Lin, L. -J., et al., *Magn. Reson. Chem.* 31:340–347 (1993), reported the isolation of gambogic acid, as well as isogambogic acid and isomorellinol. All three compounds were reported to be cytotoxic against KB and KB-V1 cell lines.

SUMMARY OF THE INVENTION

The present invention is related to the discovery that gambogic acid, its analogs and derivatives, as represented in Formulae I–III, are activators of the caspase cascade and inducers of apoptosis. Therefore the first aspect of the present invention is directed to the use of compounds of Formulae I–III as inducers of apoptosis.

A second aspect of the present invention is to provide a method for treating, preventing or ameliorating neoplasia and cancer by administering a compound of Formulae I–III to a mammal in need of such treatment.

A number of compounds within the scope of the present invention are novel compounds. Therefore, a third aspect of the present invention is to provide novel compounds of Formulae I–III, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of Formulae I–III in admixture with one or more pharmaceutically acceptable carriers or diluents.

A fifth aspect of the present invention is directed to methods for the isolation and preparation of novel compounds of Formulae 1–111.

BRIEF DESCRIPTION OF THE DRAWINGS

FIG. 5A, Jurkat leukemia cells: (a) DMSO control, (b) treated with 1 μM of staurosporine for 2 h, (c) inactive control, (d) treated with 2.5 μM of gambogic acid for 2 h. FIG. 5B, HL-60 human leukemia cancer cells: (a) DMSO control, (b) treated with 1 μM of staurosporine for 2 h, (c) inactive control, (d) treated with 2.5 μM of gambogic acid for 2 h. FIG. 5C, T47D human breast cancer cells: (a) DMSO control, (b) treated with 1 μM of staurosporine for 2 h, (c) treated with 2.5 μM of gambogic acid for 2 h, (d) treated with 5 μM of gambogic acid for 2 h, (e) DMSO control, (f) treated with 1 μM of staurosporine for 4 h, (g) treated with 2.5 μM of gambogic acid for 4 h, (h) treated with 5 μM of gambogic acid for 4 h. FIG. 5D, PC3 human prostate cancer cells: (a) DMSO control, (b) treated with 1 μM of staurosporine for 2 h, (c) treated with 2.5 μM of gambogic acid for 2 h, (d) treated with 5 μM of gambogic acid for 2 h, (e) DMSO control, (f) treated with 1 μM of staurosporine for 4 h, (g) treated with 2.5 μM of gambogic acid for 4 h, (h) treated with 5 μM of gambogic acid for 4 h.

DETAILED DESCRIPTION OF THE INVENTION

Figure 1A:
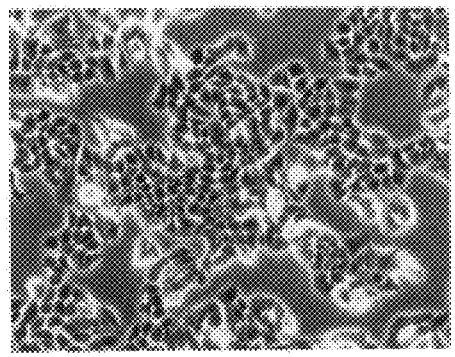
FIGS. 1A–C depict photographs of T47D human breast cancer cells treated with gambogic acid: control cells (FIG. 1A); cells treated with 2.5 μM of gambogic acid for 2 h (FIG. 1B); cells treated with 2.5 μM of gambogic acid for 6 h (FIG. 1C).

The present invention arises out of the discovery that gambogic acid is a potent and highly efficaceous activator of the caspase cascade and inducer of apoptosis. Therefore gambogic acid is useful for treating disorders responsive to induction of apoptosis.

There are many functional groups in the structure of gambogic acid which can be modified. These include, but are not limited to, the carboxyl group, which can be converted to an ester, amide, ketone or alcohol and other functional groups; the ester and amide, in turn, may also contain other functional groups, such as the carboxyl of an amino acid, which can be further modified; the hydroxy group, may be converted to an ether, ester or other functional groups; the carbon-carbon double bond between C-9 and C-10 is part of an α,β-unsaturated ketone, which can react with a nucleophile, be reduced to a carbon-carbon single bond, or may be converted to an epoxide, which in turn may undergo further reaction; the carbon-carbon double bond between C-27 and C-28 is part of an α,β-unsaturated carboxyl, that may also react with a nucleophile, be reduced to a carbon-carbon single bond, or may be converted to a cyclopropane ring, which in turn may undergo further reaction; the two isoprene carbon-carbon double bonds at C-37/C-38 and C-32/C-33, may also be reduced to a carbon-carbon single bond, be cleaved to form an aldehyde group or a carboxyl group, both of which may be modified to other functional groups, or be converted to an epoxide, which in turn may undergo further reaction; the carbon-carbon double bond between C-3 and C-4 may also be reduced to a carbon-carbon single bond, or be converted to an epoxide that may undergo further reaction; the ketone group at C-12 may be reduced to an alcohol, or may be converted to an oxime, a semicarbazone, or an amino group; the other ketone group may also be reduced, or may be converted to other functional groups. In short, many derivatives of gambogic acid can be prepared.

In addition, analogs of gambogic acid, including isomorellin, morellic acid, desoxymorellin, gambogin, morelline dimethyl acetal, isomoreollin B Moreollic acid, gambogenic acid, gambogenin, isogambogenin, desoxygambogenin, gambogenin dimethyl acetal, gambogellic acid, hanburin (Asano, J., et al., *Phytochemistry* 41:815–820 (1996)), isogambogic acid, isomorellinol (Lin, L. -J., et al., *Magn. Reson. Chem.* 31:340–347 (1993)) and neo-gambogic acid (Lu, G. B., et al., *Yao Hsueh Hsueh Pao* 19:636–639 (1984)) can be isolated from gamboge. Other analogs of gambogic acid, including morellin, desoxymorellin, dihydroisomorellin (Bhat et al. *Indian J. Chem.* 2:405–409 (1964)) and moreollin (Rao et al. *Proc. Indian Acad. Sci.* 87A:75–86 (1978)), can be isolated from the seed of *Garcinia morella*. Morellinol can be isolated from the bark of *Garcinia morella* (Adawadkar et al. *Indian J. Chem.* 14B:19–21 (1976)). Gaudichaudiones (A–H) and gaudichaudiic acids A–E can be isolated from the leaves of *Garcinia gaudichaudii* (Guttiferae) (Cao, S. -G., et al., *Tetrahedron* 54(36):10915–10924 (1998) and Cao, S. -G., et al., *Tetrahedron Lett.* 39(20):3353–3356 (1998)), and forbesione can be isolated from *Garcinia forbesii* (Leong, Y. -W., et al., *J. Chem. Res., Synop.* 392–393 (1996)).

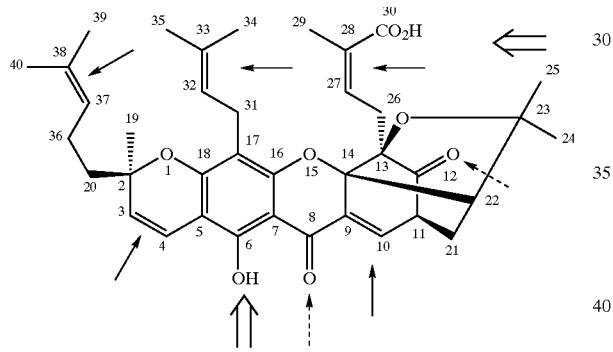

The present invention, therefore, also arises out of the discovery that novel derivatives and analogs of gambogic acid are also activators of the caspase cascade and inducers of apoptosis. Therefore these derivatives and analogs of gambogic acid are useful for treating disorders responsive to the induction of apoptosis.

Specifically, compounds useful in this aspect of the present invention are gambogic acid, its analogs and derivatives as represented by Formulae I–III:

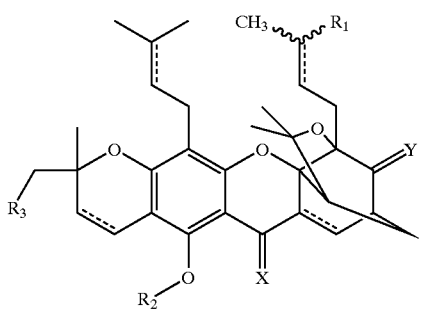

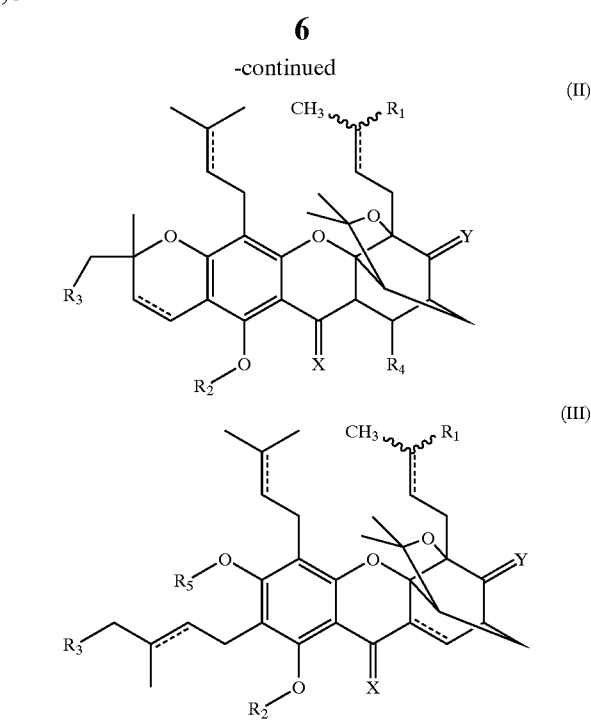

or pharmaceutically acceptable salts or prodrugs thereof, wherein:

the dotted lines are single bonds, double bonds or an epoxy group;

X together with the attached carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

$R_1$ is formyl, methylenehydroxy, carboxy, acyl ($R_aCO$), optionally substituted alkoxycarbonyl ($R_aOCO$), optionally substituted alkylthiocarbonyl, optionally substituted aminocarbonyl (carbamyl, $R_bR_cNCO$) or hydroxyaminocarbonyl, where $R_a$ is hydrogen, optionally substituted lower alkyl, optionally substituted aryl, optionally substituted lower aralkyl group or N-succinimidyl; $R_b$ and $R_c$ are independently hydrogen, optionally substituted heteroalkyl, optionally substituted lower alkyl, optionally substituted aryl, optionally substituted heteroaryl or optionally substituted lower aralkyl groups; or $R_b$ and $R_c$ may be taken together with the attached N to form an optionally substituted, saturated or partially saturated 5–7 membered heterocyclo group, including piperidine, morpholine and piperazine.

$R_2$ is hydrogen, optionally substituted alkyl, acyl ($R_aCO$), carbamyl ($R_bR_cNCO$) or sulfonyl ($R_dSO_2$), where $R_a$, $R_b$ and $R_c$ are defined above; $R_d$ is hydrogen, optionally substituted lower alkyl, optionally substituted aryl, or optionally substituted lower aralkyl groups;

$R_3$ is hydrogen or prenyl;

$R_4$ is hydrogen, halogen, hydroxy, optionally substituted alkyl, cycloalkyl, alkoxy, alkylthio or amino;

$R_5$ is hydrogen, optionally substituted alkyl or acyl ($R_aCO$), carbamyl ($R_bR_cNCO$) or sulfonyl ($R_dSO_2$), where $R_a$, $R_b$, $R_c$ and $R_d$ are defined above.

Preferred compounds falling within the scope of Formula I include compounds wherein $R_1$ is formyl, acetyl, propionyl, carboxy, methoxycarbonyl, ethoxycarbonyl, methylthiocarbonyl, ethylthiocarbonyl, butylthiocarbonyl, dimethylcarbamyl, diethylcarbamoyl, 1-piperidinylcarbonyl, N-methyl-N'-piperazinylcarbonyl, 2-(dimethylamino)ethylcarbamyl or N-morpholinylcarbonyl; $R_2$ is hydrogen, formyl, acetyl, dimethylcarbamyl, diethylcarbamyl, 2-(dimethylamino)ethylcarbamyl, 1-piperidinylcarbonyl, N-methyl-N'-piperazinylcarbonyl, N-morpholinyl-carbonyl, methylsulfonyl, ethylsulfonyl, phenylsulfonyl, methyl, ethyl, 2-piperidinylethyl, 2-morpholinylethyl, 2-(dimethylamino)ethyl, or 2-(diethylamino)ethyl; X and Y is O; $R_3$ is prenyl; and the dotted lines are double bonds or an epoxy group. If the double bond is present at C27–28, it is preferred that it has the Z configuration.

Preferred compounds falling within the scope of Formula II include compounds wherein $R_1$ is formyl, acetyl, propionyl, carboxy, methoxycarbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N'-piperazinylcarbonyl, 2-(dimethylamino)ethylcarboxy or N-morpholinylcarbonyl; $R_2$ is hydrogen, formyl, acetyl, dimethylcarbamyl, diethylcarbamyl, 2-(dimethylamino)ethylcarbamyl, 1-piperidinylcarbonyl, N-methyl-N'-piperazinylcarbonyl, N-morpholinylcarbonyl, methylsulfonyl, ethylsulfonyl, phenylsulfonyl, methyl, ethyl, 2-piperidinylethyl, 2-morpholinylethyl, 2-(dimethylamino)ethyl, or 2-(diethylamino)ethyl; and $R_4$ is methyl, ethyl, phenyl, chloro, bromo, hydroxy, hydrogen, methoxy, ethoxy, methylthio, ethylthio, butylthio, dimethylarnino, diethylamino, piperidinyl, pyrrolidinyl, imidazolyl, pyrazolyl, N-methylpiperazinyl, 2-(dimethylamino)ethylamino or morpholinyl; X and Y is O; $R_3$ is prenyl; and the dotted lines are double bonds. If the double bond is present at C27–28, it is preferred that it has the Z configuration.

Preferred compounds falling within the scope of Formula III include compounds wherein $R_1$ is formyl, acetyl, propionyl, carboxy, methoxycarbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N'-piperazinylcarbonyl, 2-(dimethylamino)ethylcarbamyl or N-morpholinylcarbonyl; $R_2$ is hydrogen, formyl, acetyl, dimethylcarbamyl, diethylcarbamyl, 2-(dimethylamino)ethylcarbamyl, 1-piperidinylcarbonyl, N-methyl-N'-piperazinylcarbonyl, N-morpholinylcarbonyl, methylsulfonyl, ethylsulfonyl, phenylsulfonyl, methyl, ethyl, 2-piperidinylethyl, 2-morpholinylethyl, 2-(dimethylamino)ethyl, or 2-(diethylamino)ethyl; $R_5$ is hydrogen, formyl, acetyl, dimethylcarbamyl, diethylcarbamyl, 2-(dimethylamino)ethylcarbamyl, 1-piperidinylcarbonyl, N-methyl-N'-piperazinylcarbonyl, N-morpholinylcarbonyl, methylsulfonyl, ethylsulfonyl, phenylsulfonyl, methyl, ethyl, 2-piperidinylethyl, 2-morpholinylethyl, 2-(dimethylamino)ethyl, or 2-(diethylamino)ethyl; X and Y is O; $R_3$ is prenyl; and the dotted lines are double bonds. If the double bond is present at C27–28, it is preferred that it has the Z configuration.

Exemplary preferred compounds that may be employed in the method of invention include, without limitation:

Gambogic acid;
Methyl gambogate;
9,10-Dihydrogambogic acid;
9,10-Dihydrogambogyl (4-methylpiperazine);
9,10-Dihydrogambogyl (2-dimethylaminoethylamine);
Gambogyl diethylamine;
Gambogyl dimethylamine;
Gambogyl amine;
Gambogyl hydroxyamine;
Gambogyl piperidine;
6-Methoxy-gambogic acid;
6-(2-Dimethylaminoethoxy)-gambogic acid;
6-(2-Piperidinylethoxy)-gambogic acid;
6-(2-Morpholinylethoxy)-gambogic acid;
6-Methoxy-gambogyl piperidine;
Gambogyl morpholine;
Gambogyl (2-dimethylaminoethylamine);
10-Morpholinyl-gambogyl morpholine;
10-Morpholinyl-gambogyl piperidine;
10-(4-Methylpiperazinyl)-gambogyl piperidine;
10-(4-Methylpiperazinyl)-gambogyl morpholine;
10-Piperidinyl-gambogyl piperidine;
10-(4-Methylpiperazinyl)-gambogyl (4-methylpiperazine);
Gambogyl (4-methylpiperazine);
Methyl-6-methoxy-gambogate;
Gambogenic acid;
Gambogenin;
10-Methoxy-gambogic acid;
10-Butylthio-gambogic acid;
10-(4-Methylpiperazinyl)-gambogic acid;
10-Pyrrolidinyl-gambogic acid;
Methyl-10-Morpholinyl-gambogate;
10-Piperidinyl-gambogic acid;
10-Morpholinyl-gambogic acid;
N-(2-Gambogylamidoethyl)biotinamide;
Gambogyl (2-morpholinylethylamine);
9,10-Epoxygambogic acid;
Gambogyl (4-(2-pyridyl)piperazine);
10-(4-(2-Pyridyl)piperazinyl)gambogyl (4-(2-pyridyl)piperazine);
6-Acetylgambogic acid;
10-(4-(2-Pyridyl)piperazinyl)gambogic acid;
N-Hydroxysuccinimidyl gambogate;
8-(Gambogylamido)octanoic acid;
6-(Gambogylamido)hexanoic acid;
12-(Gambogylamido)dodecanoic acid;
N-Hydroxysuccinimidyl-8-(gambogylamido)octanoate;
N-Hydroxysuccinimidyl-6-(gambogylamido)hexanoate;
N-Hydroxysuccinimidyl-12-(gambogylamido)dodecanoate;
10-Methoxy-gambogyl piperidine;
Gambogyl (4-(2-pyrimidyl)piperazine);
Gambogyl (bis(2-pyridylmethyl)amine);
Gambogyl (N-(3-pyridyl)-N-(2-hydroxybenzyl)amine);
Gambogyl (4-benzylpiperazine);
Gambogyl (4-(3,4-methylenedioxybenzyl)piperazine);
Gambogyl (N-methyl-5-(methylamino)-3-oxapentylamine);
Gambogyl (N-methyl-8-(methylamino)-3,6-dioxaoctylamine);
Gambogyl (N-ethyl-2-(ethylamino)ethylamine);

Gambogyl (4-isopropylpiperazine);
Gambogyl (4-cyclopentylpiperazine);
Gambogyl (N-(2-oxo-2-ethoxyethyl)-(2-pyridyl) methylamine);
Gambogyl (2,5-dimethylpiperazine);
Gambogyl (3,5-dimethylpiperazine);
Gambogyl (4-(4-acetylphenyl)piperazine);
Gambogyl (4-ethoxycarbonylpiperazine);
Gambogyl (4-(2-oxo-2-pyrrolidylethyl)piperazine);
Gambogyl (4-(2-hydroxyethyl)piperazine);
Gambogyl (N-methyl-2-(methylamino)ethylarnine);
Gambogyl (N-methyl-2-(benzylamino)ethylamine);
Gambogyl (N-methyl-(6-methyl-2-pyridyl) methylamine);
Gambogyl (N-ethyl-2-(2-pyridyl)ethylamine);
Gambogyl (N-methyl-(2-pyridyl)methylamine);
Gambogyl (N-methyl-4-(3-pyridyl)butylamine);
Gambogyl (bis(3-pyridylmethyl)amine);
Gambogyl (2,4-dimethyl-2-imidazoline);
Gambogyl (4-methyl-homopiperazine);
Gambogyl (4-(5-hydroxy-3-oxapentyl)piperazine);
Gambogyl (3-dimethylaminopyrrolidine);
Gambogyl ((2-furanyl)methylamine);
Gambogyl (2-hydroxy-1-methyl-2-phenylethylamine);
Gambogyl (3,4,5-trimethoxybenzylamine);
Gambogyl (2-(2-methoxyphenyl)ethylamine);
Gambogyl (2-methoxybenzylamine);
Gambogyl (3,4-methylenedioxybenzylamine);
Gambogyl (2-(2,5-dimethoxyphenyl)ethylamine);
Gambogyl (2-(3-methoxyphenyl)ethylamine);
Gambogyl (3-(piperidinyl)propylamine);
Gambogyl (2-(piperidinyl)ethylamine);
Gambogyl (3,4-dimethoxybenzylamine);
Gambogyl ((2-tetrahydrofuranyl)methylamine);
Gambogyl ((N-ethyl-2-pyrrolidinyl)methylamine);
Gambogyl (2-diethylaminoethylamine);
Gambogyl (2,2-dimethyl-3-dimethylaminopropylamine);
Gambogyl ((N-ethoxycarbonyl-4-piperidinyl)amine);
Gambogyl (2-carbamylpyrrolidine);
Gambogyl (3-(homopiperidinyl)propylamine);
Gambogyl ((N-benzyl-4-piperidinyl)amine);
Gambogyl (2-(4-methoxyphenyl)ethylamine);
Gambogyl (4-oxa-hex-5-enylamine);
Ganbogyl (6-hydroxyhexylamine);
Gambogyl (2-(3,5-dimethoxyphenyl)ethylamine);
Gambogyl (3,5-dimethoxybenzylamine); and
Gambogyl (2-carbamyl-2-(4-hydroxyphenyl) ethylamine).

The positions in gambogic acid are numbered according to Asano, J., et al., *Phytochemistry* 41:815–820 (1996), and Lin, L. -J., et al., *Magn. Reson. Chem.* 31:340–347 (1993).

The present invention is also directed to novel compounds within the scope of Formulae I–III. These compounds include compounds of Formula I wherein if $R_1$ is carboxy or methoxycarbonyl and X and Y are O, then $R_2$ is not hydrogen or methyl. These compounds also include compounds of Formula II wherein if $R_1$ is formyl or carboxy, $R_2$ is hydrogen, $R_3$ is hydrogen and X and Y are O, then $R_4$ is not methoxy or ethoxy. These compounds also include compounds of Formula III wherein if $R_1$ is formyl or carboxy and X and Y are O, then at least one of $R_2$ or $R_5$ are not hydrogen.

Exemplary preferred compounds that may be employed in this invention include, without limitation:
9,10-Dihydrogambogyl (4-methylpiperazine);
9,10-Dihydrogambogyl (2-(dimethylamino)ethylamine);
9,10-Dihydro-1 2-hydroxygambogic acid;
Gambogyl diethylamine;
Gambogyl dimethylamine;
Gambogyl amine;
Gambogyl hydroxyamine;
Gambogyl piperidine;
6-Methoxy-gambogic acid;
6-(2-Dimethylaminoethoxy)-gambogic acid;
6-(2-Piperidinylethoxy)-gambogic acid;
6-(2-Morpholinylethoxy)-gambogic acid;
6-Methoxy-gambogyl piperidine;
Gambogyl 4-morpholine;
Gambogyl 2-(dimethylamino)ethylamine;
10-Morpholinyl-gambogyl morpholine;
10-Morpholinyl-gambogyl piperidine;
10-(4-Methylpiperazinyl)-gambogyl piperidine;
10-(4-Methylpiperazinyl)-gambogyl morpholine;
10-Piperidinyl-gambogyl piperidine;
10-(4-Methylpiperazinyl)-gambogyl (4-methylpiperazine);
Gambogyl (4-methylpiperazine);
10-Methoxy-gambogic acid;
10-Butylthio-gambogic acid;
10-(4-Methylpiperazinyl)-gambogic acid;
10-Pyrrolidinyl-gambogic acid;
Methyl-10-Morpholinyl-gambogate;
10-Piperidinyl-gambogic acid;
10-Morpholinyl-gambogic acid;
10-Cyclohexyl-gambogic acid;
10-Methyl-gambogic acid;
N-(2-Gambogylamido-ethyl)biotinamide;
Gambogyl (2-(4-morpholinyl)ethylamine);
9,10-Epoxygambogic acid;
Gambogyl (4-(2-pyridyl)piperazine);
10-(4-(2-Pyridyl)piperazinyl)gambogyl (4-(2-pyridyl) piperazine);
6-Acetylgambogic acid;
10-(4-(2-Pyridyl)piperazinyl)gambogic acid;
N-Hydroxysuccinimidyl gambogate;
8-(Gambogylamido)octanoic acid;
6-(Gambogylamido)hexanoic acid;
12-(Gambogylamido)dodecanoic acid;
N-Hydroxysuccinimidyl-8-(gambogylamido)octanoate;
N-Hydroxysuccinimidyl-6-(gambogylamido)hexanoate;
N-Hydroxysuccinimidyl-12-(gambogylamido) dodecanoate;
10-Methoxy-gambogyl piperidine;
Gambogyl (4-(2-pyrimidyl)piperazine);
Gambogyl (bis(2-pyridylmethyl)amine);
Gambogyl (N-(3-pyridyl)-N-(2-hydroxybenzyl)amine);
Gambogyl (4-benzylpiperazine);

Gambogyl (4-(3,4-methylenedioxybenzyl)piperazine);
Gambogyl (N-methyl-5-(methylamino)-3-oxapentylamine);
Gambogyl (N-methyl-8-(methylamino)-3,6-dioxaoctylamine);
Gambogyl (N-ethyl-2-(ethylamino)ethylamine);
Gambogyl (4-isopropylpiperazine);
Gambogyl (4-cyclopentylpiperazine);
Gambogyl (N-(2-oxo-2-ethoxyethyl)-(2-pyridyl)methylamine);
Gambogyl (2,5-dimethylpiperazine);
Gambogyl (3,5-dimethylpiperazine);
Gambogyl (4-(4-acetylphenyl)piperazine);
Gambogyl (4-ethoxycarbonylpiperazine);
Gambogyl (4-(2-oxo-2-pyrrolidylethyl)piperazine);
Gambogyl (4-(2-hydroxyethyl)piperazine);
Gambogyl (N-methyl-2-(methylamino)ethylamine);
Gambogyl (N-methyl-2-(benzylamino)ethylamine);
Gambogyl (N-methyl-(6-methyl-2-pyridyl)methylamine);
Gambogyl (N-ethyl-2-(2-pyridyl)ethylamine);
Gambogyl (N-methyl-(2-pyridyl)methylamine);
Gambogyl (N-methyl-4-(3-pyridyl)butylamine);
Gambogyl (bis(3-pyridylmethyl)amine);
Gambogyl (2,4-dimethyl-2-imidazoline);
Gambogyl (4-methyl-homopiperazine);
Gambogyl (4-(5-hydroxy-3-oxapentyl)piperazine);
Gambogyl (3-dimethylaminopyrrolidine);
Gambogyl ((2-furanyl)methylamine);
Gambogyl (2-hydroxy-1-methyl-2-phenylethylamine);
Gambogyl (3,4,5-trimethoxybenzylamine);
Gambogyl (2-(2-methoxyphenyl)ethylamine);
Gambogyl (2-methoxybenzylamine);
Gambogyl (3,4-methylenedioxybenzylamine);
Gambogyl (2-(2,5-dimethoxyphenyl)ethylamine);
Gambogyl (2-(3-methoxyphenyl)ethylamine);
Gambogyl (3-(piperidinyl)propylamine);
Gambogyl (2-(piperidinyl)ethylamine);
Gambogyl (3,4-dimethoxybenzylamine);
Gambogyl ((2-tetrahydrofuranyl)methylamine);
Gambogyl ((N-ethyl-2-pyrrolidinyl)methylamine);
Gambogyl (2-diethylaminoethylamine);
Gambogyl (2,2-dimethyl-3-dimethylaminopropylamine);
Gambogyl ((N-ethoxycarbonyl-4-piperidinyl)amine);
Gambogyl (2-carbamylpyrrolidine);
Gambogyl (3-(homopiperidinyl)propylamine);
Gambogyl ((N-benzyl-4-piperidinyl)amine);
Gambogyl (2-(4-methoxyphenyl)ethylamine);
Gambogyl (4-oxa-hex-5-enylamine);
Ganbogyl (6-hydroxyhexylamine);
Gambogyl (2-(3,5-dimethoxyphenyl)ethylamine);
Gambogyl (3,5-dimethoxybenzylamine); and
Gambogyl (2-carbamyl-2-(4-hydroxyphenyl)ethylamine).

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

Useful alkoxy groups include oxygen substituted by one of the $C_{1-10}$ alkyl groups mentioned above, which may be optionally substituted.

Useful alkylthio groups include sulphur substituted by one of the $C_{1-10}$ alkyl groups mentioned above, which may be optionally substituted. Also included are the sulfoxides and sulfones of such alkylthio groups.

Useful amino groups include $-NH_2$, $-NHR_{11}$, and $-NR_{11}R_{12}$, wherein $R_{11}$ and $R_{12}$ are $C_{1-10}$ alkyl or cycloalkyl groups, or $R_{11}$ and $R_{12}$ are combined with the N to form a ring structure, such as a piperidine, or $R_{11}$ and $R_{12}$ are combined with the N and another heteroatom to form an optionally substituted, saturated or partially saturated 5–7 membered heterocyclo group, such as a piperazine. The alkyl group may be optionally substituted.

Useful heteroatoms include N, O or S.

Optional substituents on the alkyl groups include one or more halo, hydroxy, carboxyl, alkoxycarbonyl, amino, nitro, cyano, $C_1$–$C_6$ acylamino, $C_1$–$C_6$ aminoacyl, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, $C_2$–$C_6$ alkynyl, $C_6$–$C_{10}$ aryl($C_2$–$C_6$)alkenyl, $C_6$–$C_{10}$ aryl($C_2$–$C_6$)alkynyl, saturated or partially saturated 5–7 membered heterocyclo group, or heteroaryl.

Optional substituents on the aryl, aralkyl and heteroaryl groups include one or more acyl, alkylenedioxy ($-OCH_2O-$), halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy, or carboxy.

Useful heteroalkyl groups contain 1–10 carbon atoms and 1, 2 or 3 heteroatoms. Examples of heteroalkyl groups include $-CH_2CH_2OCH_2CH_3$, $-CH_2CH_2OCH_2CH_2OCH_2CH_3$, $-CH_2CH_2NHCH_3$, $-CH_2CH_2N(CH_2CH_3)_2$, $-CH_2CH_2OCH_2CH_2NHCH_3$, $-CH_2CH_2OCH_2CH_2OCH_2CH_2NHCH_3$, $-CH_2CH_2NHCH_2CH_3$, $-CH_2C(CH_3)_2CH_2N(CH_3)_2$ or $-CH_2$(N-ethylpyrrolidine), which may be optionally substituted.

Optional substituents on heteroalkyl groups include one or more halo, hydroxy, carboxyl, amino, nitro, cyano, alkyl, $C_1$–$C_6$ acylamino, $C_1$–$C_6$ aminoacyl, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, alkenoxy, $C_2$–$C_6$ alkynyl, $C_6$–$C_{10}$ aryl ($C_2$–$C_6$)alkenyl, $C_6$–$C_{10}$ aryl($C_2$–$C_6$)alkynyl, saturated and unsaturated heterocyclic, or heteroaryl.

Useful aryl groups are $C_{6-14}$ aryl, especially $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful aralkyl groups include any of the above-mentioned $C_{1-10}$ alkyl groups substituted by any of the above-mentioned $C_{6-14}$ aryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl, chloromethyl, chlorofluoromethyl and trichloromethyl groups.

Useful acylamino groups are any $C_{1-6}$ acyl (alkanoyl) attached to an amino nitrogen, e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. formyloxy, acetoxy, propionoyloxy, butanoyloxy, pentanoyloxy, hexanoyloxy and the like.

Useful saturated or partially saturated 5–7 membered heterocyclo groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Optional substitutents on the 5–7 membered heterocyclo groups include one or more heteroaryl, heterocyclo, alkyl, aralkyl, cycloalkyl, alkoxycarbonyl, carbamyl, aryl or $C_1$–$C_6$ aminoacyl.

Useful heteroaryl groups include any one of the following: thienyl, benzo[b]thienyl, naphtho[2,3-b]thienyl, thianthrenyl, furanyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Optional substituents on the heteroaryl groups include one or more heteroaryl, heterocyclo, alkyl, aralkyl, cycloalkyl, alkoxycarbonyl, carbamyl, aryl and $C_1$–$C_6$ aminoacyl.

Certain compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxy, Tris(hydroxymethyl) aminomethane (TRIS, tromethane) and N-methyl-glucamine.

Examples of prodrugs of the compounds of the invention include the simple esters of carboxylic acid containing compounds (e.g. those obtained by condensation with a $C_{1-4}$ alcohol according to methods known in the art); esters of hydroxy containing compounds (e.g. those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g. those obtained by condensation with a $C_{1-4}$ aldehyde or ketone according to methods known in the art); and acetals and ketals of alcohol containing compounds (e.g. those obtained by condensation with chloromethyl methyl ether or chloromethyl ethyl ether according to methods known in the art).

The compounds of this invention may be prepared and purified using methods known to those skilled in the art, or the novel methods of this invention. Specifically, gambogic acid can be purified by 1) preparation of the pyridine salt of the crude extract from gamboge (resin from *Garcinia hanburyi* Hook) followed by repeated recrystallization of the salt in ethanol or 2) converting the salt to the free acid. Using this procedure, about 10% by weight of gambogic acid with purity >99% (HPLC) can be obtained from the crude extract. Gambogic acid and analogs of gambogic acid with Formula I–III also can be separated and purified from gamboge by repeated chromatography ($SiO_2$, hexane-EtOAc gradient) using a Combi Flash SG 100 separation system.

Derivatives of gambogic acid with Formula I can be prepared as illustrated by exemplary reactions in Schemes 1 and 2. Reaction of gambogic acid with methanol in the presence of DMAP and EDC produced the methyl ester of gambogic acid (Scheme 1). Reaction of gambogic acid with piperidine in the presence of DMAP and EDC produced the piperidinyl amide of gambogic acid (Scheme 2).

Scheme 1

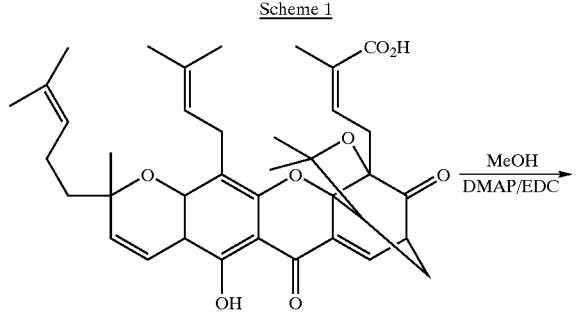

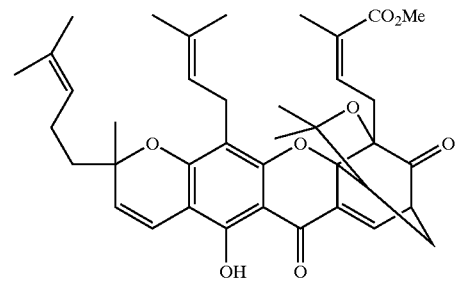

Scheme 2

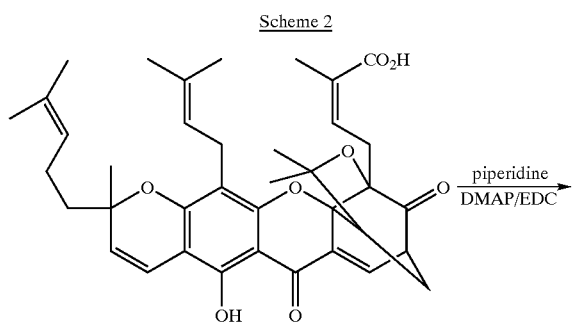

piperidine
———————→
DMAP/EDC

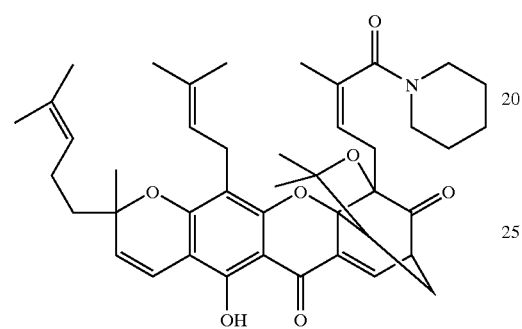

Derivatives of gambogic acid with Formula I can also be prepared as illustrated by exemplary reactions in Schemes 3–5. Reaction of methyl gambogate with methyl iodide in the presence of a base, such as $K_2CO_3$, produced the methyl-6-methoxy-gambogate (Scheme 3). Reaction of gambogic acid with acetic anhydride in pyridine produced 6-acetyl gambogic acid (Scheme 4). Reaction of gambogic acid with $H_2O_2$ under basic conditions produced 9,10-epoxygambogic acid (Scheme 5).

Scheme 3

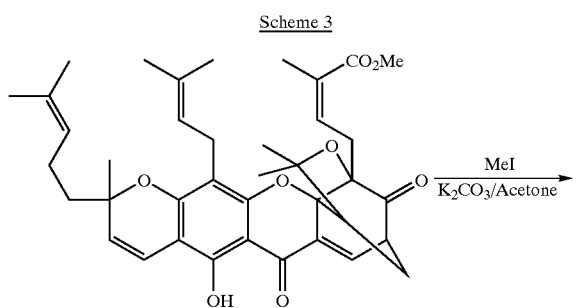

MeI
———————→
$K_2CO_3$/Acetone

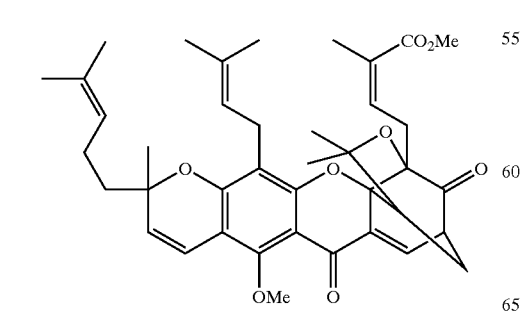

Scheme 4

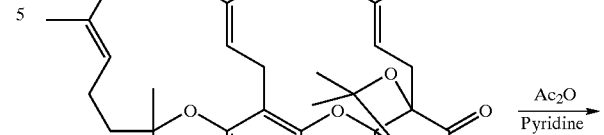

$Ac_2O$
———————→
Pyridine

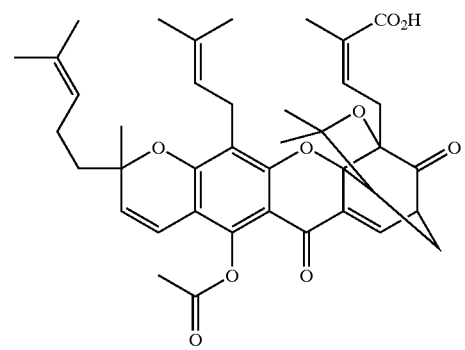

Scheme 5

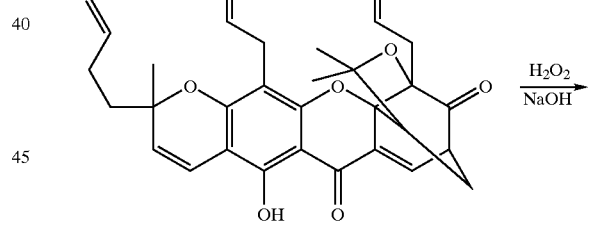

$H_2O_2$
———————→
NaOH

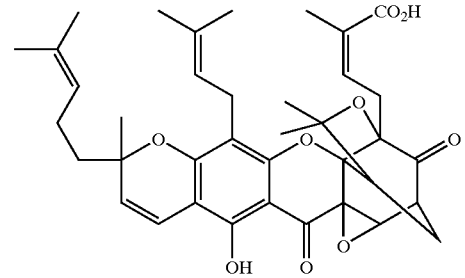

Derivatives of gambogic acid with Formula II can be prepared as illustrated by exemplary reactions in Schemes 6–10. Reaction of gambogyl piperidine with sodium meth oxide produced the methoxy addition product of the amide (Scheme 6). Similarly, reaction of gambogic acid with an amine, such as morpholine, with or without the presence of a base, such as Et₃N, produced the morpholine addition product of gambogic acid (Scheme 7). Reaction of the piperidine amide of gambogic acid with N-methylpiperazine produced the N-methylpiperazine addition product of the amide (Scheme 8). Reduction of gambogic acid by NaBH₄ gave 9,10-dihydro-12-hydroxygambogic acid, which may be oxidized by Dess-Martin reagent to gave 9,10-dihydro-gambogic acid (Scheme 9). Alternatively, selective reduction of gambogic acid by L-selectride also produced 9,10-dihydrogambogic acid (Scheme 9). Reaction of gambogic acid with an alkylcuprate, such as cyclohexylcuprate, resulted in the addition of the alkyl group to the 10-position, thereby producing 10-cyclohexyl-gambogic acid (Scheme 10).

Scheme 7

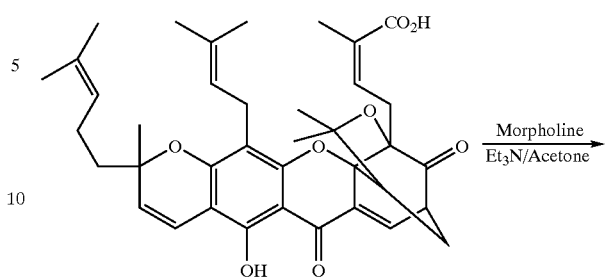

Scheme 6

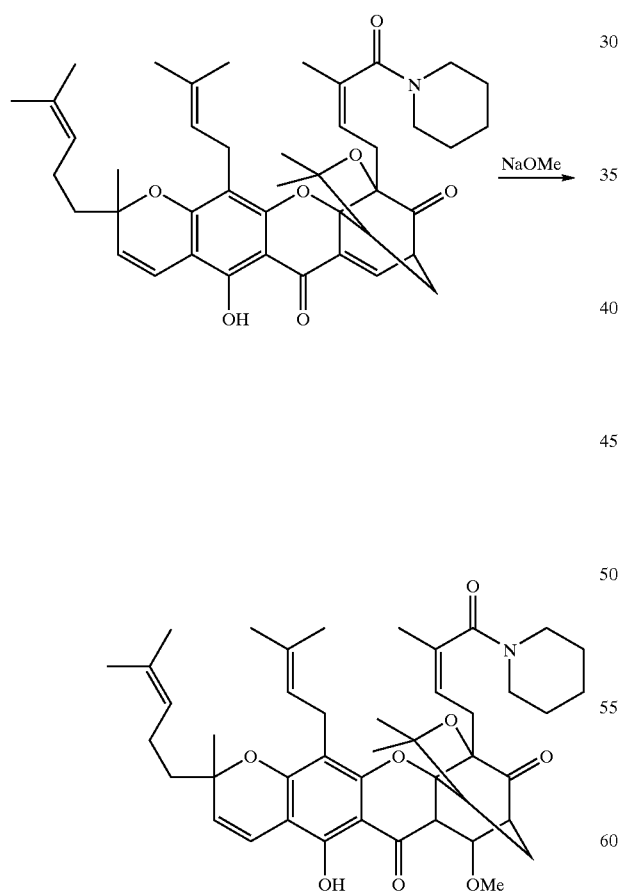

Scheme 8

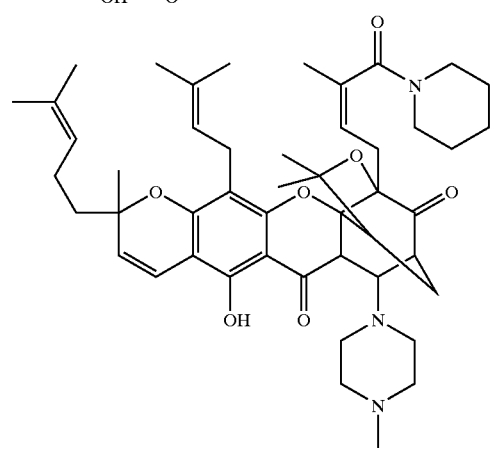

Scheme 9

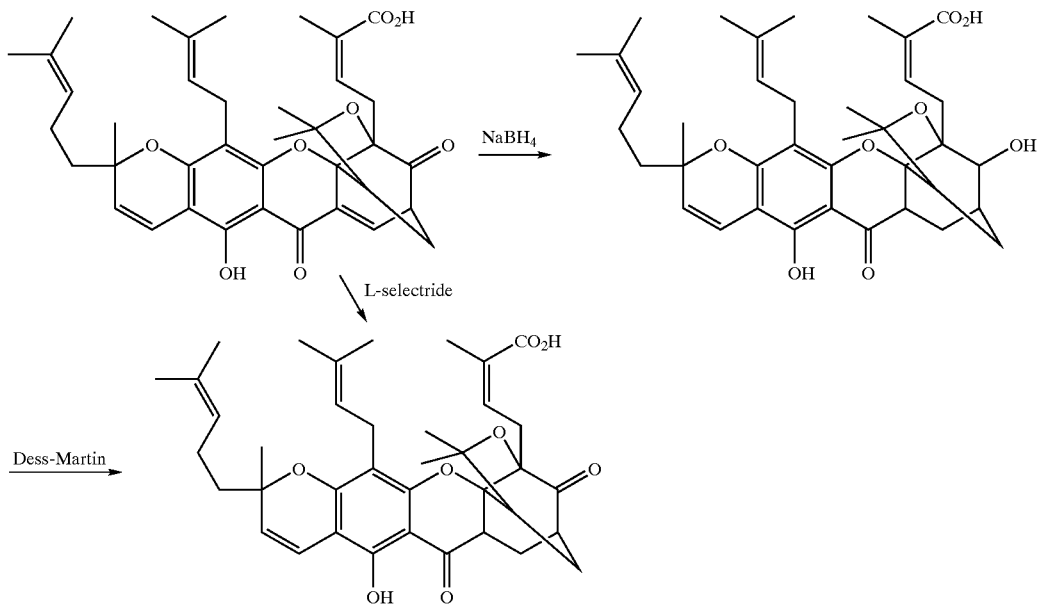

Scheme 10

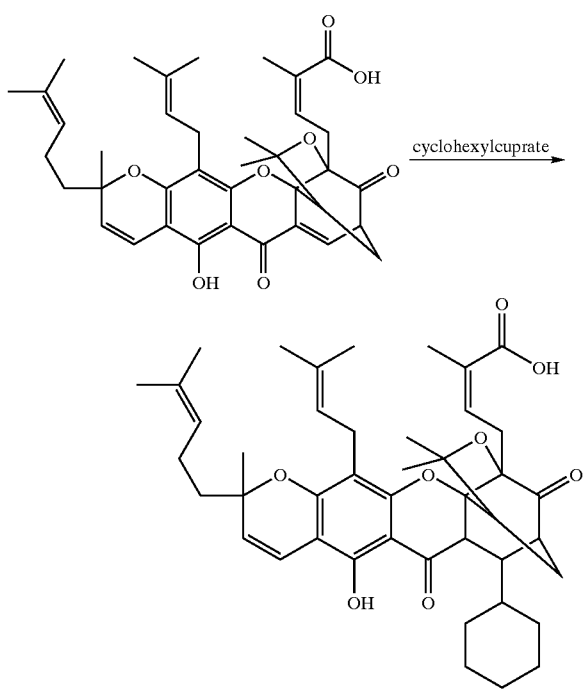

An important aspect of the present invention is the discovery that compounds having Formula I–III are activators of caspases and inducers of apoptosis. Therefore, these compounds are expected to be useful in a variety of clinical conditions in which there is uncontrolled cell growth and spread of abnormal cells, such as in the case of cancer.

Another important aspect of the present invention is the discovery that compounds having Formula I–III are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, gambogic acid, its derivatives and analogs are expected to be useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of a compound of Formulae I–III, which functions as a caspase cascade activator and inducer of apoptosis.

The present invention also includes a therapeutic method comprising administering to an animal an effective amount of a compound, or a pharmaceutically acceptable salt or prodrug of said compound of Formulae I–III, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute and chronic lymphocytic leukemias, multiple myeloma, neuroblastoma, breast carcinomas, ovarian carcinomas, lung carcinomas, Wilms' tumor, cervical carcinomas, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms.

In another embodiment, a pharmaceutical composition comprising a compound, or a pharmaceutically acceptable salt of said compound of Formulae I–III, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I–III, which functions as a caspase cascade activator and inducer of apoptosis, in combination with at least one known cancer chemotherapeutic agent, or a pharmaceutically acceptable salt of said agent. Examples of known anti-cancer agents which can be used for combination therapy include, but are not limited to, alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as Herceptin® (trastuzumab) and Rituxan® (rituximab). Other known anti-cancer agents which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from the at least one known cancer chemotherapeutic agent. In this embodiment, the compound of the invention and the at least one known cancer chemotherapeutic agent are administered substantially simultaneously, i.e. the compounds are administered at the same time or one after the other, so long as the compounds reach therapeutic levels in the blood.

Another embodiment of the present invention is directed to a composition effective to inhibit neoplasia comprising a bioconjugate of said compound of Formulae I–III, which functions as a caspase cascade activator and inducer of apoptosis, in bioconjugation with at least one known therapeutically useful antibody, such as Herceptin® (trastuzumab) or Rituxan® (rituximab), growth factors such as DGF, NGF, cytokines such as IL-2, IL-4, or any molecule that binds to the cell surface. The antibodies and other molecules will deliver the compound of Formulae I–III to its target and make it an effective anticancer agent. The bioconjugate could also enhance the anticancer effect of therapeutically useful antibodies, such as Herceptin® (trastuxumab) or Rituxan® (rituximab).

Similarly, another embodiment of the present invention is directed to a composition effective to inhibit neoplasia comprising a compound, or a pharmaceutically acceptable salt or prodrug of said compound of Formulae I–III, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I–III, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection.

The elimination of the effector cells following an infection is one of the major mechanisms maintaining immune homeostasis. This deletion of reactive cells has been shown to be regulated by a phenomenon known as apoptosis. Autoimnmune diseases have been recently identified to occur as a consequence of deregulated cell death. In certain autoimmune diseases, the immune system directs its powerful cytotoxic effector mechanisms against specialized cells such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ* 6(1):13–21 (1999)). Mutations of the gene encoding the lymphocyte apoptosis receptor Fas/APO-1/CD95 are reportedly associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr*. 133(5):629–633 (1998) and Vaishnaw, A. K., et al., *J. Clin. Invest*. 103(3):355–363 (1999)). It was reported that overexpression of Bcl-2, which is a member of the Bcl-2 gene family of programmed cell death regulators with anti-apoptotic activity in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med*. 1(2): 475–483 (1998)). It is therefore evident that many types of autoimmune diseases are caused by defects of the apoptotic process. One treatment strategy for autoimmune diseases is to turn on apoptosis in the lymphocytes that are causing the autoimnmune disease (O'Reilly, L. A. & Strasser, A., *Inflamm Res* 48(1):5–21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model for the study of the therapeutic effects of FasL. Batteux, F., et al., *J. Immu-* nol. 162(1):603–608 (1999)) reported that the direct injection of DNA expression vectors encoding FasL into the inflamed thyroid inhibited the development of lymphocytic infiltration of the thyroid. In addition, the death of infiltrating T cells was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, and both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T. et al. (*Nat Med* 5(1):42–8 (1999)) reported that administration of bisindolylmaleimide VIII to rats during autoantigen stimulation prevented the development of symptoms of T cell-mediated autoimmune diseases in two models: the Lewis rat model of experimental allergic encephalitis and the Lewis adjuvant arthritis model. Therefore, the application of a Fas-dependent apoptosis enhancer such as bisindolylmaleimide VIII may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I–III, which functions as a caspase cascade activator and inducer of apoptosis, should be an effective treatment for autoimmune disease.

Psoriasis is a chronic skin disease which is characterized by scaly red patches. Psoralen plus ultraviolet A (PUVA) is a widely used and effective treatment for psoriasis vulgaris. Coven, et al., *Photodermatol Photoimmunol Photomed* 15(1):22–7 (1999), reported that lymphocytes treated with psoralen 8-MOP or TMP plus UVA displayed DNA degradation patterns typical of apoptotic cell death. Ozawa, et al., *J. Exp. Med* 189(4):711–718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290(5):240–245 (1998), reported that low doses of methotrexate may induce apoptosis and this mode of action could explain the reduction in epidermal hyperplasia during treatment of psoriasis with methotrexate. Therefore, an effective amount of a compound, or a pharmaceutically acceptable salt or prodrug of the compound of Formulae I–III, which functions as a caspase cascade activator and inducer of apoptosis, should be an effective treatment for psoriasis.

Synovial cell hyperplasia is a characteristic of patients with rheumatoid arthritis (RA). Excessive proliferation of RA synovial cells as well as defects in synovial cell death may be responsible for synovial cell hyperplasia. Wakisaka, et al., *Clin. Exp. Immunol.* 114(1):119–28 (1998), found that although RA synovial cells could die via apoptosis through Fas/FasL pathway, apoptosis of synovial cells was inhibited by proinflammatory cytokines present within the synovium. This suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I–III, which functions as a caspase cascade activator and inducer of apoptosis, should be an effective treatment for RA.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61(4): 375–80 (1997)). Boirivant, et al., *Gastroenterology* 116(3): 557–65 (1999), reported that lamina propria T cells isolated from areas of inflammation in Croln's disease, ulcerative colitis, and other inflammatory states manifest decreased CD2 pathway-induced apoptosis. Moreover, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I–III, which functions as a caspase cascade activator and inducer of apoptosis, should be an effective treatment for inflammation.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day, per kg of body weight of the mammal being treated for apoptosis-mediated disorders. Preferably, about 0.01 to about 10 mg/kg is orally administered to treat or prevent such disorders. For intramuscular injection, the dose is generally about one-half of the oral dose. For example, a suitable intramuscular dose would be about 0.0025 to about 25 mg/kg, and most preferably, from about 0.01 to about 5 mg/kg. If a known cancer chemotherapeutic agent is also administered, it is administered in an amount with is effective to achieve its intended purpose. The amounts of such known cancer chemotherapeutic agents effective for cancer are well known to those of ordinary skill in the art.

The unit oral dose may comprise from about 0.01 to about 50 mg, preferably about 0.1 to about 10 mg of the compound of the invention. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base such as sodium hydroxide, potassium hydroxide, choline hydroxide, sodium carbonate, Tris, N-methyl-glucamine and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which may be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose. binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which may be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like, by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil, such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil, such as almond oil, with warm soft paraffin and allowing the mixture to cool. A typical example of such an ointment is one which includes about 30% almond oil and about 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Gambogic Acid

Procedure 1:

Step A. The dry gamboge powder (140 g) was extracted with MeOH (3×600 mL) at room temperature for 1 week, after filtration, the solvent was removed under reduced pressure, gave crude extract (122 g) as yellow powder.

Step B. Gambogic acid pyridine salt. The above crude extract (120 g) was dissolved in pyridine (120 mL), then warm water (30 mL) was added to the stirred solution. After cooling to r.t., some precipitate was observed. Hexane (120 mL) was added to the mixture and the mixture was filtered and the solid was washed with hexane and dried. The salt was purified by repeated recrystallization from ethanol and gave gambogic acid pyridine salt (7.5 g); HPLC: 99%.

Step C. Gambogic acid. The gambogic acid pyridine salt (0.4 g) was dissolved in ether (25 mL) and shaken with aqeuous HCl (1N, 25 mL) for 1 h. The ether solution was then washed with water (2×10 mL), dried and evaporated to give the title compound (345 mg); HPLC: 99%. $^1$H NMR (CDCl$_3$): 12.66 (s, 1H), 7.43 (d, J=6.9 Hz, 1H), 6.48 (d, J=10.2 Hz, 1H), 5.97 (t, J=7.5 Hz, 1H), 5.26 (d, J=9.9 Hz, 1H), 4.91 (m, 2H), 3.37 (m, 1H), 3.24–2.98 (m, 2H), 2.81 (d, J=6.6 Hz, 1H), 2.41 (d, J=9 Hz, 1H), 2.20 (m, J$_1$=8.4 Hz, J$_2$=5.1 HZ, 1H), 1.88 (m, 1H), 1.63 (s, 3H), 1.60 (s, 3H), 1.58 (s, 3H), 1.53 (s, 3H), 1.51 (s, 3H), 1.43 (s, 3H), 1.26 (s, 3H), 1.18 (s, 3H). MS: 627 (M-H).

Procedure 2:

The crude extract of gamboge (300 mg) was purified by repeated column chromatography (SiO$_2$, hexane-EtOAc gradient) using a Combi Flash SG 100 separation system, gave 18 mg of gambogic acid; HPLC: 94%, MS. 627 (M-H).

EXAMPLE 2

Gambogenic Acid

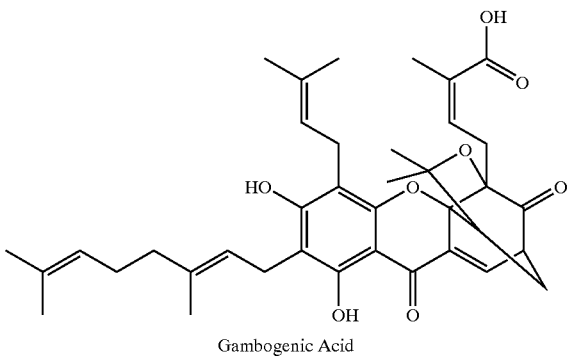

Gambogenic Acid

The crude extract of gamboge (300 mg) was purified as described in Example 1, procedure 2, to give 3 mg of gambogenic acid; HPLC: 84%, MS. 629 (M-H).

EXAMPLE 3

Gambogenin

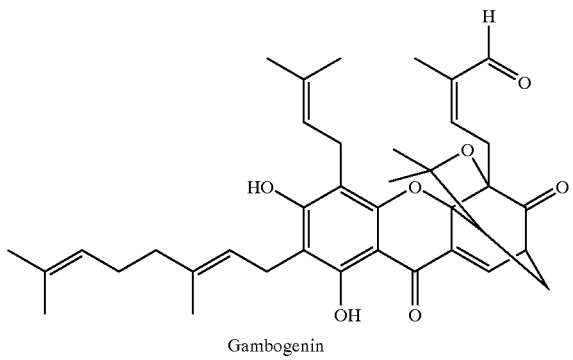

Gambogenin

The crude extract of gamboge (300 mg) was purified as described in Example 1, procedure 2, to give 2 mg of gambogenin, HPLC: 71%. MS. 613 (M-H).

EXAMPLE 4

Methyl Gambogate

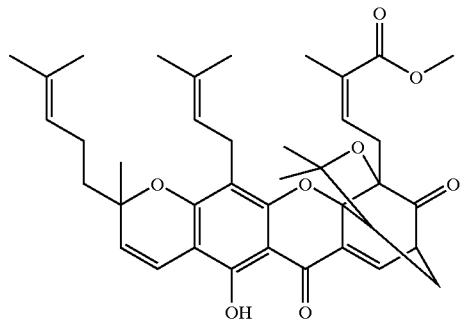

Methyl Gambogate

A mixture of gambogic acid (200 mg, 0.32 mmol), DMAP (78 mg, 0.64 mmol), EDC (123 mg, 0.64 mmol) and methanol (102 mg, 3.2 mmol) in THF (5 mL) was stirred at room temperature for 3 h. The solution was poured into water (10 mL) and was extracted with ethyl acetate (3×10 mL). The combined organic layer was dried and concentrated to give the crude product, which was purified by chromatography (SiO$_2$, EtOAc/Hexane 1:5) to give the title compound (196 mg, 95%). $^1$H NMR (CDCl$_3$): 12.85 (s, 1H), 7.54 (d, J=6.9 Hz, 1H), 6.67 (d, J=10.5 Hz, 1H), 5.94 (t, J=6 Hz, 1H), 5.43 (d, J=10.2 Hz, 1H), 5.05 (m, 2H), 3.49 (m, 1H), 3.43 (s, 3H), 3.35–3.10 (s, 2H), 3.00 (t, J=7.2 Hz, 1H), 2.52 (d, J=10.2 Hz, 1H), 2.32 (quar, J1=4.8 Hz, 1H), 2.02 (m, 1H), 1.74 (s, 3H), 1.69 (s, 3H), 1.67–1.64 (m, 9H), 1.55 (s, 3H), 1.44 (s, 3H), 1.29 (s, 3H).

EXAMPLE 5

Gambogyl Piperidine

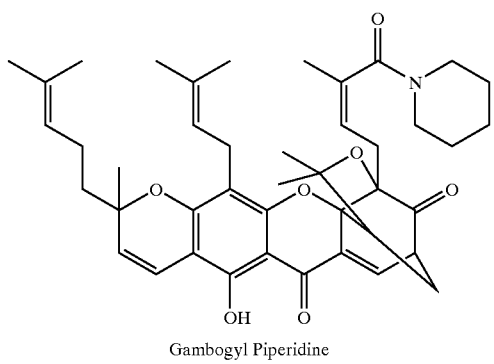

Gambogyl Piperidine

A mixture of gambogic acid (200 mg, 0.32 mmol), DMAP (39 mg, 0.32 mmol), EDC (123 mg, 0.64 mmol) and piperidine (54.2 mg, 0.64 mmol) in THF (3 mL) was stirred at room temperature for 6 h. The solution was poured into water (10 mL) and was extracted with ethyl acetate (3×10 mL). The combined organic layer was dried and concentrated to give the crude product, which was purified by chromatography (SiO$_2$, EtOAc/CH$_2$Cl$_2$ 1:8) to give the title compound (187 mg, 84%). $^1$H NMR (CDCl$_3$): 12.87 (s, 1H), 7.53 (d, J=6.9 Hz, 1H), 6.68 (d, J=10.2 Hz, 1H), 5.43 (d, J=10.5 Hz, 1H), 5.40 (t, J=6 Hz, 1H), 5.05 (m, 2H), 3.54–3.33 (m, 2H), 3.28 (d, J=6.9 Hz, 1H), 3.11 (t, J=8.4 Hz, 1H), 2.50(d, J=9.6 Hz, 1H), 2.46–2.17 (m, 3H), 2.00 (m, 1H), 1.75–1.72 (m, 5H), 1.68 (s, 2H), 1.65 (bs, 6H), 1.58 (s, 3H), 1.56 (s, 3H), 1.43 (s, 3H), 1.25 (s, 3H).

EXAMPLE 6

Methyl-6-methoxy-gambogate

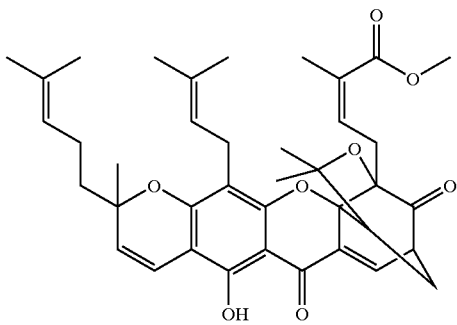

Methyl-6-methoxy-gambogate

A mixture of methyl gambogate (70 mg, 0.11 mmol), anhydrous K$_2$CO$_3$ (0.5 g), methyl iodide (1 mL) in acetone (5 mL) was stirred at room temperature for 70 h. After evaporation to near dryness, water (30 mL) was added into the mixture and it was extracted with ethyl acetate (3×10 mL). The combined organic layer was dried and concentrated to give the crude product, which was purified by chromatography (SiO$_2$, EtOAc/Hexane 1:4) to give the title compound (69 mg, 96%). MS: 657(M+H), 679 (M+Na$^+$). $^1$H NMR (CDCl$_3$): 7.41 (d, J=6.9 Hz, 1H), 6.64 (d, J=9.9 Hz, 1H), 5.93 (m, J1=6.9 Hz, J2=0.9 Hz, 1H), 5.52 (d, J=10.2 Hz, 1H), 5.05 (m, 2H), 3.79 (s, 3H), 3.40 (s, 3H), 3.45–3.18 (m, 3H), 2.95 (d, J=9.6 Hz, 1H), 2.26 (m, 1H), 2.02 (m, 1H), 1.73 (s, 3H), 1.66 (d, 3H), 1.63 (bs, 6H), 1.52 (s, 3H), 1.42 (s, 3H), 1.27(s, 3H).

EXAMPLE 7

6-Methoxy-gambogyl Piperidine

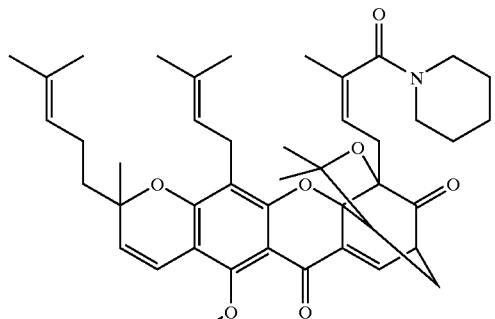

6-Methoxy-gambogyl Piperidine

The title compound was prepared by a procedure similar to that of Example 6 from gambogyl piperidine and methyl iodide. MS: 710 (M+H), 732 (M+Na$^+$). $^1$H NMR (CDCl$_3$): 7.40 (d, J=6.9 Hz, 1H), 6.64 (d, J=10.2 Hz, 1H), 5.53 (d, J=10.2 Hz, 1H), 5.34 (m, 1H), 5.09 (t, 1H), 5.04 (t, 1H), 3.80 (s, 3H), 3.52(m, 3H), 3.38–3.31 (m, 3H), 3.11 (t, 2H), 2.50–1.98 (m, 5H), 1.73 (s, 3H), 1.70 (d, 3H), 1.65 (s, 6H), 1.63 (bs, 6H), 1.53 (s, 3H), 1.42 (s, 3H), 1.22 (s, 3H).

EXAMPLE 8

10-Morpholinyl-gambogyl Morpholine

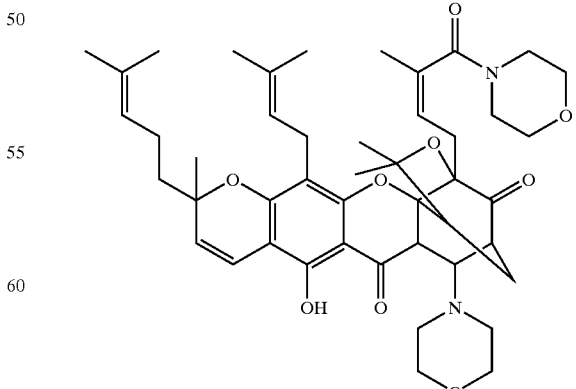

10-Morpholinyl-gambogyl Morpholine

A mixture of gambogic acid (100 mg, 0.16 mmol), DMAP (20 mg, 0.16 mmol), EDC (67.4 mg, 0.35 mmol) and morpholine (30.6 mg, 0.35 mmol) in THF (3 mL) was stirred at room temperature for 6 h. The solution was poured into water (10 mL) and was extracted with ethyl acetate (3×10 mL). The combined organic layer was dried and concentrated to give the crude product, which was purified by chromatography (SiO$_2$, EtOAc/CH$_2$Cl$_2$ 1:1) to give the title compound (87 mg, 69%). MS: 785 (M+H), 807 (M+Na$^+$). $^1$H NMR (CDCl$_3$): 11.94 (s, 1H), 6.63 (d, J=7.5 Hz, 1H), 5.96 (m, 1H), 5.43 (d, J=10.2 Hz, 1H), 5.08 (m, 2H), 3.80 (m, 1H), 3.70–3.12 (m, 12H), 2.80–2.36 (m, 7H), 2.05 (m, 1H), 1.95 (m, 1H), 1.87 (s, 3H), 1.73 (bs, 3H), 1.64 (bs, 6H), 1.55 (s, 3H), 1.45 (m, 1H), 1.32 (s, 3H), 1.28 (s, 3H), 1.24 (3H), 1.07 (s, 3H).

EXAMPLE 9

Gambogyl (4-Methylpiperazine)

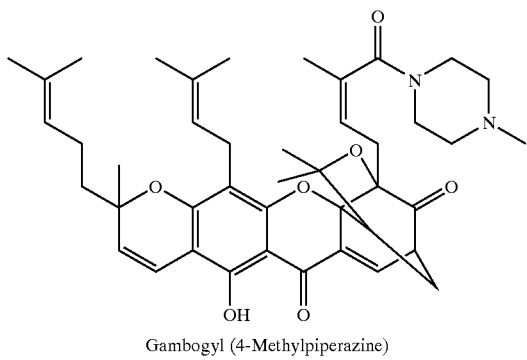

Gambogyl (4-Methylpiperazine)

A mixture of gambogic acid (93 mg, 0.15 mmol), DMAP (22 mg, 0.18 mmol), EDC (34 mg, 0.18 mmol) and N-methyl piperazine (15 mg, 0.15 mmol) in THF (5 mL) was stirred at room temperature for 5 h. The solution was poured into water (50 mL) and was extracted with ethyl acetate (3×10 mL). The combined organic layer was dried and concentrated to give crude product, which was purified by chromatography (SiO$_2$, EtOAc/MeOH 12:1) to give the title compound (35 mg, 33%). MS: 709 (M−H), 711 (M+H), 733 (M+Na$^+$). $^1$H NMR (CDCl$_3$): 12.85 (s, 1H), 7.52 (d, J=6.6 Hz, 1H), 6.66 (d, J=9.9 Hz, 1H), 5.42 (t, J=10.5 Hz, 1H), 5.05 (m, 2H), 3.62 (m, 1H), 3.40 (m, 2H), 3.28–3.17 (m, 4H), 2.50–1.98 (m, 7H), 2.23 (s, 3H), 1.72 (bs, 6H), 1.63 (bs, 6H), 1.53 (bs, 6H), 1.41 (s, 3H), 1.23 (s, 3H).

EXAMPLE 10

10-Morpholinyl-gambogyl Piperidine

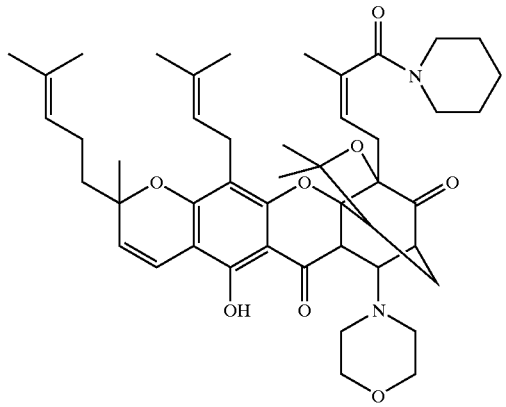

10-Morpholinyl-gambogyl Piperidine

A solution of gambogyl piperidine (50 mg, 0.071 mmol) and morpholine (0.3 mL) in THF (3 mL) was stirred for 48 h. It was evaporated and the crude product was purified through chromatography to yield the title compound (48 mg, 86%). $^1$H NMR (CDCl$_3$) 11.94 (s, 1H), 6.66 (d, J=9.9 Hz, 1H), 5.92 (t, 1H), 5.44 (d, J=10.2 Hz, 1H), 5.06 (m, 1H), 3.72–3.12 (m, 12H), 2.80 (m, 3H), 2.60–2.40 (m, 4H), 2.06 (m, 2H), 1.88 (s, 3H), 1.75 (s, 3H), 1.66 (s, 3H), 1.65 (s, 3H), 1.57 (s, 3H), 1.55 (m, 2H), 1.34 (s, 3H), 1.32 (s, 3H), 1.22 (s, 2H), 1.11 (s, 3H).

EXAMPLE 11

10-(4-Metliylpiperazinyl)-gambogyl Piperidine

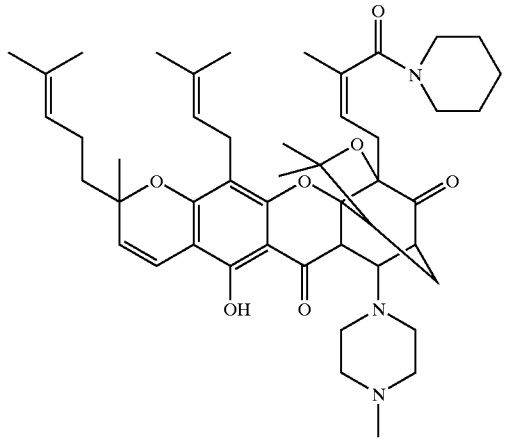

10-(4-Methylpiperazinyl)-gambogyl Piperidine

The title compound was prepared from gambogyl piperidine and N-methylpiperazine by a procedure similar to that of Example 10. MS: 797 (M+H), 819 (M+Na), 835 (M+K), 795 (M−H). $^1$H NMR (CDCl$_3$) 12.01 (s, 1H), 6.66 (d, J=9.9 Hz, 1H), 5.94 (t, 1H), 5.44 (d, J=10.2 Hz, 1H), 5.12–5.10 (m, 2H), 3.80 (d, 1H), 3.52 (d, 1H), 3.38–3.12 (m, 5H), 2.78–2.26 (m, 6H), 2.24 (s, 3H), 2.12–2.04 (m, 2H),), 1.89 (s, 3H), 1.75 (s, 3H), 1.66 (s, 6H), 1.57 (s, 3H), 1.55 (m, 2H), 1.34 (s, 3H), 1.32 (s, 3H), 1.11 (s, 3H).

EXAMPLE 12

N-(2-Gambogylamidoethyl)biotinamide

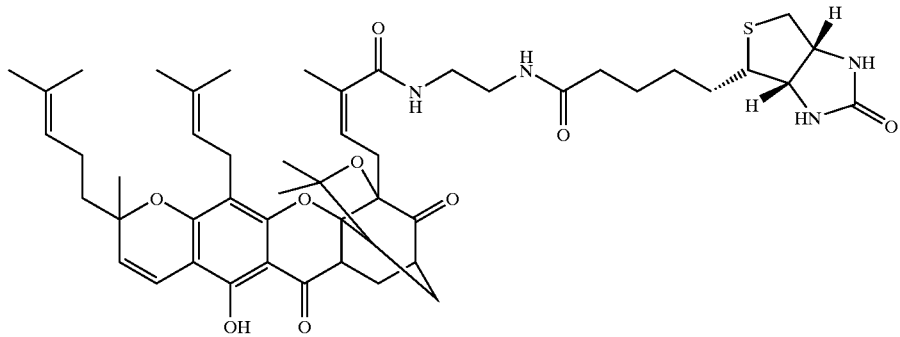

N-(2-Gambogylamidoethyl)biotinamide

The title compound was prepared by a procedure similar to that of Example 9 from gambogic acid and N-(2-aminoethyl)biotinamide. MS: 919 (M+Na), 897 (M+H), 895 (M−H). $^1$H NMR (CDCl$_3$): 12.9, 12.78 (1H), 7.60–7.57 (m, 1H), 6.90 (m, 1H), 6.78 (m, 1H), 6.70–6.62 (m, 1H), 5.48(d, J=9.9 Hz, 1H), 5.42 (m, 1H), 5.30 (m, 1H), 5.08 (m, 2H), 4.66 (s,1H), 4.49 (m, 1H), 4.33 (m, 1H), 3.58–3.40 (m, 2H), 3.38–3.10 (m, 5H), 3.16–2.88 (m, 1H), 2.80–2.52 (m, 2H), 2,40–1.92 (m, 6H), 1.78 (bs, 3H), 1.74 (bs, 2H), 1.73 (bs, 3H), 1.69 (bs, 3H), 1.65 (bs, 6H), 1.55 (bs, 3H), 1.50–1.20 (m, 13H), 1.2–0.88 (m, 4H).

EXAMPLE 13

10-(4-Methylpiperazinyl)gambogic Acid

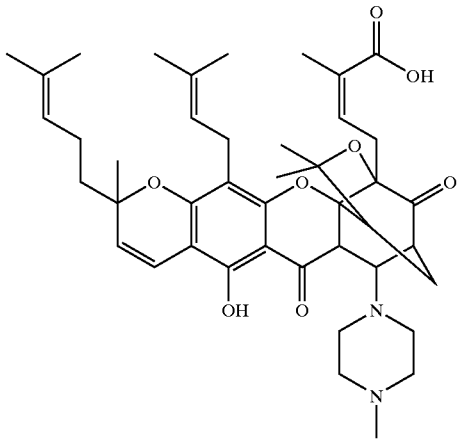

10-(4-Methylpiperazinyl)gambogic Acid

A solution of gambogic acid (35 mg, 0.056 mmol) and N-methylpiperazine (0.5 mL) in THF (4 mL) was stirred for 24 h, then another portion of N-methylpiperazine (0.5 mL) was added and stirred for 48 h. The solution was diluted with EtOAc (30 mL) and washed with aqueous NH$_4$Cl (3×30 mL). After concentration, the mixture was dissolved in ethyl ether (15 mL) and washed with 0.1 N HCl. After concentration, the residue was washed with hexane four times to gave the title compound (9 mg, 20 %). $^1$H NMR (CDCl$_3$) 11.8 (s, 1H), 6.64 (d, J=9.9 Hz, 1H), 6.57(t, 1H), 5.45 (d, J=10.5 Hz, 1H), 5.09 (t, 1H), 3.51 (bs, 1H), 3.30–2.70 (m, 11H), 2.81 (s, 3H), 2.51 (d, J=8.4 Hz, 2H), 2.12–2.02 (m, 2H), 1.96 (s, 3H), 1.73 (s, 3H), 1.66 (s, 3H), 1.63 (s, 3H), 1.56 (s, 3H), 1.35 (s, 6H), 1.26 (m, 2H), 1.11 (s, 3H), 0.88 (m, 2H).

EXAMPLE 14

10-Piperidyl-gambogyl Piperidine

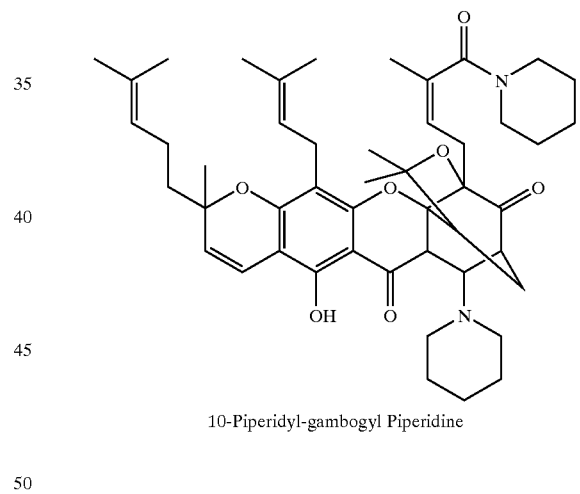

10-Piperidyl-gambogyl Piperidine

A mixture of gambogic acid (460 mg, 0.73 mmol), EDCI (166 mg, 0.87 mmol), DMAP (47 mg, 0.38 mmol) and piperidine (75 µL, 0.76 mmol) in THF (5 mL) was stirred at room temperature for 40 h. It was diluted with 1:1 hexane/EtOAc (80 mL), washed with water and brine, dried over Na$_2$SO$_4$ and concentrated in vacuo. The residue was purified by chromatography (3:2 hexane/EtOAc) to yield the title compound as a pale yellow solid (40 mg, 0.051 mmol, 7%) and gambogyl 1'-piperidine (220 mg, 0.32 mmol). $^1$H NMR (CDCl$_3$): 12.05 (s, 1H), 6.66 (d, J=10.0 Hz, 1H), 5.95 (t, J=6.3 Hz, 1H), 5.44 (d, J=10.0 Hz, 1H), 5.12–5.03 (m, 2H), 3.75–3.10 (m, 9H), 2.76–2.66 (m, 3H), 2.49 (d, J=8.4, 2H), 2.34(m, 2H), 2.08 (m, 3H), 1.89 (s, 3H), 1.75 (s, 3H), 1.66 (d, 3H), 1.61–1.23 (m, 15H), 1.33 (s, 3H), 1.31 (s, 3H), 1.27(s, 3H), 1.26 (s, 3H).

EXAMPLE 15

10-Piperidinyl-gambogic Acid

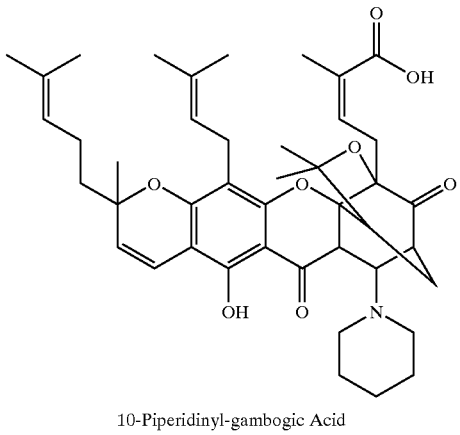

10-Piperidinyl-gambogic Acid

Gambogic acid (10 mg, 0.016 mmol) in piperidine (0.5 mL) was stirred at room temperature for 40 h. The solvent was removed in vacuo. The residue was diluted with 1:2 hexane/EtOAc (50 mL), washed with saturated ammonium chloride aqueous solution followed by brine, dried over Na$_2$SO$_4$ and concentrated in vacuo. The residue was purified by chromatography (3:2 hexane/EtOAc) to yield one of the diasteromers of the title compound (A, 3 mg, 0.004 mmol, 26%) and the other diastereomer (B, 1 mg, 0.001 mmol, 6%). $^1$H NMR (CDCl$_3$): diastereomer A: 12.00 (s, 1H), 6.66 (d, J=9.9 Hz, 1H), 6.52 (t, J=6.9 Hz, 1H), 5.46 (d, J=9.9 Hz, 1H), 5.12–5.05 (m, 2H), 3.32–3.04 (m, 6H), 2.81 (t, J=4.5, 1H), 2.55–2.43 (m, 3H), 2.33(m, 2H), 2.12–1.91 (m, 3H), 1.98 (s, 3H), 1.74 (s, 3H), 1.66 (s, 3H), 1.63 (s, 3H), 1.35 (s, 6H), 1.50–1.28 (m, 6H), 1.14 (s, 3H); diastereomer B: 12.00 (s, 1H), 7.37 (t, J=6.3 Hz, 1H), 6.66 (d, J=10.0 Hz, 1H), 5.46 (d, J=10.0 Hz, 1H), 5.12–5.02 (m, 2H), 3.35–3.18 (m, 3H), 3.11 (s, 1H), 2.91–2.79 (m, 3H), 2.56–2.48 (m, 3H), 2.33(m, 2H), 2.12–1.94 (m, 5H), 1.87 (s, 3H), 1.74 (s, 3H), 1.66 (s, 3H), 1.63 (s, 3H), 1.40 (s, 3H), 1.34 (s, 3H), 1.50–1.28 (m, 6H), 1.13 (s, 3H).

EXAMPLE 16

9,10-Dihydro-12-hydroxygambogic Acid

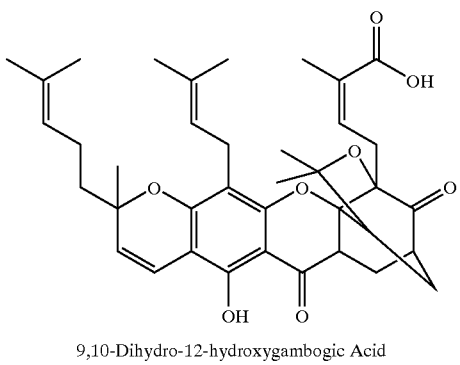

9,10-Dihydro-12-hydroxygambogic Acid

To a solution of gambogic acid (14 mg, 0.022 mmol) in methanol (2 mL) was added NaBH$_4$ (22 mg, 0.58 mmol) at 0° C. The mixture was stirred for 3 h and the cooling bath was allowed to slowly warm to room temperature. Acetone (0.5 mL) was added to the mixture and it was stirred for 30 min., acidified with 2 N HCl to pH 6, diluted with EtOAc (40 mL), washed with water (3 times) and brine, dried over Na$_2$SO$_4$ and concentrated in vacuo. The residue was purified by chromatography (9:1 EtOAc/MeOH) to give the title compound as an oil (9 mg, 0.014 mmol, 66%). $^1$H NMR (CDCl$_3$): 12.02 (s, 1H), 6.66 (d, J=10.2 Hz, 1H), 6.33 (t, J=7.2, 1H), 5.45 (d, J=10.2 Hz, 1H), 5.12–5.05 (m, 2H), 3.71 (s, 1H), 3.26–3.11 (m, 3H), 3.02–2.94 (m, 2H), 2.56–2.49 (m, 1H), 2.36 (d, J=9.6, 1H), 2.12–2.04 (m, 3H), 1.99 (s, 3H), 1.76 (m, 1H), 1.73 (s, 3H), 1.66 (s, 3H), 1.63 (s, 3H), 1.60–1.30 (m, 5H), 1.42 (s, 3H), 1.39 (s, 3H), 1.35 (s, 3H).

EXAMPLE 17

Methyl-10-Morpholinyl-gambogate

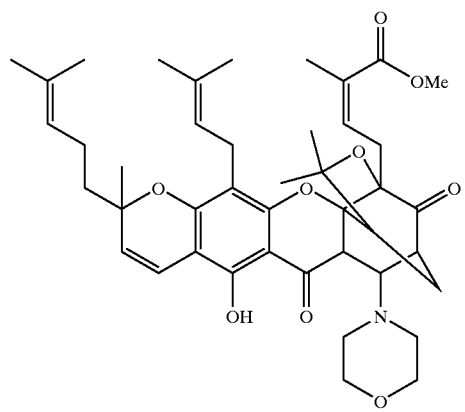

Methyl-10-Morpholinyl-gambogate

To a solution of methyl gambogate (50 mg, 0.078 mmol) in THF (2 mL) was added morpholine (70 L, 0.80 mmol). The mixture was stirred at room temperature for 17 h, diluted with 1:1 hexane/EtOAc (100 mL), washed with water (3 times) and brine, dried over Na$_2$SO$_4$ and concentrated in vacuo to yield the title compound as light yellow solid (52 mg, 0.071 mmol, 91%). $^1$H NMR (CDCl$_3$): 11.98 (s, 1H), 6.66 (d, J=10.2 Hz, 1H), 6.62 (t, J=6.6 Hz, 1H), 5.46 (d, J=10.2 Hz, 1H), 5.12–5.00 (m, 2H), 3.68 (s, 3H), 3.74–3.55 (m, 4H), 3.43–3.14 (m, 6H), 2.77 (m, 1H), 2.59–2.40 (m, 5H), 2.07(m, 1H), 1.95 (s, 3H), 1.74 (s, 3H), 1.66 (s, 3H), 1.63 (s, 3H), 1.36 (s, 3H), 1.35 (s, 3H), 1.14 (s, 3H).

EXAMPLE 18

Isogambogic Acid

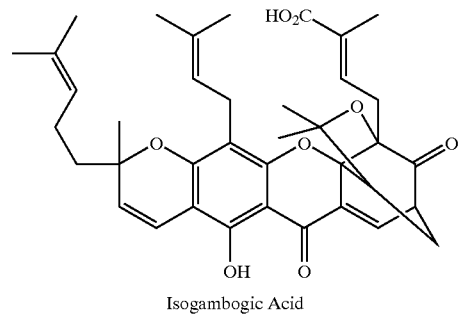

Isogambogic Acid

The crude extract of gamboge (300 mg) was purified as described in Example 1, procedure 2, to give 2 mg of isogambogic acid; MS. 627 (M–H).

EXAMPLE 19

Morellic Acid

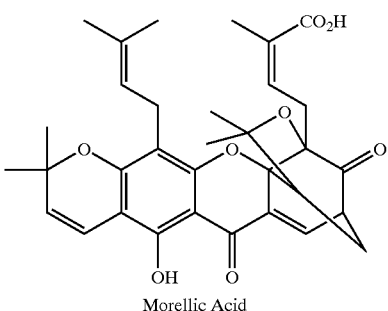

Morellic Acid

The crude extract of gamboge (300 mg) was purified as described in Example 1, procedure 2, to give 2 mg of morellic acid; MS. 559 (M−H).

EXAMPLE 20

10-Cyclohexylgambogic Acid

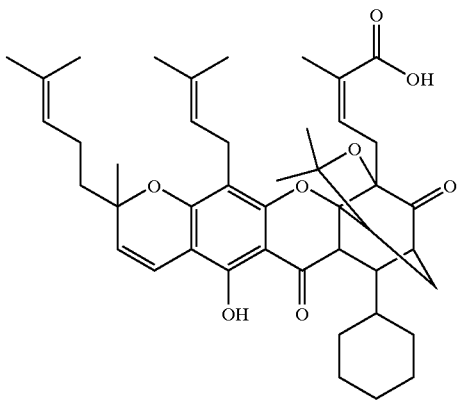

10-Cyclohexylgambogic Acid

To a solution of gambogic acid (80 mg, 0.13 mmol) in THF (5 mL) was added a solution of cyclohexylcuprate (1.2 mmol) in THF prepared from cyclohexylmagnesium chloride and CuI at 0° C. The mixture was stirred for 2 h and the cooling bath was allowed to slowly warm to room temperature. The reaction was quenched with 2 N HCl and diluted with 1:1 hexane/EtOAc (80 mL). The resulting mixture was washed with water and brine, dried over $Na_2SO_4$ and concentrated in vacuo. The residue was purified by chromatography (3:1 hexane/EtOAc) to give the title compound as an oily solid (9 mg, 0.013 mmol, 10%). $^1$H NMR (CDCl$_3$): 6.61 (d, J=10.2, 1H), 6.14 (t, J=6.0, 1H), 5.39 (d, J=10.2, 1H), 5.20 (t, J=6.6, 1H), 5.06 (t, J=7.2, 1H), 3.64 (m, 1H), 3.35–3.10 (m, 3H), 2.82 (br s, 2H), 2.67–2.61 (m, 2H), 1.76(s, 3H), 1.72 (s, 3H), 1.68 (s, 3H), 1.66 (s, 3H), 1.56 (s, 3H), 1.44 (s, 3H), 1.94–1.25 (m, 15H).

EXAMPLE 21

10-Methylgambogic Acid

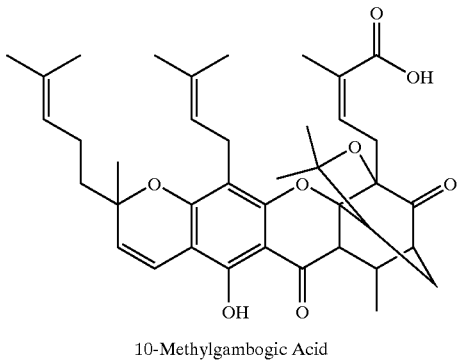

10-Methylgambogic Acid

The title compound was prepared by a procedure similar to that of Example 20 from gambogic acid and methylcuprate and was isolated as an oil. $^1$H NMR (CDCl$_3$): 6.58 (d, J=10.2, 1H), 6.12 (t, J=6.6, 1H), 5.36 (d, J=9.9, 1H), 5.15 (t, J=6.6, 1H), 5.04 (t, J=7.2, 1H), 3.32–3.10 (m, 2H), 2.93 (d, J=8.4, 1H), 2.84 (d, J=6.3, 2H), 2.62 (d, J=7.6, 1H), 2.40 (t, J=7.2, 1H), 2.25 (d, J=4.8, 1H), 2.08–1.92 (m, 4H), 1.73(s, 3H), 1.68 (s, 3H), 1.66 (s, 6H), 1.64 (s, 3H), 1.54 (s, 3H), 1.41 (s, 3H), 1.35 (d, J=6.9, 3H), 1.23 (s, 1H).

EXAMPLE 22

9,10-Dihydrogambogic Acid

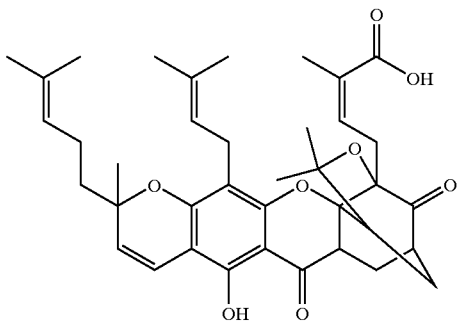

9,10-Dihydrogambogic Acid

To a solution of gambogic acid (17 mg, 0.027 mmol) in methylenechloride (2 mL) was added L-selectride solution in THF (1.0 mL, 0.5 mmol) dropwise at −78° C. After 30 min of stirring, the reaction was quenched with 1 mL of 2 N HCl. The mixture was then allowed to warm to room temperature and was diluted with 1:1 hexane/EtOAc (50 mL). The resulting mixture was washed with water and brine, dried over $Na_2SO_4$ and concentrated in vacuo. The residue was purified by chromatography (2:3 hexane/EtOAc/) to give the title compound as an oil (0.6 mg, 0.001 mmol, 4%). $^1$H NMR (CDCl$_3$): 11.96 (s, 1H), 6.67 (d, J=10.2, 1H), 6.54 (t, J=6.6, 1H), 5.46 (d, J=10.2, 1H), 5.13–5.05 (m, 2H), 3.33–3.16 (m, 3H), 2.85 (d, J=13.8, 1H), 2.60 (d, J=8.7, 1H), 2.43 (s, 1H), 2.08 (m, 1H), 1.97 (s, 3H), 1.74 (s, 3H), 1.67 (s, 6H), 1.64 (s, 3H), 1.57 (s, 3H), 1.37 (s, 3H), 1.36 (d, J=6.9, 3H), 1.31–1.22 (m, 5H), 1.14 (s, 3H).

EXAMPLE 23

Gambogyl (2-(4-Morpholinyl)ethylamine)

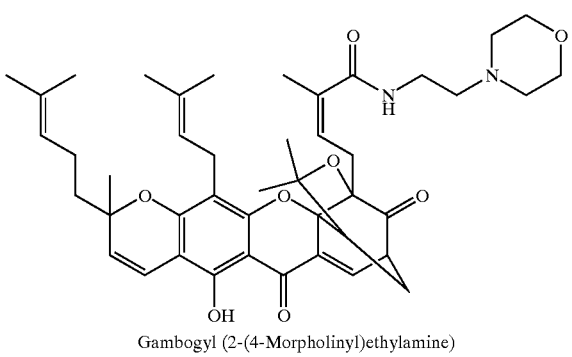

Gambogyl (2-(4-Morpholinyl)ethylamine)

The title compound was prepared as described in Example 5 from gambogic acid and 2-(4-morpholinyl)ethylamine and isolated as a yellow solid (75 mg, 0.10 mmol, 56%). $^1$H NMR (CDCl$_3$): 12.86 (s, 1H), 7.54 (d, J=6.6, 1H), 6.68 (d, J=10.2, 1H), 6.56 (t, J=5.1, 1H), 5.46 (d, J=10.2, 1H), 5.28 (d, J=7.5, 1H), 5.05 (br s, 1H), 3.68 (t, J=4.2, 4H), 3.47 (m, 1H), 3.71–3.17 (m, 4H), 2.68 (t, J=6.6, 2H), 2.54 (d, J=9.6, 1H), 2.48–2.44 (m, 6H), 2.36–2.30 (m, 1H), 2.01–2.00 (m, 3H), 1.74 (s, 6H), 1.67 (s, 3H), 1.65 (s, 6H), 1.61 (s, 3H), 1.44 (s, 3H), 1.28 (s, 3H).

EXAMPLE 24

9,10-Epoxygambogic Acid

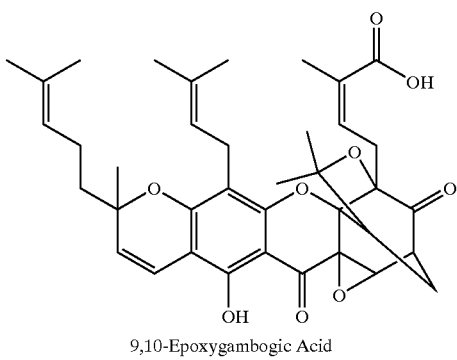

9,10-Epoxygambogic Acid

To a solution of gambogic acid (52 mg, 0.08 mmol) in methanol (2 mL) was added 2 N NaOH (0.5 mL, 1.0 mmol), followed by 35% H$_2$O$_2$. (0.2 mL, 2.1 mmol) at room temperature. The mixture was stirred at room temperature for 10 min, diluted with 1:1 hexane/EtOAc (50 mL), washed with water, 2 N HCl and brine, dried over Na$_2$SO$_4$ and concentrated in vacuo. The residue was purified by chromatography (1:2 hexane/EtOAc) to yield the title compound as an oil (2.2 mg, 0.003 mmol, 4%). $^1$H NMR (CDCl$_3$): 11.92 (s, 1H), 6.66 (d, J=10.2, 1H), 6.51 (t, J=6.9, 1H), 5.46 (d, J=9.9, 1H), 5.09–5.04 (m, 2H), 4.35 (d, J=3.9, 1H), 3.32 (s, 2H), 3.27–2.99 (m, 4H), 2.85 (t, J=4.8, 1H), 2.51 (d, J=8.7, 1H), 2.07 (m, 1H), 1.97 (s, 3H), 1.74 (s, 3H), 1.66 (s, 3H), 1.63 (s, 3H), 1.56 (s, 3H), 1.36 (s, 3H), 1.15 (s, 3H).

EXAMPLE 25

Gambogyl (4-(2-Pyridyl)piperazine) and 10-[4-(2-Pyridyl)piperazinyl]gambogyl(4-(2-Pyridyl)piperazine)

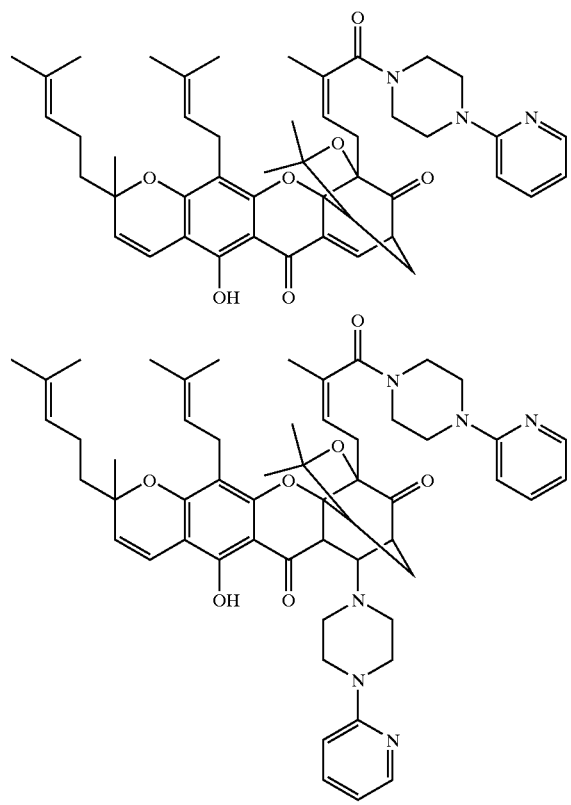

Gambogyl (4-(2-Pyridyl)piperazine) and 10-[4-(2-Pyridyl)piperazinyl]gambogy[(4-(2-Pyridyl)piperazine)

A mixture of gambogic acid (230 mg, 0.37 mmol), 1-(2-pyridyl)piperazine (75 μL, 0.46 mmol), and EDC (77 mg, 0.40 mmol) in DMF (3 mL) was stirred at room temperature, overnight. The mixture was diluted with 1:1 hexane/EtOAc (90 mL), washed with water and brine, dried over Na$_2$SO$_4$ and concentrated in vacuo. The residue was purified by chromatography (3:2 hexane/EtOAc) to yield 10 mg of gambogyl (4-(2-pyridyl)piperazine) as a yellow solid. $^1$H NMR (CDCl$_3$): 12.87 (s, 1H), 8.19 (m, 1H), 7.52 (d, J=6.9, 1H), 6.68–6.62 (m, 2H), 6.43 (d, J=9.9, 1H), 5.06 (br s, 2H), 3.76–3.27 (m, 11H), 2.52–2.00 (m, 6H), 1.76 (s, 3H), 1.26 (s, 3H); 1.73 (s, 3H), 1.68 (s, 3H), 1.65 (s, 6H), 1.56 (s, 3H), 1.42 (s, 3H), 1.26 (s, 3H); and 31 mg of 10-[4-(2-pyridyl)piperazinyl]gambogyl(4-(2-pyridyl)piperazine) as a yellow solid. $^1$H NMR (CDCl$_3$): 11.99 (s, 1H), 8.17 (d, J=4.8, 2H), 7.45 (t, J=7.5, 2H), 6.68–6.52 (m, 5H), 6.00 (t, J=6.6, 1H), 5.44 (d, J=10.2, 1H), 5.11–5.07 (m, 2H), 3.90–3.13 (m, 15H), 2.83–2.51 (m, 8H), 2.07 (m, 2H), 1.90 (s, 3H), 1.73 (s, 3H), 1.65 (s, 6H), 1.57 (s, 3H), 1.35 (s, 3H), 1.32 (s, 3H), 1.12 (s, 3H);

EXAMPLE 26

6-Acetyl-gambogic Acid

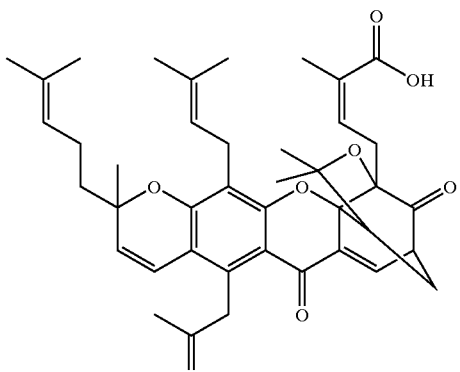

6-Acetyl-gambogic Acid

A mixture of gambogic acid (154 mg, 0.24 mmol) and Ac$_2$O (0.3 mL, 3.2 mmol) in pyridine (3 mL) was stirred at room temperature for four days. The mixture was diluted with 1:1 hexane/EtOAc (80 mL), washed with water, 2 N HCl and brine, dried over Na$_2$SO$_4$ and concentrated in vacuo. The residue was purified by chromatography (1:2 hexane/EtOAc) to yield the title compound as a yellow solid (47 mg, 0.07 mmol, 29%). $^1$H NMR (CDCl$_3$): 7.44 (d, J=6.9, 1H), 6.66 (t, J=6.6, 1H), 6.40 (d, J=10.2, 1H), 5.60 (d, J=10.5, 1H), 5.13 (t, J=6.9, 1H), 5.04 (t, J=6.9, 1H), 3.46 (m, 1H), 3.34 (d, J=6.9, 1H), 2.67–2.50 (m, 3H), 2.39 (s, 3H), 2.33–2.27 (m, 1H), 2.08–1.98 (m, 2H), 1.73 (s, 3H), 1.71 (s, 3H), 1.65 (s, 6H), 1.54 (s, 3H), 1.40 (s, 3H), 1.6 (s, 3H), 1.29 (s, 3H).

EXAMPLE 27

10-[4-(2-Pyridyl)piperazinyl]gambogic Acid

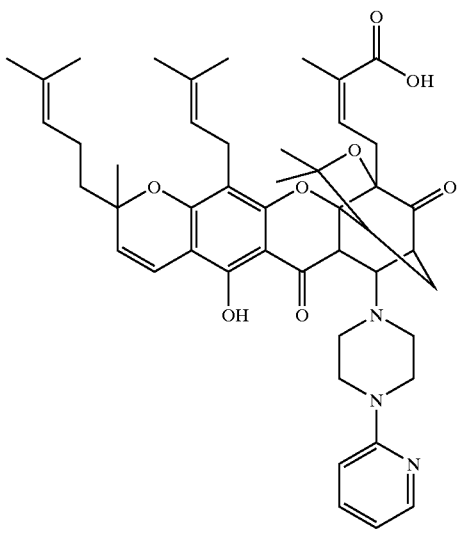

10-[4-(2-Pyridyl)piperazinyl]gambogic Acid

A mixture of pyridinium gambogate (228 mg, 0.32 mmol) and 1-(2-pyridyl)piperazine (289 mg, 1.8 mmol) in THF (3 mL) was stirred at room temperature, overnight. The mixture was diluted with 1:1 hexane/EtOAc (80 mL), washed with water, 2 N HCl and brine, dried over Na$_2$SO$_4$ and concentrated in vacuo to yield the title compound as a yellow solid (143 mg, 0.16 mmol, 50%). $^1$H NMR (CDCl$_3$): 11.97 (s, 1H), 8.15 (m, 1H), 7.45 (m, 1H), 6.68–6.54 (m, 4H), 5.46 (d, J=9.9, 1H), 4.12–5.02 (m, 2H), 3.40–3.08 (m, 10H), 2.83 (t, J=4.5, 1H), 2.71–2.67 (m, 2H), 2.57–2.52 (m, 3H), 1.95 (s, 3H), 1.74 (s, 3H), 1.66(s, 3H), 1.63 (s, 3H), 1.57 (s, 3H), 1.37 (s, 6H), 1.16 (s, 3H).

EXAMPLE 28

N-Hydroxysuccinimidyl Gambogate

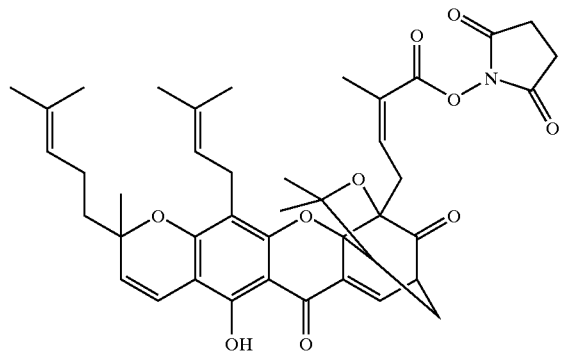

N-Hydroxysuccinimidyl Gambogate

A mixture of gambogic acid (600 mg, 0.96 mmol), N-hydroxysuccinimide (221 mg, 1.92 mmol), DCC (296.6 mg, 1.44 mmol) in dichloromethane (20 mL) was stirred for 2 h. It was evaporated to dryness and the residue was dissolved in ethyl acetate (50 mL) and washed with water (50 mL×3). The organic layer was dried and concentrated to give crude product, which was purified by flash column chromatography (SiO$_2$, EtOAc/hexane 1:3) to give the title compound (530 mg, 76%). $^1$H NMR (CDCl$_3$): 12.85 (s, 1H), 7.55 (d, J=6.9 Hz, 1H), 6.67 (d, J=10.2 Hz, 1H), 6.62 (t, J=6.9 Hz, 1H), 5.44 (d, J=9.9 Hz, 1H), 5.06 (m, 2H), 3.46 (m, 1H), 3.38–3.12 (m, 2H), 2.84–2.76 (m, 4H), 2.54 (d, 1H), 2.30 (m, 1H), 2.04 (m, 1H), 1.94 (s, 3H), 1.74(s, 3H), 1.72 (s, 3H), 1.66 (s, 3H), 1.63 (s, 3H), 1.56 (s, 3H), (bs, 6H), 1.43 (s, 3H), 1.29 (s, 3H).

EXAMPLE 29

8-(Gambogylamido)octanoic Acid

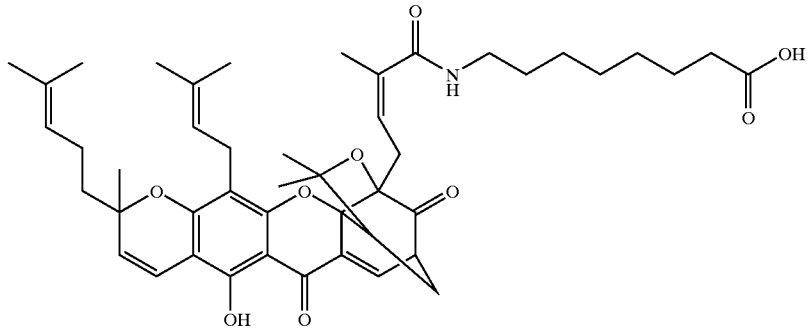

8-(Gambogylamido)octanoic Acid

A solution of 8-aminooctanoic acid (3.07 mg, 0.019 mmol), N-hydroxysuccinimidyl gambogate (14 mg, 0.019 mmol), triethylamine (0.15 mL) in anhydrous DMSO (3 mL) was stirred overnight. It was diluted with water and extracted with ethyl acetate (3×10 mL). The combined organic layer was dried and concentrated to give crude product, which was purified by column chromatography (SiO$_2$, EtOAc/MeOH 10:1) to give the title compound (11 mg, 67%). $^1$H NMR (CDCl$_3$): 12.80 (bs, 1H), 7.58 (bs, 1H), 6.64 (d, J=9.3 Hz, 1H), 5.50–5.00 (m, 4H), 3.54 (bs, 1H), 3.32–3.00 (m, 3H), 3.50–2.42 (m, 4H), 1.75 (s, 3H), 1.72 (s, 3H), 1.70 (s, 3H). MS. 792 (M+Na$^+$), 768 (M−H).

EXAMPLE 30

6-(Gambogylamido)hexanoic Acid

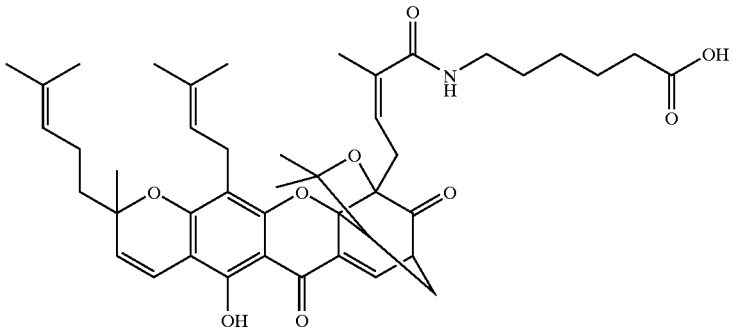

6-(Gambogylamido)hexanoic Acid

The title compound was prepared by a procedure similar to that of Example 29. $^1$H NMR (CDCl$_3$): 12.70 (bs, 1H), 7.58 (bs, 1H), 6.62 (bs, 1H), 5.40 (bs, 1H), 5.20 (bs, 1H), 5.00 (bs, 2H), 3.60–3.00 (m, 4H), 3.50–2.42 (m, 4H), 1.74 (s, 3H), 1.72 (s, 3H), 1.69 (s, 3H). MS. 764 (M+Na$^+$), 740 (M−H).

EXAMPLE 31

12-(Gambogylamido)dodecanoic Acid

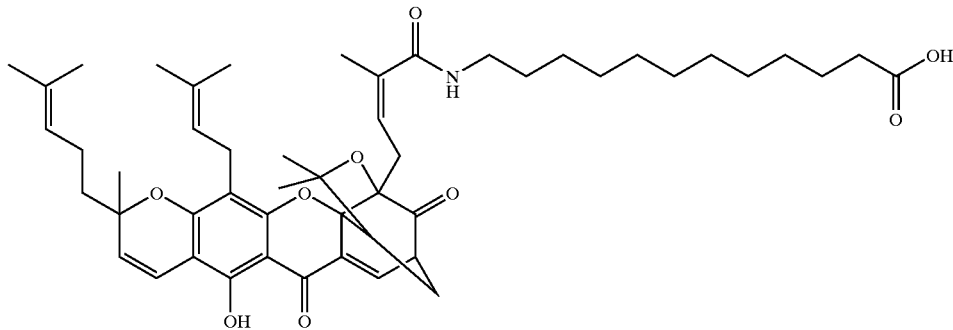

12-(Gambogylamido)dodecanoic Acid

The title compound was prepared by a procedure similar to that of Example 29. $^1$H NMR (CDCl$_3$): 12.7 (bs, 1H), 7.48 (d, 1H), 6.64 (d, J=10.5 Hz, 1H), 5.50–5.00 (m, 6H), 3.50 (bs, 1H), 3.40–3.00 (m, 3H), 2.80–1.92 (m, 6H). 1.75 (s, 3H), 1.73 (s, 3H), 1.71 (s, 3H), 1.56 (s, 3H). MS. 849 (M+Na$^+$), 825 (M−1).

EXAMPLE 32

N-Hydroxysuccinimidyl-8-(Gambogylamido)octanoate

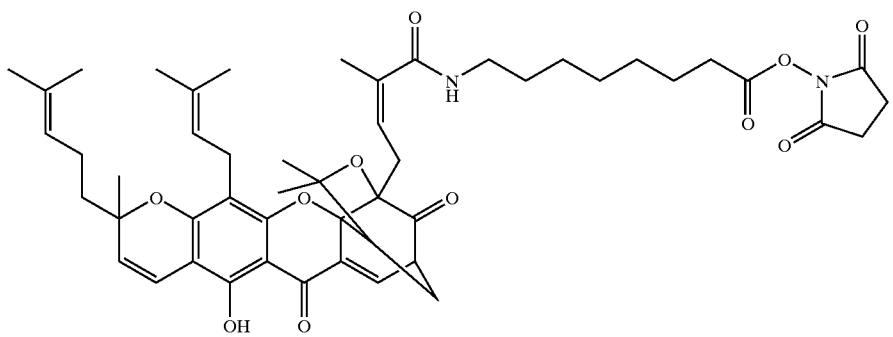

N-Hydroxysuccinimidyl-8-(Gambogylamido)octanoate

The title compound was prepared by a procedure similar to that of Example 28. $^1$H NMR (CDCl$_3$): 12.70 (s, 1H), 7.55 and 7.51 (d, J=6.9 Hz, 1H), 6.65 and 6.64 (d, J=10.2 Hz, 1H), 5.50–5.00 (m, 4H), 4.12 (d, 2H), 3.49 (m, 2H), 3.30 (t, J=6.6 Hz, 1H), 3.19 (m, 3H), 2.85 (s, 4H), 2.70–2.50 (m, 3H), 2.04 (m, 1H), 1.75 (bs, 3H), 1.74(s, 3H), 1.72 (s, 3H), 1.70 (s, 3H), 1.56 (s, 3H), 1.42 (s, 3H), 1.33 (bs, 3H), 1.30 (bs, 3H). MS. 889 (M+Na$^+$), 865 (M−H).

EXAMPLE 33

N-Hydroxysuccinimidyl-6-(Gambogylamido)hexanoate

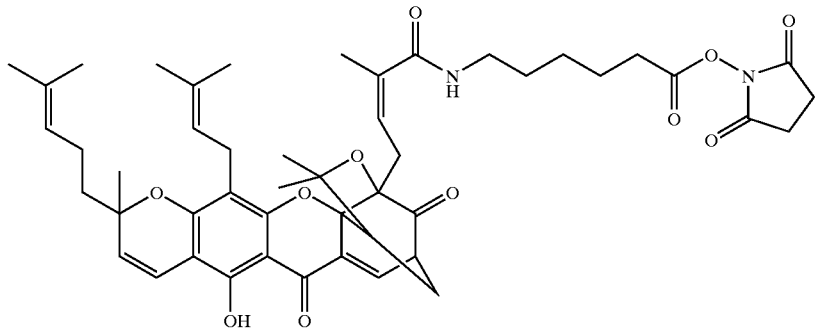

N-Hydroxysuccinimidyl-6-(Gambogylamido)hexanoate

The title compound was prepared by a procedure similar to that of Example 28. $^1$H NMR (CDCl$_3$): 12.70 (s, 1H), 7.56 and 7.52 (d, J=6.9 Hz, 1H), 6.69 and 6.65(d, J=10.2 Hz, 1H), 6.59 (t, 1H), 5.60–5.00 (m, 4H), 4.10 (m, 2H), 3.60–3.12 (m, 6H), 2.85 (s, 4H), 2.70–2.50 (m, 3H), 2.35 (m, 1H), 2.04 (m, 1H), 1.90 (m, 4H), 1.73(s, 3H), 1.72 (s, 3H), 1.69 (s, 3H), 1.56 (bs, 6H), 1.44(s, 3H), 1.33(s, 3H), 1.29(s, 3H). MS. 861 (M+Na$^+$), 837 (M–H).

EXAMPLE 34

N-Hydroxysuccinimidyl-12-(Gambogylamido)dodecanoate

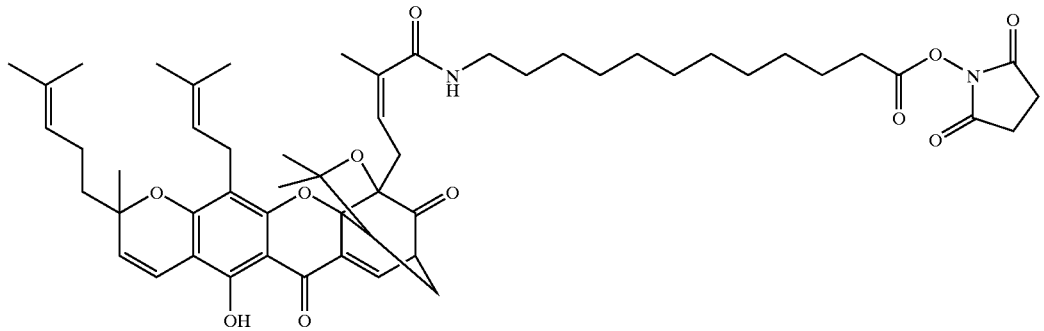

N-Hydroxysuccinimidyl-12-(Gambogylamido)dodecanoate

The title compound was prepared by a procedure similar to that of Example 28. $^1$H NMR (CDCl$_3$): 12.70 (s, 1H), 7.55 and 7.51 (d, J=7.2 Hz, 1H), 6.66 and 6.64(d, J=9.9 Hz, 1H), 5.47(d, J=10.5 Hz, 1H), 5.46–5.10 (m, 3H), 4.08 (m, 4H), 3.56–3.40 (m, 4H), 3.18 (m, 2H), 2.60 (t, 1H), 2.83 (s, 4H). MS. 946 (M+Na$^+$), 922 (M–H).

EXAMPLE 35

10-Methoxy-gambogyl Piperidine

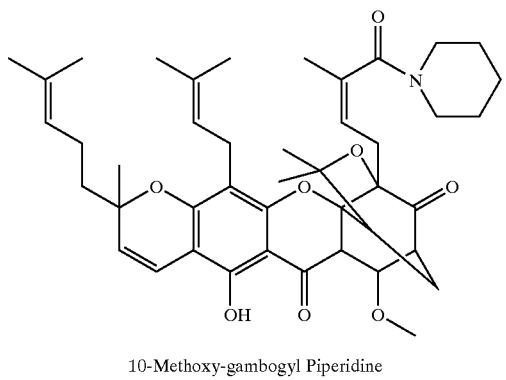

10-Methoxy-gambogyl Piperidine

To a solution of gambogyl piperidine (30 mg, 0.043 mmol) in methanol (4 mL) was added sodium methoxide (4.6 mg, 0.086 mmol) and it was stirred at room temperature for 3 h. The reaction was poured into ice water (20 mL), and extracted with ethyl acetate (3×10 mL). The organic extract was dried and concentrated to give crude product, which was purified by chromatography to give the title compound (18 mg, 58%). MS. 726 (M–H$^+$), 750 (M+Na$^+$). $^1$H NMR (CDCl$_3$): 11.98 (s, 1H), 6.65 (d, J=10.2 Hz, 1H), 5.77 (t, J=6.6 Hz, 1H), 5.43 (d, J=10.2 Hz, 1H), 5.07 (m, 2H), 4.33 (d, 1H), 3.60–3.15 (m, 3H), 3.31 (s, 3H), 2.80–2.40 (m, 3H), 1.87 (s, 3H), 1.66 (s, 3H), 1.60 (s, 3H), 1.36 (s, 3H), 1.31 (s, 3H), 1.28 (s, 3H), 1.23 (s, 3H), 1.11 (s, 3H).

EXAMPLE 36

Gambogyl (2-Dimethylaminoethylamine)

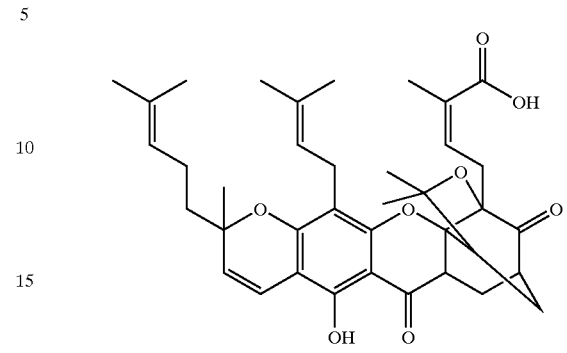

The title compound was prepared by a procedure similar to that of Example 29. MS. 697 (M–H$^-$), 699 (M+H$^+$). $^1$H NMR (CDCl$_3$): 12.90 (bs, 1H), 7.54 (d, J=6.9 Hz, 1H), 6.68 (d, J=9.6 Hz, 1H), 6.52 (t, 1H), 5.45 (d, J=10.2 Hz, 1H), 5.37 (dt, J$_1$=8.4 Hz, J$_2$=1.5 Hz, 1H), 5.05 (m, 2H), 3.50–3.10 (m, 3H), 2.21 (s, 6H), 1.76 (s, 3H), 1.75 (s, 3H), 1.69 (s, 3H), 1.65 (s, 3H), 1.64 (s, 3H), 1.56 (s, 3H), 1.44 (s, 3H), 1.29 (s, 3H).

The following compounds (Examples 37–89) were prepared by a procedure similar to that of Example 9.

TABLE I

Examples 37–89

| Example # | STRUCTURE | MF | MW |
|---|---|---|---|
| 37 | 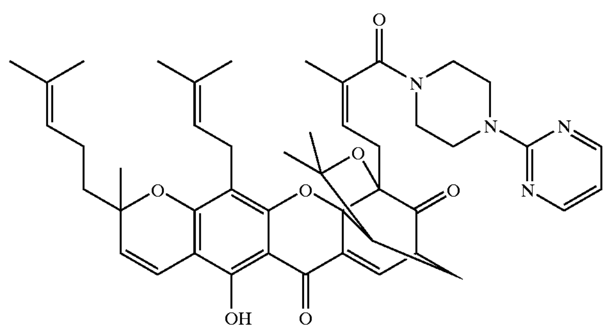 | C$_{46}$H$_{54}$N$_4$O$_7$ | 774.954 |
| 38 | 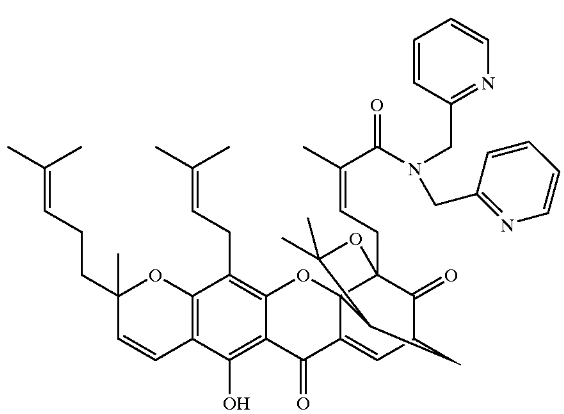 | C$_{50}$H$_{55}$N$_3$O$_7$ | 809.998 |

TABLE I-continued

Examples 37–89

| Example # | STRUCTURE | MF | MW |
|---|---|---|---|
| 39 | 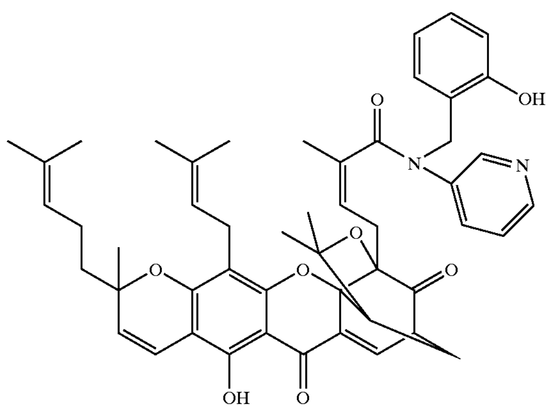 | $C_{50}H_{54}N_2O_8$ | 810.983 |
| 40 | 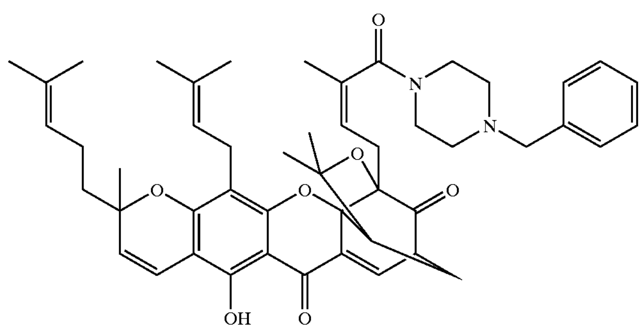 | $C_{49}H_{58}N_2O_7$ | 787.004 |
| 41 | 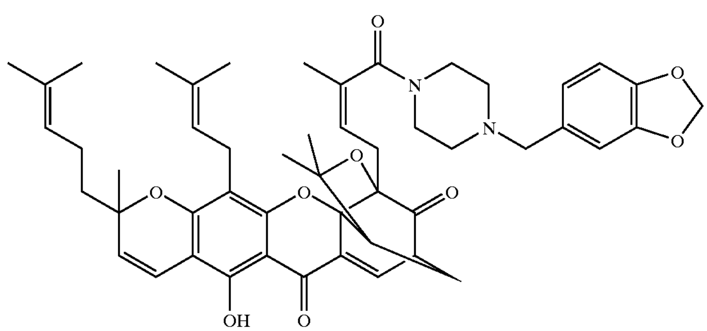 | $C_{50}H_{58}N_2O_9$ | 831.013 |
| 42 | 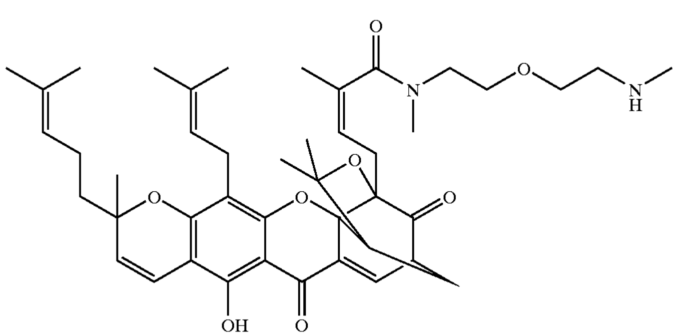 | $C_{44}H_{58}N_2O_8$ | 742.948 |

TABLE I-continued

Examples 37–89

| Example # | STRUCTURE | MF | MW |
|---|---|---|---|
| 43 | 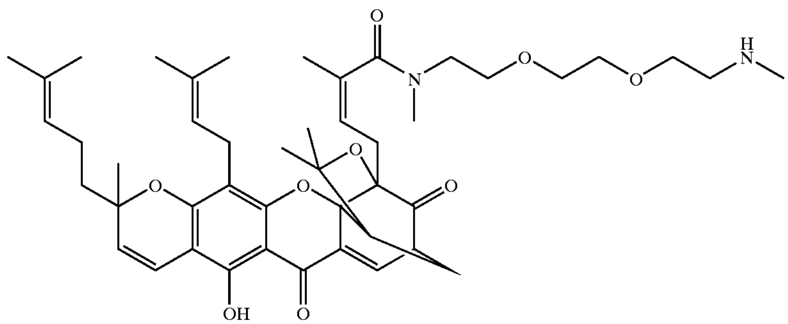 | $C_{46}H_{62}N_2O_9$ | 787.001 |
| 44 | 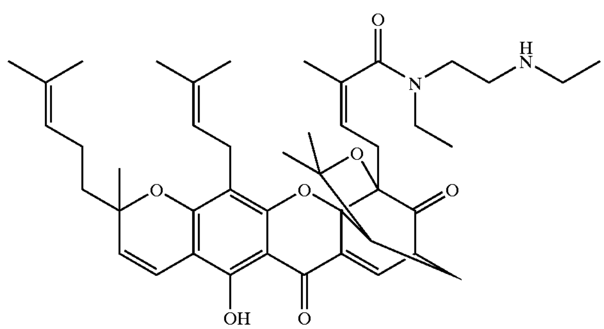 | $C_{44}H_{58}N_2O_7$ | 726.949 |
| 45 | 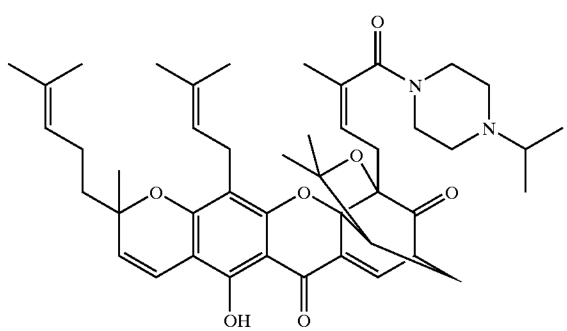 | $C_{45}H_{58}N_2O_7$ | 738.96 |
| 46 | 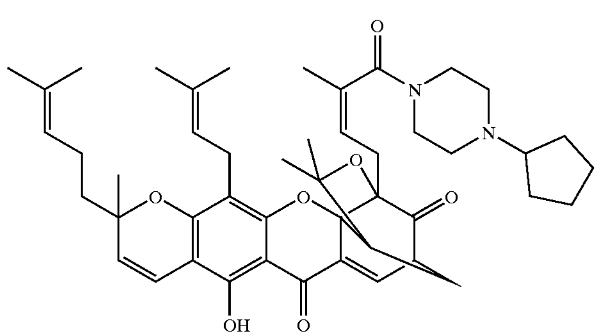 | $C_{47}H_{60}N_2O_7$ | 764.998 |

TABLE I-continued

Examples 37–89

| Example # | STRUCTURE | MF | MW |
|---|---|---|---|
| 47 | 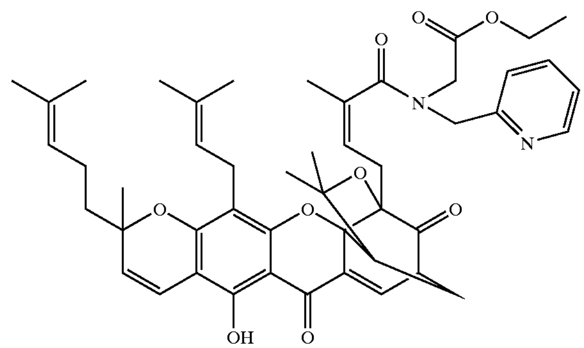 | $C_{48}H_{56}N_2O_9$ | 804.975 |
| 48 | 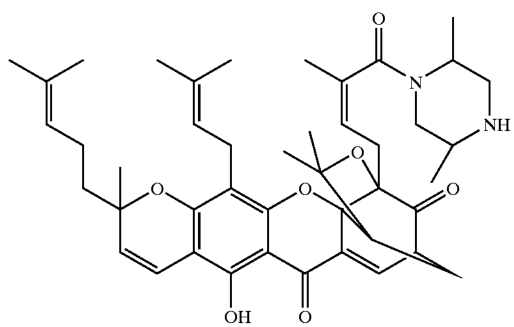 | $C_{44}H_{56}N_2O_7$ | 724.933 |
| 49 | 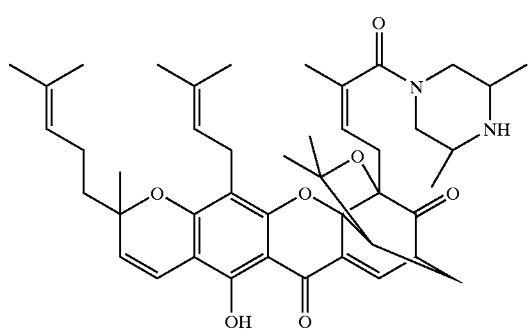 | $C_{44}H_{56}N_2O_7$ | 724.933 |
| 50 | 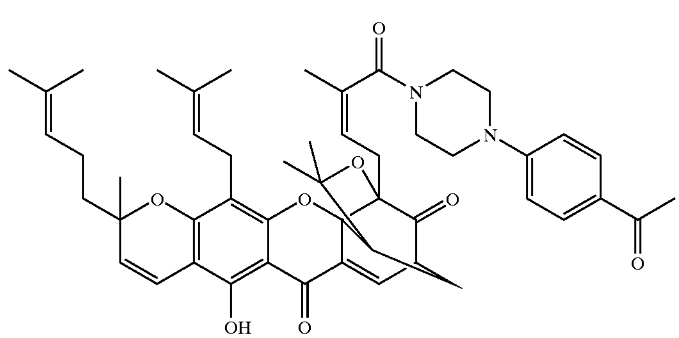 | $C_{50}H_{58}N_2O_8$ | 815.014 |

TABLE I-continued
Examples 37–89
| Example # | STRUCTURE | MF | MW |
|---|---|---|---|
| 51 | 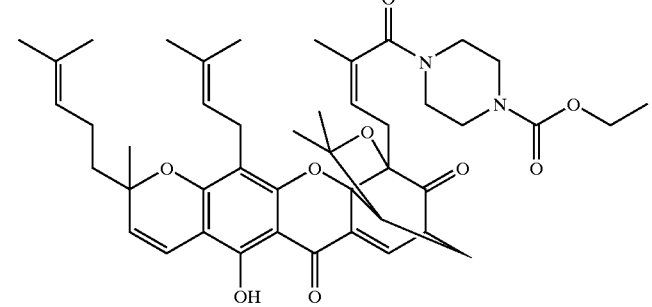 | $C_{45}H_{56}N_2O_9$ | 768.942 |
| 52 | 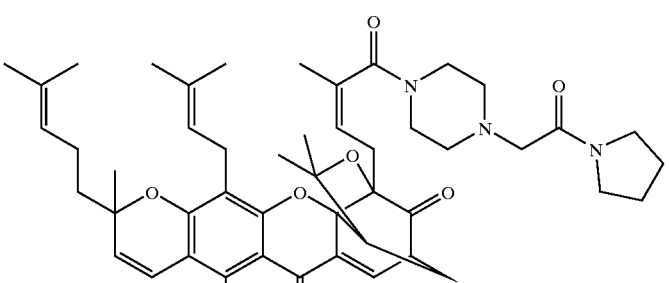 | $C_{48}H_{61}N_3O_8$ | 808.023 |
| 53 | 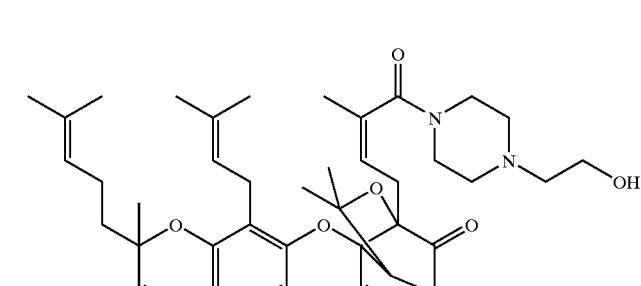 | $C_{44}H_{56}N_2O_8$ | 740.932 |
| 54 | 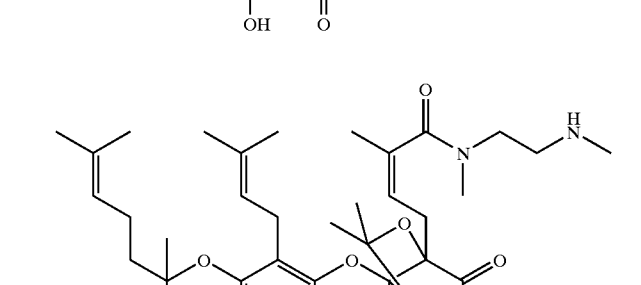 | $C_{42}H_{54}N_2O_7$ | 698.896 |

TABLE I-continued

Examples 37–89

| Example # | STRUCTURE | MF | MW |
|---|---|---|---|
| 55 | 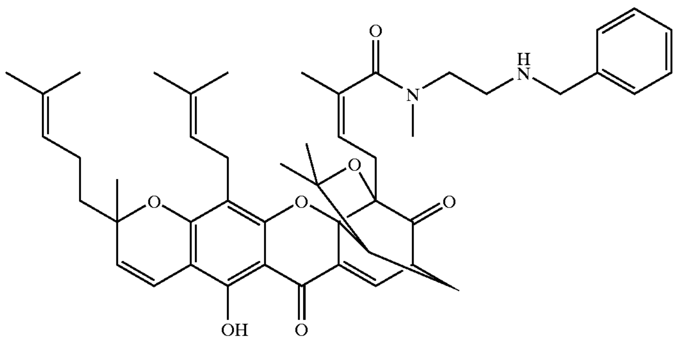 | $C_{48}H_{58}N_2O_7$ | 774.993 |
| 56 | 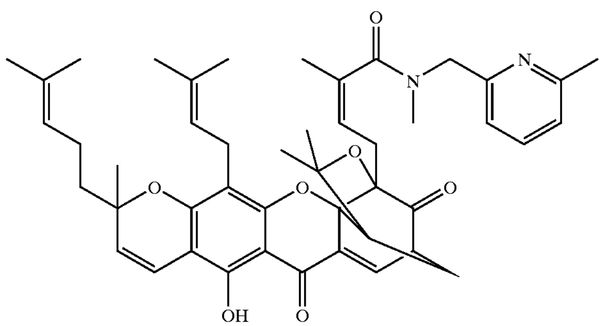 | $C_{46}H_{54}N_2O_7$ | 746.94 |
| 57 | 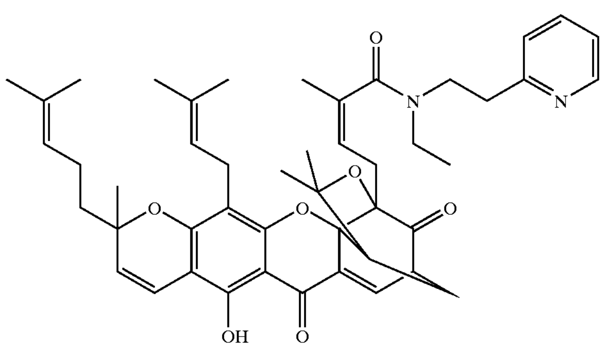 | $C_{47}H_{56}N_2O_7$ | 760.966 |
| 58 | 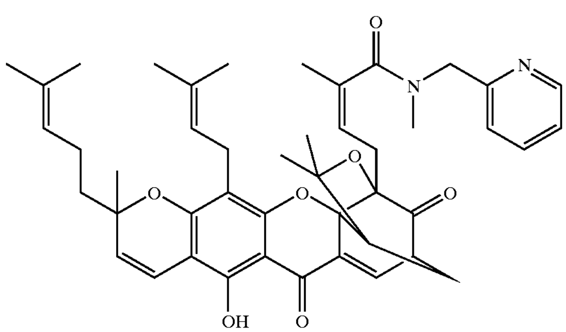 | $C_{45}H_{52}N_2O_7$ | 732.913 |

TABLE I-continued
Examples 37–89
| Example # | STRUCTURE | MF | MW |
|---|---|---|---|
| 59 | 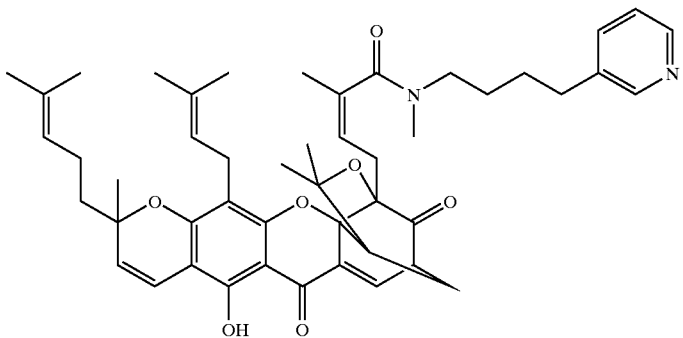 | C₄₅H₅₈N₂O₇ | 774.993 |
| 60 | 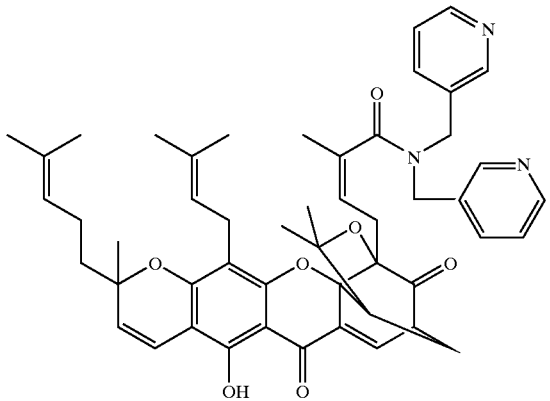 | C₅₀H₅₅N₃O₇ | 809.998 |
| 61 | 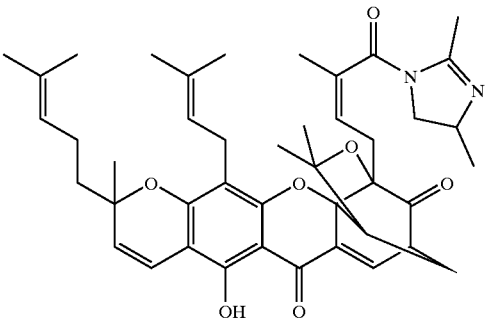 | C₄₃H₅₂N₂O₇ | 708.891 |
| 62 | 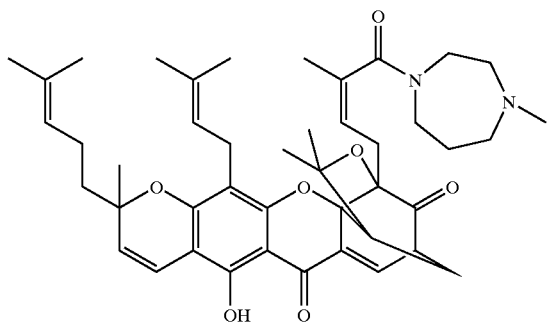 | C₄₄H₅₆N₂O₇ | 724.933 |

TABLE I-continued

Examples 37–89

| Example # | STRUCTURE | MF | MW |
|---|---|---|---|
| 63 | 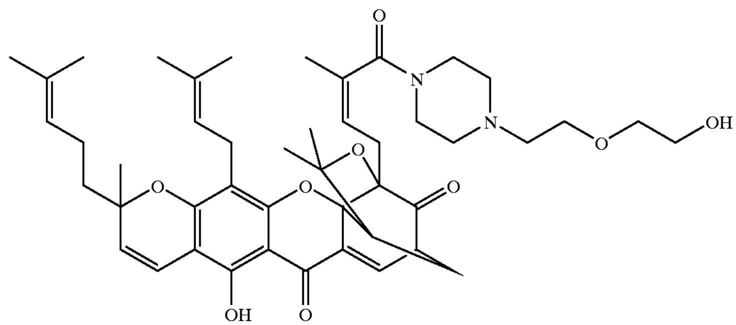 | $C_{46}H_{60}N_2O_9$ | 784.985 |
| 64 | 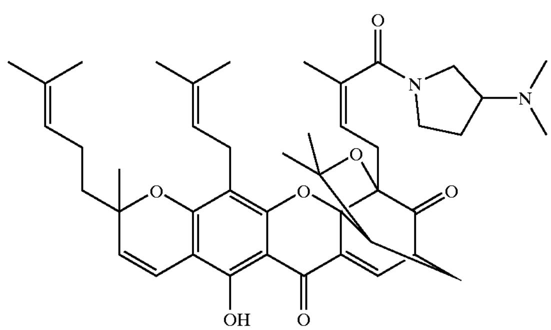 | $C_{44}H_{56}N_2O_7$ | 724.933 |
| 65 | 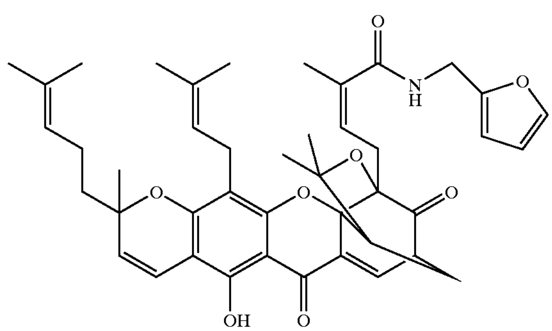 | $C_{43}H_{49}NO_8$ | 707.859 |
| 66 | 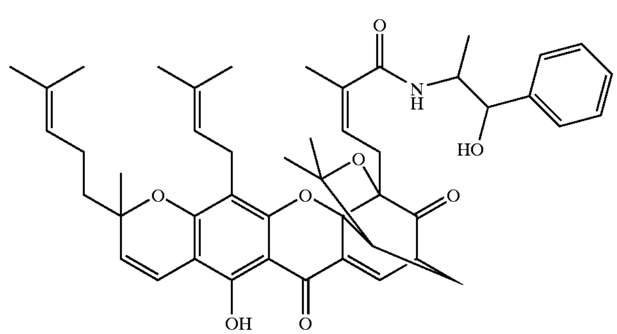 | $C_{47}H_5NO_8$ | 761.951 |

TABLE I-continued

Examples 37–89

| Example # | STRUCTURE | MF | MW |
|---|---|---|---|
| 67 | 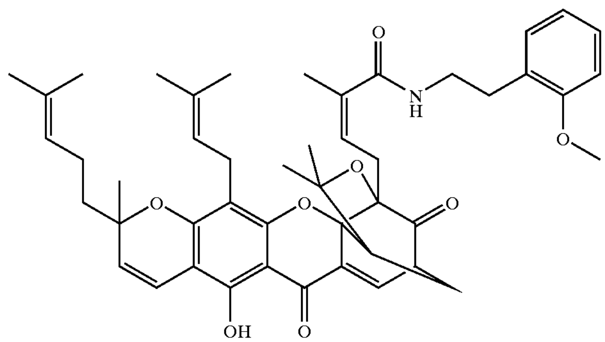 | $C_{47}H_{55}NO_8$ | 761.951 |
| 68 | 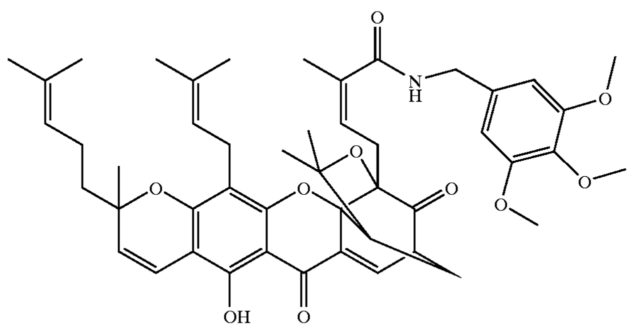 | $C_{48}H_{57}NO_{10}$ | 807.975 |
| 69 | 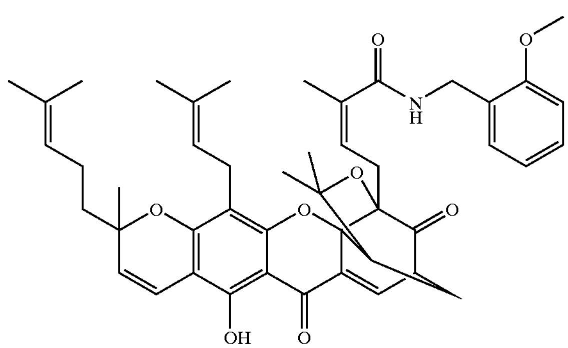 | $C_{46}H_{53}NO_8$ | 747.924 |
| 70 | 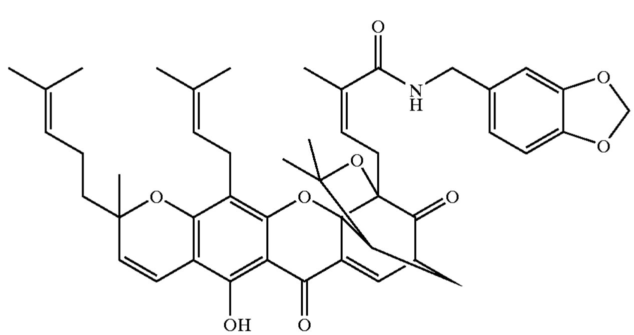 | $C_{46}H_{51}NO_9$ | 761.907 |

TABLE I-continued

Examples 37–89

| Example # | STRUCTURE | MF | MW |
|---|---|---|---|
| 71 | 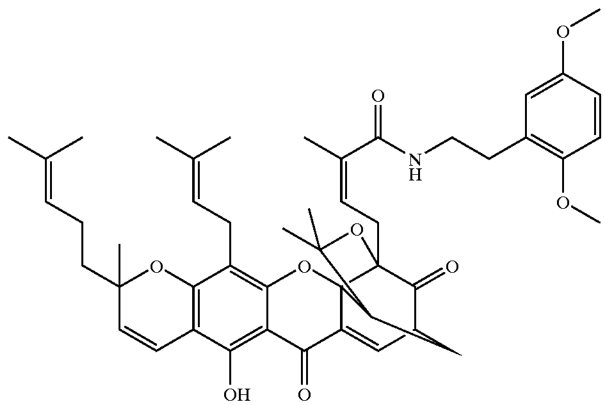 | $C_{48}H_{57}NO_9$ | 791.976 |
| 72 | 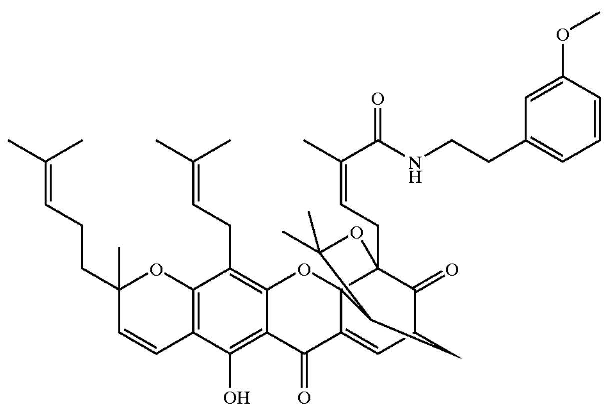 | $C_{47}H_{55}NO_8$ | 761.951 |
| 73 | 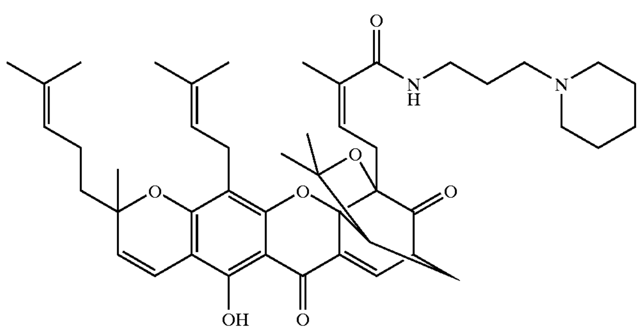 | $C_{46}H_{60}N_2O_7$ | 752.987 |
| 74 | 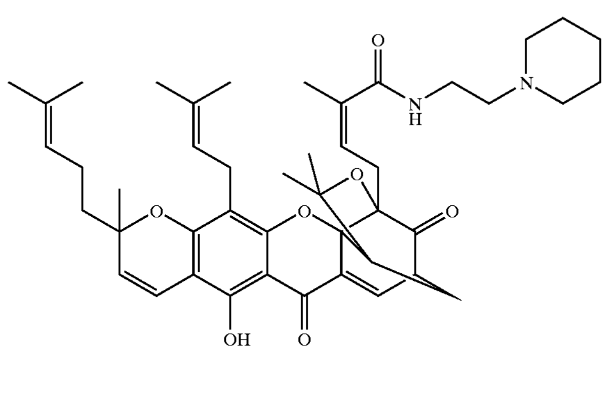 | $C_{45}H_{58}N_2O_7$ | 738.96 |

TABLE I-continued

Examples 37–89

| Example # | STRUCTURE | MF | MW |
|---|---|---|---|
| 75 | 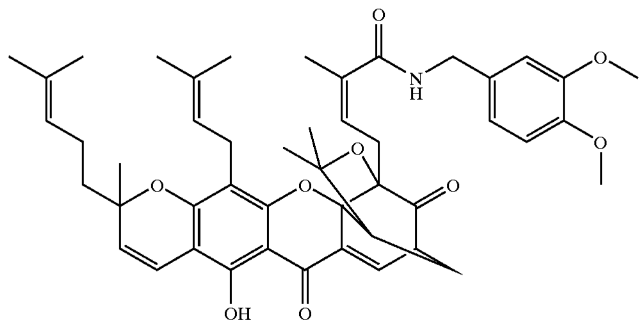 | $C_{47}H_{55}NO_9$ | 777.95 |
| 76 | 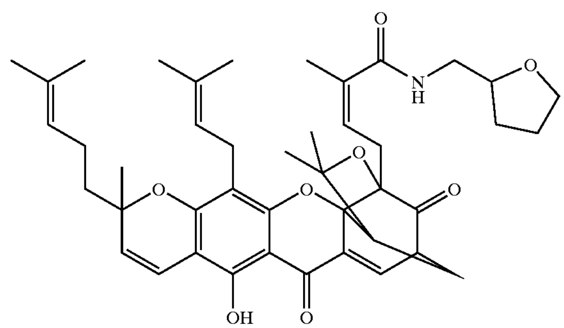 | $C_{43}H_{53}NO_8$ | 711.891 |
| 77 | 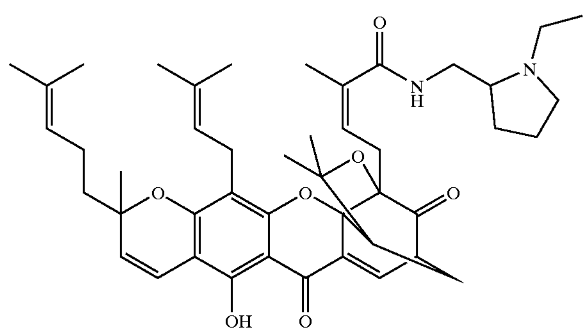 | $C_{45}H_{58}N_2O_7$ | 738.96 |
| 78 | 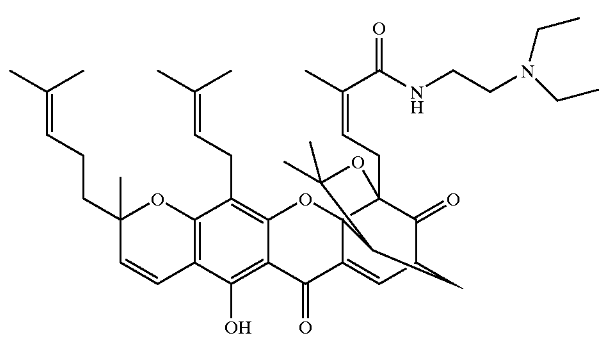 | $C_{44}H_{58}N_2O_7$ | 726.949 |

TABLE I-continued

Examples 37–89

| Example # | STRUCTURE | MF | MW |
|---|---|---|---|
| 79 | 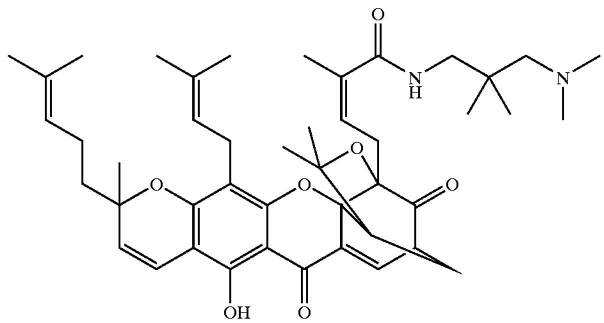 | $C_{45}H_{60}N_2O_7$ | 740.976 |
| 80 | 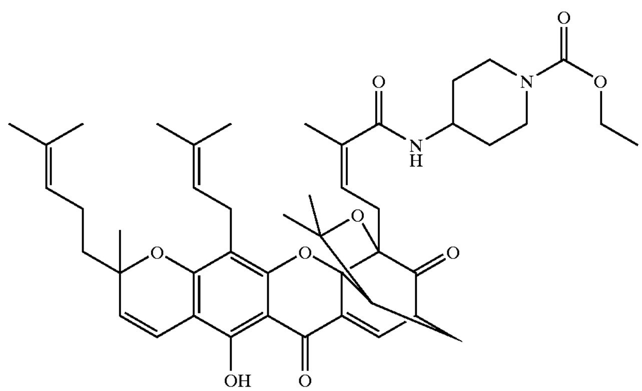 | $C_{46}H_{58}N_2O_9$ | 782.969 |
| 81 | 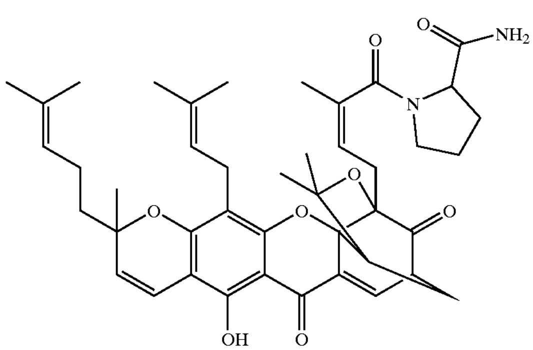 | $C_{43}H_{52}N_2O_8$ | 724.89 |
| 82 | 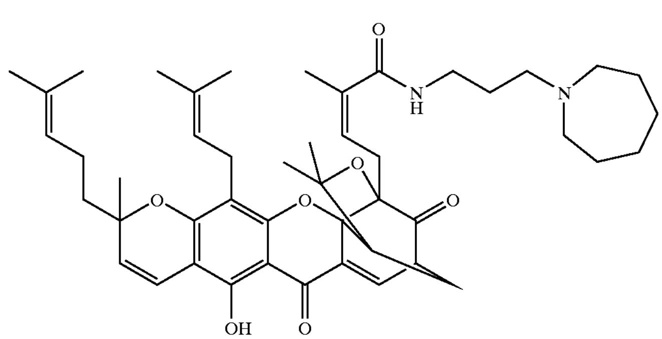 | $C_{47}H_{62}N_2O_7$ | 767.014 |

TABLE I-continued
Examples 37–89
| Example # | STRUCTURE | MF | MW |
|---|---|---|---|
| 83 | 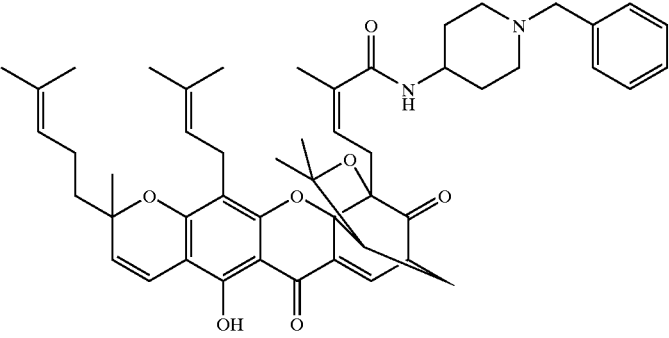 | $C_{50}H_{60}N_2O_7$ | 801.031 |
| 84 | 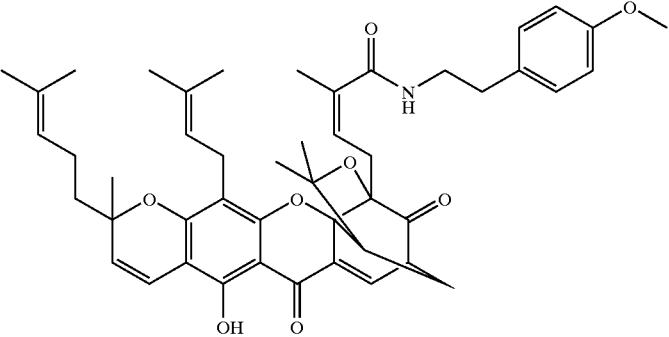 | $C_{47}H_{55}NO_8$ | 761.951 |
| 85 | 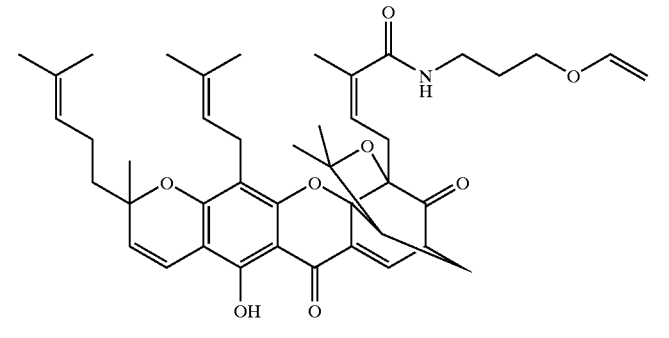 | $C_{43}H_{53}NO_8$ | 711.891 |
| 86 | 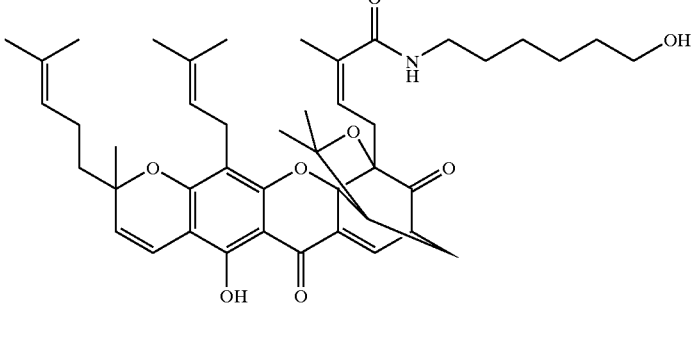 | $C_{44}H_{57}NO_8$ | 727.933 |

TABLE I-continued

Examples 37–89

| Example # | STRUCTURE | MF | MW |
|---|---|---|---|
| 87 | 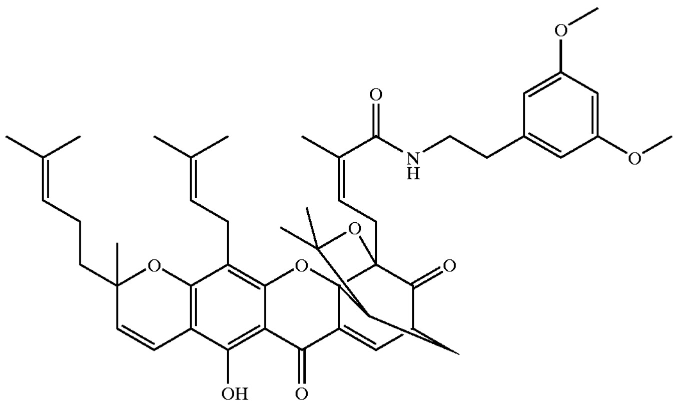 | $C_{48}H_{57}NO_9$ | 791.976 |
| 88 | 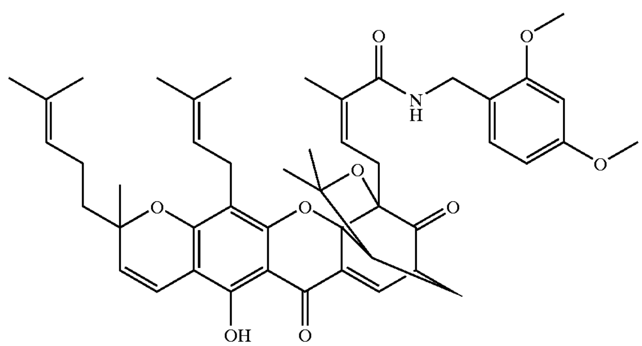 | $C_{47}H_{55}NO_9$ | 777.95 |
| 89 | 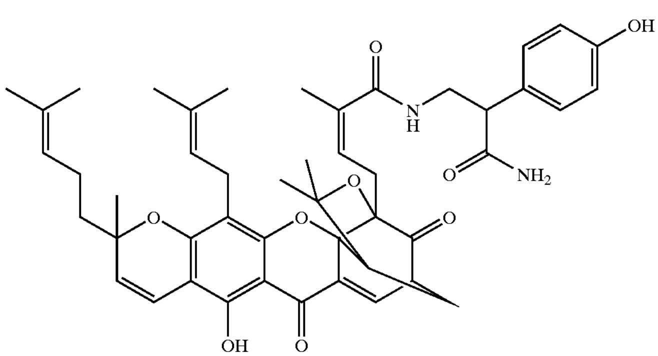 | $C_{47}H_{54}N_2O_9$ | 790.949 |

EXAMPLE 90

Identification Of Gambogic Acid And Analogs As Antineoplastic Compounds That are Caspase Cascade Activators Human breast cancer cell lines T-47D and ZR-75-1, human prostate cancer cell line PC-3, human leukemia cancer cell line HL-60 and human non-transformed fibroblast cell line MRC-5 cells were grown according to media component mixtures designated by The American Type Culture Collection+10% FCS (Life Technologies, Inc.), in a 5% $CO_2$–95% humidity incubator at 37° C. T-47D, ZR-75-1 and PC-3 cells were maintained at a cell density between 30 and 80% confluency and for HL-60 at a cell density of 0.1 to $0.6\times10^6$ cells/ml. Cells were harvested at 600×g and resuspended at $0.65\times10^6$ cells/ml into appropriate media+10% FCS. An aliquot of 45 μl of cells was added to a well of a 96-well microtiter plate containing 5 μl of a 10% DMSO in RPMI-1640 media solution containing 1.6 to 100 μM gambogic acid or other test compound (0.16 to 10 μM final). An aliquot of 45 μl of cells was added to a well of a 96-well microtiter plate containing 5 μl of a 10% DMSO in RPMI-1640 media solution without test compound as the control sample. The samples were mixed by agitation and then incubated at 37° C. for 24 h in a 5% $CO_2$–95% humidity incubator. After incubation, the samples were removed from the incubator and 50 μl of a solution containing 20 μM of N-(Ac-DEVD)-N'-ethoxycarbonyl-R110 fluorogenic substrate (SEQ ID NO:1) (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 μg/ml lysolecithin (Calbiochem) was added. The samples were mixed by agitation and incubated at room temperature. Using a fluorescent plate reader (Model 1420 Wallac Instruments), an initial reading (T=0) was made approximately 1–2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate sample readings as follows:

$$RFU_{(T=3hr)} - Control\ RFU_{(T=0)} = Net\ RFU_{(T=3hr)}$$

The activity of caspase cascade activation was determined by the ratio of the net RFU value for gambogic acid or other test compound to that of control samples. The $EC_{50}$ (nM) was determined by a sigmoidal dose-response calculation (Prism 2.0, GraphPad Software Inc.). The caspase activity (Ratio) potency ($EC_{50}$) are summarized in Table II:

reading (T=0) was made approximately 1–2 min. after addition of the solution, employing absorbance at 490 nm. This determines the possible background absorbance of the test compounds. No absorbance for gambogic acid or its analogs or derivatives was found at 490 nm. After the 2–4 h incubation, the samples were read for absorbance as above (Aest).

Baseline for $GI_{50}$ (dose for 50% inhibition of cell proliferation) and $LC_{50}$ (dose for 50% cell death) of initial cell numbers was determined by adding an aliquot of 90 μl of cells or 90 μl of media, respectively, to wells of a 96-well microtiter plate containing 10 μl of a 10% DMSO in RPMI-1640 media solution. The samples were mixed by agitation and then incubated at 37° C. for 0.5 h in a 5%

TABLE II

Caspase Activity and Potency

| Example # | T-47D Ratio (nM) | T-47D ED50 | ZR-75-1 Ratio (nM) | ZR-75-1 ED50 | PC-3 Ratio (nM) | PC-3 ED50 | HL-60 Ratio (nM) | HL-60 ED50 | MRC-5 Ratio (nM) | MRC-5 ED50 |
|---|---|---|---|---|---|---|---|---|---|---|
| 1 | 13.6 | 560 | 11.9 | 1400 | 2.1 | 1500 | 6.3 | 400 | 17.8 | 1410 |
| 4 | 16.8 | 484 | 14.9 | 1640 | 3.9 | 1330 | 7.7 | 339 | 27.8 | 501 |
| 5 | 13.9 | 210 | 14.3 | 783 | 2.7 | 900 | 5.2 | 200 | 12.6 | 631 |
| 6 | 12.0 | 2800 | ND | ND | 4.5 | 5000 | ND | ND | ND | ND |
| 2 | 16.9 | 310 | 14.2 | 1160 | 2.9 | 1350 | 5.6 | 340 | 22.4 | 1260 |
| 3 | 7.0 | 1000 | ND | ND | 2.9 | 1700 | ND | ND | ND | ND |
| 7 | 14.4 | 830 | 13.4 | 1650 | 2.3 | 1700 | ND | ND | 9.4 | 1200 |
| 9 | 11.7 | 990 | 12.8 | 2050 | 3.1 | 5900 | ND | ND | 11.4 | 1900 |

ND = not determined

Thus, gambogic acid and its derivatives and analogs are identified as potent caspase cascade activators and antineoplastic compounds in this assay.

EXAMPLE 91

Identification Of Gambogic Acid And Analogs As Antineoplastic Compounds That Exhibit Inhibition Of Cell Proliferation ($GI_{50}$) And Cell Death ($LC_{50}$)

T-47D, ZR-75-1, PC-3, human prostate cancer cell line DU-145, human non-small cell lung cancer cell line A-549, human small cell lung cancer cell line SHP-77, HL-60 and MRC-5 cells were grown and harvested as in Example 90. An aliquot of 90 μl of cells ($2.2 \times 10^4$ cells/ml) was added to a well of a 96-well microtiter plate containing 10 μl of a 10% DMSO in RPMI-1640 media solution containing 1 nM to 100 μM gambogic acid or other test compound (0.1 nM to 10 μM final). An aliquot of 90 μl of cells was added to a well of a 96-well microtiter plate containing 10 μl of a 10% DMSO in RPMI-1640 media solution without compound as the control sample for maximal cell proliferation ($A_{max}$). The samples were mixed by agitation and then incubated at 37° C. for 48 h in a 5% $CO_2$–95% humidity incubator. After incubation, the samples were removed from the incubator and 20 μl of CellTiter 96 $AQ_{UEOUS}$ One Solution Cell Proliferation™ reagent (Promega) was added. The samples were mixed by agitation and incubated at 37° C. for 2–4 h in a 5% $CO_2$–95% humidity incubator. Using an absorbance plate reader (Model 1420 Wallac Instruments), an initial $CO_2$–95% humidity incubator. After incubation, the samples were removed from the incubator and 20 μl of CellTiter 96 $AQ_{UEOUS}$ One Solution Cell Proliferation™ reagent (Promega) was added. The samples were mixed by agitation and incubated at 37° C. for 2–4 h in a 5% $CO_2$–95% humidity incubator. Absorbance was read as above, ($A_{T=0}$) defining absorbance for initial cell number used as baseline in $GI_{50}$ determinations and ($A_{min}$) defining absorbance for media alone used as baseline in $LC_{50}$ determinations.

Calculation:

$GI_{50}$ (dose for 50% inhibition of cell proliferation)

$$50 = 100 \times [(A_{Test} - A_{T=0})/(A_{max} - A_{T=0})]$$

$LC_{50}$ (dose for 50% cell death)

$$10 = 50 = 100 \times [(A_{Test} - A_{min})/(A_{T=0} - A_{min})]$$

The $GI_{50}$ (nM) and $LC_{50}$ (nM) are summarized in Table III:

TABLE III $GI_{50}$ and $LC_{50}$ in Cancer Cells

| Cell lines | Gambogic acid | | Methyl Gambogate | | Gambogyl Piperidine | | Methyl-6-Methoxy-gambogate | | Gambogenic Acid | | Gambogenin | |
|---|---|---|---|---|---|---|---|---|---|---|---|---|
| | $GI_{50}$ (nM) | $LC_{50}$ | $GI_{50}$ (nM) | $LC_{50}$ | $GI_{50}$ (nM) | $LC_{50}$ | $GI_{50}$ (nM) | $LC_{50}$ | $GI_{50}$ (nM) | $LC_{50}$ | $GI_{50}$ (nM) | $LC_{50}$ |
| T-47D   | 65  | 450  | 40  | 50   | 50  | 50   | 50  | 80  | 500  | 500  | 500  | 500 |
| ZR-75-1 | 400 | 500  | 300 | 500  | 300 | 500  | 400 | 500 | ND   | ND   | ND   | ND  |
| PC-3    | 500 | 700  | 500 | 500  | 500 | 500  | 500 | 500 | 3000 | 5000 | 5000 | 5000 |
| DU-145  | 500 | 800  | 500 | 500  | 500 | 500  | 500 | 900 | 600  | 5000 | 2000 | 5000 |
| A-549   | 800 | 5000 | 500 | 2000 | 800 | 5000 | 500 | 900 | ND   | ND   | ND   | ND  |
| SHP-77  | 500 | 500  | 500 | 500  | 500 | 500  | 500 | 500 | ND   | ND   | ND   | ND  |
| HL-60   | 500 | 700  | 50  | 500  | 100 | 800  | 100 | 800 | ND   | ND   | ND   | ND  |
| MRC-5   | 400 | 500  | 200 | 500  | 800 | 800  | 500 | 500 | 500  | 5000 | 3000 | 5000 |

ND = not determined

Thus, gambogic acid and its analogs and derivatives are identified as potent antineoplastic compounds that both inhibit cell proliferation (GI50) and elicit cell death ($LC_{50}$).

EXAMPLE 92

Identification Of Vinblastine, Cisplatin, 5-Fluorouracil, Taxol, Camptothecin, Doxorubicin, Etoposide And Methotrexate As Conventional Antineoplastic Agents That Are Not Efficient Caspase Cascade Activators In Solid Tumors T-47D, ZR-75-1, PC-3 and HL-60 cells were grown and harvested as in Example 90. An aliquot of 45 µl of cells was added to a well of a 96-well microtiter plate containing 5 µl of a 10% DMSO in RPMI-1640 media solution containing 100 µM of test compounds (10 µM final). An aliquot of 45 µl of cells was added to a well of a 96-well microtiter plate containing 5 µl of a 10% DMSO in RPMI-1640 media solution without test compound as the control sample. The samples were mixed by agitation and then incubated at 37° C. for 24 h in a 5% $CO_2$–95% humidity incubator. After incubation, the samples were removed from the incubator and 50 µl of a solution containing 20 µM of N-(Ac-DEVD)-N'-ethoxycarbonyl-R110 fluorogenic substrate (SEQ ID NO:1) (Cytovia, Inc.), 20% sucrose (Sigma), 20 mM DTT (Sigma), 200 mM NaCl (Sigma), 40 mM Na PIPES buffer pH 7.2 (Sigma), and 500 µg/ml lysolecithin (Calbiochem) was added. The samples were mixed by agitation and incubated for 3 h at room temperature. Using a fluorescent plate reader (Model 1420 Wallac Instruments), an initial reading (T=0) was made approximately 1–2 min. after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T-3hr)} - Control\ RFU_{(T-0)} = Net\ RFU_{(T-3hr)}$$

The activity in caspase cascade activation was determined by the ratio of the net RFU value for test compounds to that of control samples. A ratio around 1 indicates that the compound is not an efficient caspase cascade activator. The ratios are summarized in Table IV.

TABLE IV

Activity of Known Antineoplastic Compound as Caspase Cascade Activators

| | Cell lines | |
|---|---|---|
| | T-47D | PC-3 |
| Vinblastine | 0.9 | 0.8 |
| Cisplatin | 1.1 | 0.9 |
| 5-fluorouracil | 0.8 | 0.7 |
| Taxol | 0.9 | 0.7 |
| Camptothecin | 0.7 | 0.6 |
| Doxorubicin | 1.3 | 1.1 |
| Etoposide | 1.0 | 0.8 |
| Methotrexate | 0.8 | 0.7 |

Thus, vinblastine, cisplatin, 5-fluorouracil, taxol, camptothecin, doxorubicin, etoposide and methotrexate are identified as known antineoplastic compounds that are not caspase cascade activators in this assay.

EXAMPLE 93

Morphological Change of T47D Cells Treated with Gambogic Acid Cells undergoing apoptosis typically demonstrate several characteristic morphological changes, including rounding and blebbing. In addition, apoptotic adherent cells in culture lose their ability to remain attached to the culture dish. The ability of gambogic acid to trigger these morphological changes in T47D cells was investigated.

60 mm culture dishes were seeded with 750,000 T47D cells and the cultures were incubated under normal growth conditions (complete medium with 10% FBS) for 24 h. The cells were then treated with 2.5 µM of gambogic acid and further incubated under normal growth conditions for 2 or 6 h. Morphological changes were documented by photographing the cells under phase contrast illumination.

Figure 1B:
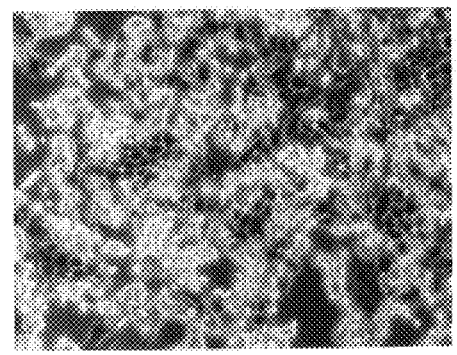
Figure 1C:
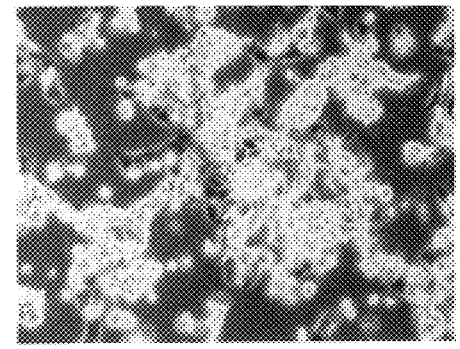

As shown in FIGS. 1A–C, T47D cells incubated with vehicle (Control) are phase-dark and show a normal, flat morphology (FIG. 1A). After 2 h of treatment with gambogic acid, many of the cells have taken on a rounded, phase-bright morphology (FIG. 1B). By 6 h of treatment with gambogic acid, most of the cells in the culture are rounded up and are beginning to detach from the dish (FIG. 1C). At this timepoint, many of the cells also show evidence of blebbing. Based on these data, it was concluded that gambogic acid induces apoptotic morphological changes in T47D cells.

EXAMPLE 94

Gambogic Acid Induces Nuclear Fragmentation in T47D Breast Cancer Cells

Figure 2A:
FIGS. 2A–B depict fluorescent photographs of T47D human breast cancer cells treated with gambogic acid and stained with a fluorescent DNA probe: control cells (FIG. 2A); cells treated with 10 μM of gambogic acid for 24 h (FIG. 2B).
Figure 2B:
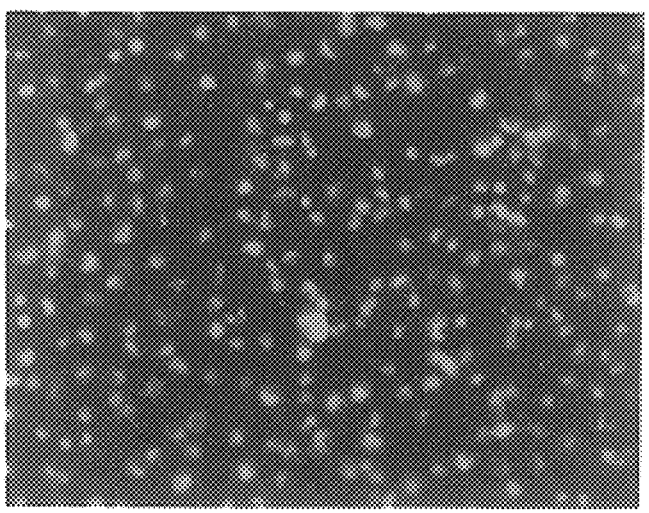

T47D cells were grown and plated as described in Example 90. The cells were treated with 10 μM of gambogic acid and the plate was incubated for up to 24 h at 37° C. in a 5% $CO_2$–95% humidity incubator. At 24 h, the cells were incubated with a live cell nucleic acid stain, Syto16 (Molecular Probes) which stains DNA. After 2 washes with PBS, cells were examined under a fluorescence microscope. The nuclear staining of untreated cells showed normal nuclei (FIG. 2A) whereas the gambogic acid treated cells showed condensed and fragmented nuclei in a large population of the cells (FIG. 2B). Nuclear fragmentation is a clear indicator of cellular apoptosis.

EXAMPLE 95

Gambogic Acid Induces Characteristic Apoptotic Morphology in Jurkat Cells

Jurkat T leukemia cells were grown in RPMI 1640 media (Life Technologies, Inc.)+10% FCS (Sigma Chemical Company) in a 5% $CO_2$–95% humidity incubator at 37° C., and maintained at a cell density between 4 and 8×10$^5$ cells/ml. Cells were harvested at 200×g and resuspended at 1–2×10$^6$ cells/ml into RPMI 1640 media+10% FCS, and 3 ml of the cells was dispensed in each of three wells of a 6-well plate. One of the wells was treated with 10 μM caspase inhibitor cbz-Val-Asp-fmk (Cytovia, Inc.; WO99/18781) and the plate was incubated at 37° C. in a 5% $CO_2$–95% humidity incubator for 1 h prior to addition of gambogic acid. The wells with and without the caspase inhibitor were treated with 10 μM gambogic acid. The third well was treated with solvent (control cells). The plate was incubated at 37° C. in a 5% $CO_2$–95% humidity incubator.

At 30 min. after addition of gambogic acid an aliquot of cells from each well was taken into the capillary slides and observed under a phase-contrast microscope.

Figure 3A:
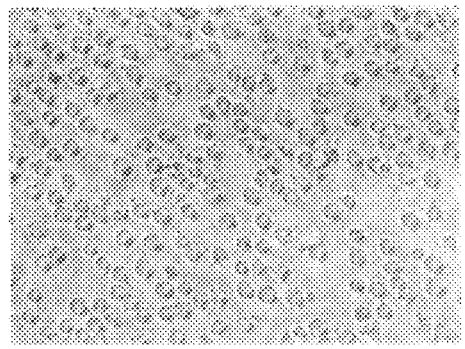
FIGS. 3A–C depict photographs of Jurkat leukemia cells treated with gambogic acid: control cells (FIG. 3A); cells treated with 10 μM of gambogic acid for 30 min (FIG. 3B); cells treated with 10 μM of gambogic acid in the presence of 10 μM of caspase inhibitor cbz-Val-Asp-fink (FIG. 3C).
Figure 3B:
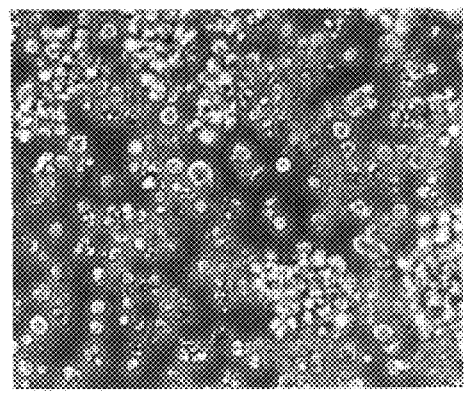
Figure 3C:
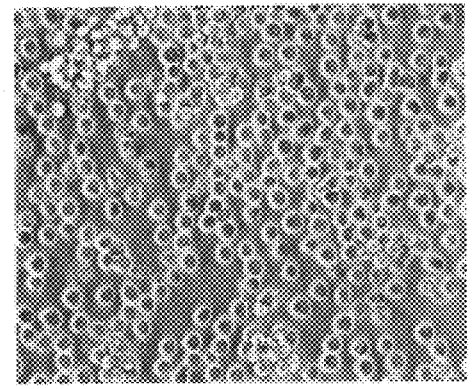

The control cell samples showed normal cell morphology (FIG. 3A) whereas after 30 min. treatment with gambogic acid the cells showed blebbing and cellular fragmentation (FIG. 3B), hallmarks of apoptosis. The presence of caspase inhibitor prevented the morphological changes (FIG. 3C), indicating that the changes are due to activation of caspases in the cell.

EXAMPLE 96

Activation of Caspases by Gambogic Acid in T47D Breast Cancer Cell Line and in Normal Fibroblasts MRC-5

T47D cells and MRC-5 cells were maintained and harvested as described in Example 90. An aliquot of 45 μl of cells was added to each well of a 96-well microtiter plate. To determine the dose response of gambogic acid for inducing caspase activity, 5 μl of 20 μM gambogic acid in RPMI media was added to wells in triplicates. Two-fold serial dilutions were made for the lower concentrations. After incubation for 2 h, the samples were removed from the 5% $CO_2$–95% humidity incubator and caspase activity was determined by addition of a fluorogenic substrate as described in Example 90.

Figure 4:
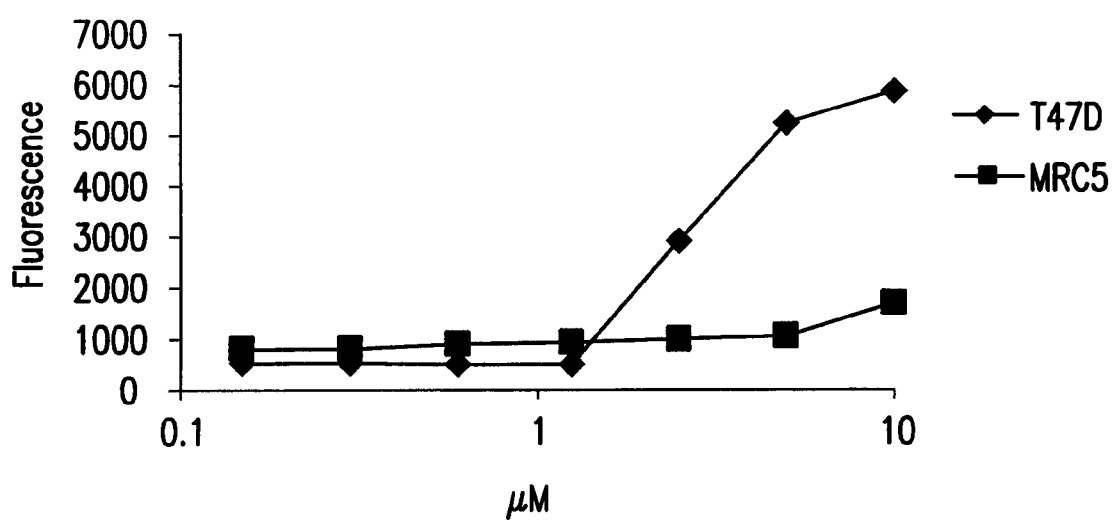
FIG. 4 depicts the caspase activity in T47D human breast cancer cells and MRC5 human non-transformed fibroblast cells treated for 2 h with different concentrations of gambogic acid.

The dose response (FIG. 4) indicated that the human breast cancer cell line T47D is more sensitive to induction of caspase activity than a normal fibroblast cell line MRC-5 by gambogic acid. Therefore, there is a potential therapeutic index with gambogic acid treatment.

EXAMPLE 97

Gambogic Acid Induces Caspase Activity in a Variety of Solid Tumor Cell Lines Which Is Inhibited by a Caspase Inhibitor T47D, ZR-75, PC3, SHP-77 and A-549 cells were maintained and harvested as described in Example 90. Cells were added to 96-well plates as described in Example 90. The cells were treated with 10 μM gambogic acid, in the presence and in the absence of 10 μM caspase inhibitor cbz-Val-Asp-fmk (Cytovia, Inc.; WO99/18781). The plate was incubated up to 24 h at 37° C. in a 5% $CO_2$–95% humidity incubator. Caspase activity was determined by addition of a fluorogenic substrate as described in Example 90.

Gambogic acid induced caspase activity in a ratio of greater than 2.5 (+) above untreated cell levels in all the tested cancer cell lines (Table IV). The caspase activity detected was inhibited by the caspase inhibitor (+), confirming that the fluorescent signal was due to caspase activity.

TABLE IV

Gambogic Acid as Caspase Inducers in Solid Tumor Cells

| Cell line | Caspase activity | Inhibition of caspase activity by Inhibitor |
| --- | --- | --- |
| T47D | + | + |
| ZR-75 | + | + |
| PC-3 | + | + |
| SHP-77 | + | + |
| A-549 | + | + |

EXAMPLE 98

Induction of PARP Cleavage by Gambogic Acid in Human Tumor Cells

Cleavage of the enzyme poly(ADP)ribose polymerase (PARP) by caspase-3 and related proteases is considered to be one of the molecular hallmarks of caspase-mediated apoptosis. Therefore, the ability of gambogic acid to induce PARP cleavage in four different human tumor cell lines (Jurkat cells, HL-60 cells, T47D cells and PC3 cells) was determined.

Cells were cultured in complete growth medium containing 10% FBS and treated with gambogic acid at concentrations of 2.5 μM or 5 μM for 2 to 4 h. Control cultures were treated with a drug vehicle (DMSO), or the well-characterized apoptosis inducer, staurosporine. At the end of the apoptosis induction period, the cells were harvested, washed once with PBS, quick-frozen on dry ice, and stored at −80° C. The cells were then lysed in a standard immunoblotting lysis buffer and samples of the lysates were electrophoresed on 4% to 20% gradient polyacrylamide gels. The proteins in the gels were then transferred to PVDF membranes and probed with a commercially-available rabbit polyclonal antibody to PARP.

FIGS. 5A–D illustrate the results of these experiments. A 2 h treatment with 2.5 μM gambogic acid induced almost complete PARP cleavage in both Jurkat cells (FIG. 5A) and HL-60 cells (FIG. 5B). 2.5 μM gambogic acid was as effective as 1 μM staurosporine, one of the most potent apoptosis inducers known. There was no PARP cleavage in cells treated with drug vehicle (DMSO) or another inactive control.

Figure 5A:
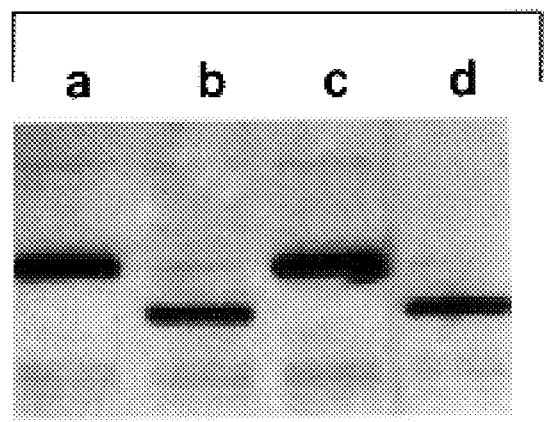
FIGS. 5A–D depict western blots of poly(ADP)ribose polymerase (PARP) cleavage.
Figure 5B:
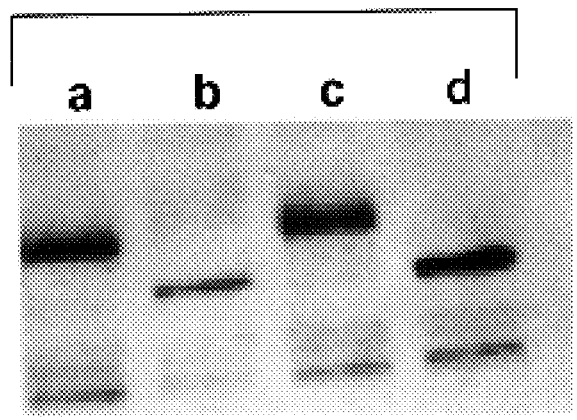
Figure 5C:
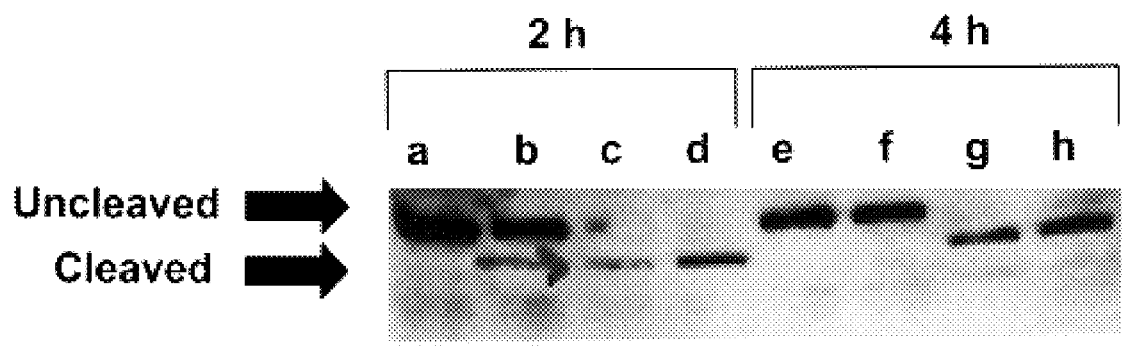

FIG. 5C shows the effect of gambogic acid on PARP cleavage in T47D cells. Within 2 h of treatment, using 2.5 μM gambogic acid, moderate induction of PARP cleavage is observed; almost complete PARP cleavage is observed with 5 μM gambogic acid. Within 4 h of treatment, both concentrations of gambogic acid give almost complete PARP cleavage. Under the same conditions, no cleavage of PARP was observed for cells treated with 1 μM staurosporine.

Figure 5D:
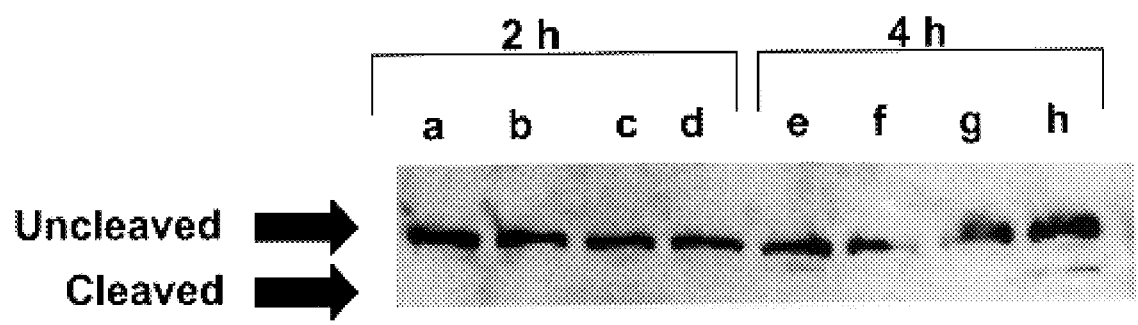

PC3 cells, a human prostate cancer cell line, were more resistant to the induction of PARP cleavage by gambogic acid (FIG. 5D). Within 2 h of treatment, neither concentration (2.5 μM and 5 μM) of drug was effective. Within 4 h of treatment, a moderate amount of PARP cleavage product could be observed with the highest dose of gambogic acid (5 μM). Under the same conditions, no cleavage of PARP was observed for cells treated with 1 μM staurosporine.

Based on these experiments, it was concluded that gambogic acid triggers PARP cleavage in all four human tumor cell lines tested. These results indicate that gambogic acid is an effective inducer of caspase-mediated apoptosis in tumor cells under normal growth conditions.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What Is claimed is:

1. A method of inducing cell apoptosis in a mammal in need thereof, comprising administering to said mammal an effective amount of a compound having one of the Formulae I–III:

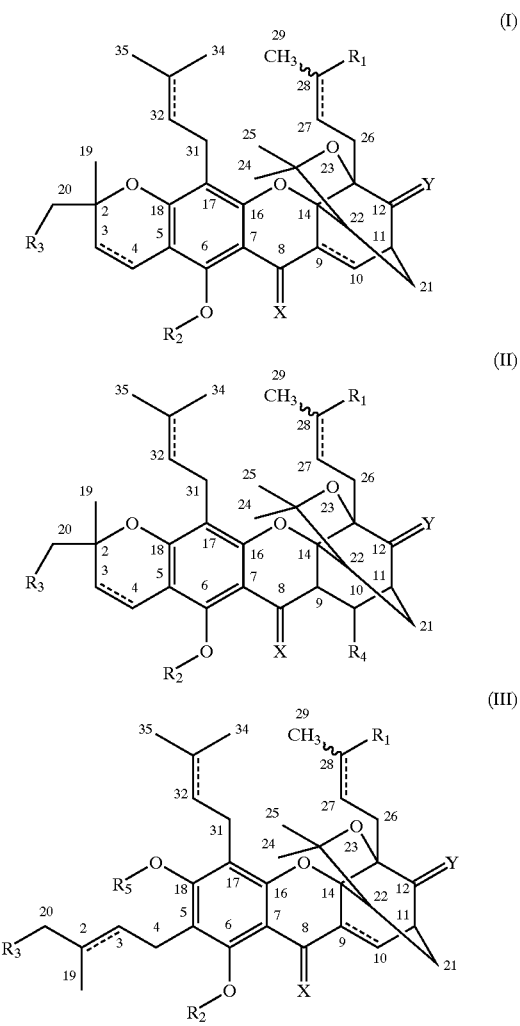

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: synthetic peptide

<400> SEQUENCE: 1

Asp Glu Val Asp
 1 or a pharmacuetically acceptable salt or prodrug thereof, wherein:

the dotted lines are single bonds, double bonds or epoxy groups;

X together with the attached carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

$R_1$ is formyl, methylenehydroxy, carboxy, acyl ($R_aCO$), optionally substituted alkoxycarbonyl ($R_aOCO$), optionally substituted alkylthiocarbonyl, optionally substituted aminocarbonyl (carbamyl, $R_bR_cNCO$) or hydroxyaminocarbonyl, where $R_a$ is optionally substituted lower alkyl; $R_b$ and $R_c$ are independently hydrogen, optionally substituted heteroalkyl, optionally substituted lower alkyl, optionally substituted aryl, optionally substituted heteroaryl or optionally substituted lower aralkyl groups; or $R_b$ and $R_a$ may be taken together with the attached N to form an optionally substituted, saturated or partially saturated 5–7 membered heterocyclo group;

$R_2$ is hydrogen, optionally substituted alkyl, acyl ($R_aCO$), carbamyl ($R_bR_cNCO$) or sulfonyl ($R_aSO_2$), where $R_a$, $R_b$, and $R_c$ are defined above; $R_d$ is hydrogen, optionally substituted lower alkyl, optionally substituted aryl, or optionally substituted lower aralkyl groups;

$R_3$ is hydrogen or prenyl;

$R_4$ is hydrogen, halogen, hydroxy, optionally substituted alkyl, cycloalkyl, alkoxy, alkylthio or amino; and $R_5$ is hydrogen, optionally substituted alkyl, acyl ($R_aCO$), carbamyl ($R_bR_cNCO$) or sulfonyl ($R_aSO_2$), where $R_a$, $R_b$, $R_c$ and $R_d$ are defined above;

with the provisos that when said mammal has cancer, then (a) said compound is not gambogic acid, isogambogic acid, morellinol, isomorellinol or gambogin, (b) said compound is of Formula I or II, and (c) $R_3$ is prenyl.

2. The method of claim 1, wherein the dotted lines between C-9 and C-10 of a compound of Formula I or III represent a double bond, $R_4$ is not a cycloalkyl group, the other dotted lines are not epoxy groups, and $R_b$ and $R^c$ are not heteroalkyl groups.

3. A method according to claim 1, wherein $R_1$ is formyl, acetyl, propionyl, carboxy, methoxycarbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N'-piperazinylcarbonyl, 2(dimethylamino)-ethylcarbamyl or N-morpholinylcarbonyl, and the dotted lines represent double bonds.

4. A method according to claim 1, wherein $R_2$ is hydrogen, formyl, acetyl, dimethylcarbamyl, diethylcarbamyl, 2-(dimethylamino)ethyl-carbamyl, N-piperidinylcarbonyl, N-methyl-N'-piperazinylcarbonyl, N-morpholinylcarbonyl, methylsulfonyl, ethylsulfonyl, phenylsulfonyl, methyl, ethyl, 2-piperidinylethyl, 2-morpholinylethyl, 2-(dimethylamino)ethyl, or 2-(diethylamino)ethyl, and the dotted lines represent double bonds.

5. A method according to claim 1, wherein $R_4$ is methyl, ethyl, phenyl, chloro, bromo, hydroxy, hydrogen, methoxy, ethoxy, methylthio, ethylthio, butylthio, dimethylamino, diethylamino, piperidinyl, pyrrolidinyl, imidazolyl, pyrazolyl, N-methylpiperazinyl, 2-(dimethylamino) ethylamino or morpholinyl, and the dotted lines represent double bonds.

6. A method according to claim 1, wherein $R_5$ is hydrogen, acetyl, dimethylcarbamyl, diethylcarbamyl, 2-(dimethylamino)ethylcarbamyl, N-piperidinylcarbonyl, N-methyl-N'-piperazinylcarbonyl, N-morpholinyl-carbonyl, methylsulfonyl, ethylsulfonyl, phenylsulfonyl, methyl, ethyl, 2-piperidinylethyl, 2-morpholinylethyl, 2-(dimethylamino)ethyl, or 2-(diethylamino)ethyl.

7. The method according to claim 1, wherein said compound is selected from the group consisting of:

Methyl gambogate ester;
9,10-Dihydrogambogyl (4-methylpiperazine);
9,10-Dihydrogambogyl (2-dimethylaminoethylamine);
9,10-Dihydro-12-hydroxygambogic acid;
Gambogyl diethylamine;
Gambogyl dimethylamine;
Gambogyl amine;
Gambogyl hydroxyamine;
Gambogyl piperidine;
6-Methoxy-gambogic acid;
6-(2-Dimethylaminoethoxy)-gambogic acid;
6-(2-Piperidinylethoxy)-gambogic acid;
6-(2-Morpholinylethoxy)-gambogic acid;
6-Methoxy-gambogyl piperidine;
Gambogyl morpholine;
Gambogyl (2-dimethylaminoethylamine);
9,10-Dihydro-10-morpholinyl-gambogyl morpholine;
9,10-Dihydro-10-morpholinyl-gambogyl piperidine;
9,10-Dihydro-10-(4-methylpiperazinyl)-gambogyl piperidine;
9,10-Dihydro-10-(4-methylpiperazinyl)-gambogyl morpholine;
9,10-Dihydro-10-piperidinyl-gambogyl piperidine;
9,10-Dihydro-10-(4-methylpiperazinyl)-gambogyl (4-methylpiperazine);
10-Cyclohexyl-9,10-dihydrogambogic acid;
9,10-Dihydro-10-methyl gambogic acid;
Gambogyl (4-methylpiperazine);
Methyl-6-Methoxy-gambogate;
9,10-Dihydro-10-methoxy-gambogic acid;
10-Butylthio-9,10-dihydrogambogic acid;
9,10-Dihydro-10-(4-methylpiperazinyl)-gambogic acid;
9,10-Dihydro-10-pyrrolidinyl-gambogic acid;
Methyl-9,10-dihyrdro-10-morpholinyl-gambogate;
9,10-Dihydro-10-piperidinyl-gambogic acid;
9,10-Dihydro-10-morpholinyl-gambogic acid;
N-(2-Gambogylamido-ethyl)biotinamide;
Gambogyl (2-(4-morpholinyl)ethylamine);
9,10-Epoxygambogic acid;
Gambogyl (4-(2-pyridyl)piperazine);
9,10-Dihydro-10-(4-(2-pyridyl)piperazinyl)gambogyl (4-(2-pyridyl)piperazine);
6-Acetylgambogic acid;
9,10-Dihydro-10-(4-(2-pyridyl)piperazinyl)gambogic acid;
8-(Gambogylamido)octanoic acid;
6-(Gambogylamido)hexanoic acid;

12-(Gambogylamido)dodecanoic acid;
9,10-Dihydro-10-methoxy-gambogyl piperidine;
Gambogyl (4-(2-pyrimidyl)piperazine);
Gambogyl (bis(2-pyridylmethyl)amine);
Gambogyl (N-(3-pyridyl)-N-(2-hydroxybenzyl)amine);
Gambogyl (4-benzylpiperazine);
Gambogyl (4-(3,4-methylenedioxybenzyl)piperazine);
Gambogyl (-methyl-5-(methylamino)-3-oxapentylamine);
Gambogyl (N-methyl-8-(methylamino)-3,6-dioxaoctylamine);
Gambogyl (N-ethyl-2-(ethylamino)ethylamine);
Gambogyl (4-isopropylpiperazine);
Gambogyl (4-cyclopentylpiperazine);
Gambogyl (N-(2-oxo-2-ethoxyethyl)-(2-pyidyl)methylamine);
Gambogyl (2,5-dimethylpiperazine);
Gambogyl (3,5-dimethylpiperazine);
Gambogyl (4-(4-acetylphenyl)piperazine);
Gambogyl (4-ethoxycarbonylpiperazine);
Gambogyl (4-(2-oxo-2-pyrrolidylethyl)piperazine);
Gambogyl (4-(2-hydroxyethyl)piperazine);
Gambogyl (N-methyl-2-(methylamino)ethylamine);
Gambogyl (N-methyl-2-(benzylamino)ethylamine);
Gambogyl (N-methyl-(6-methyl-2-pyridyl)methylamine);
Gambogyl (N-ethyl-2-(2-pyridyl)ethylamine);
Gambogyl (N-methyl-(2-pyridyl)methylamine);
Gambogyl (N-methyl-4-(3-pyridyl)butylamine);
Gambogyl (bis(3-pyridylmethyl)amine);
Gambogyl (2,4-dimethyl-2-imidazoline);
Gambogyl (4-methyl-homopiperazine);
Gambogyl (4-(5-hydroxy-3-oxapentyl)piperazine);
Gambogyl (3-dimethylaminopyrrolidine);
Gambogyl ((2-furanyl)methylamine);
Gambogyl (2-hydroxy-1-methyl-2-phenylethylamine);
Gambogyl (3,4,5-trimethoxybenzylamine);
Gambogyl (2-($^2$-methoxyphenyl)ethylamine);
Gambogyl (2-methoxybenzylamine);
Gambogyl (3,4-methylenedioxybenzylamine);
Gambogyl (2-(2,5-dimethoxyphenyl)ethylamine);
Gambogyl (2-(3-methoxyphenyl)ethylamine);
Gambogyl (3-(piperidinyl)propylamine);
Gambogyl (2-(piperidinyl)ethylamine);
Gambogyl (3,4-dimethoxybenzylamine);
Gambogyl ((2-tetrahydrofuranyl)methylamine);
Gambogyl ((N-ethyl-2-pyrrolidinyl)methylamine);
Gambogyl (2-diethylaminoethylamine);
Gambogyl (2,2-dimethyl-3-dimethylaminopropylamine);
Gambogyl ((N-ethoxycarbonyl-4-piperidinyl)amine);
Gambogyl (2-carbamylpyrrolidine);
Gambogyl (3-(homopiperidinyl)propylamine);
Gambogyl ((N-benzyl-4-piperidinyl)amine);
Gambogyl (2-(4-methoxyphenyl)ethylamine);
Gambogyl (4-oxa-hex-5-enylamine);
Ganbogyl (6-hydroxyhexylamine);
Gambogyl (2-(3,5-dimethoxyphenyl)ethylamine);
Gambogyl (3,5-dimethoxybenzylamine); and
Gambogyl (2-carbamyl-2-(4-hydroxyphenyl)ethylamine).

8. A method for treating cancer, comprising administering to an animal in need of such treatment an effective amount of a compound having the Formula I or II:

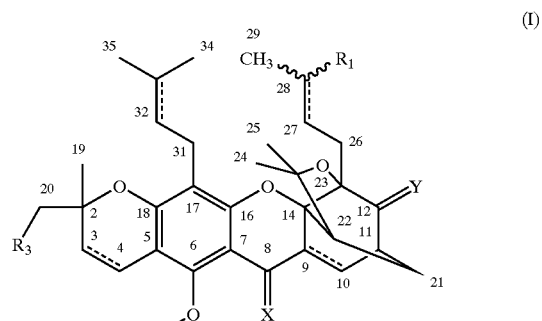

(I)

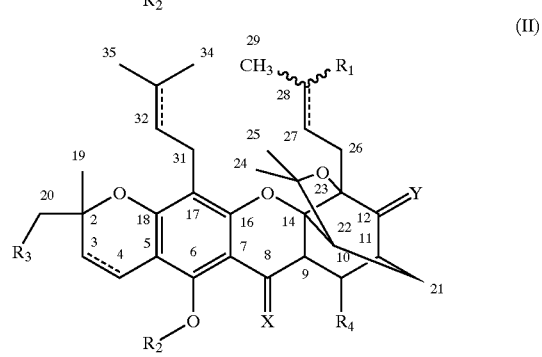

(II)

or a pharmacuetically acceptable salt or prodrug thereof, wherein:

the dotted lines are single bonds or epoxy groups;

X together with the attache carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

$R_1$ is formyl, methylenehydroxy, carboxy, acyl ($R_aCO$), optionally substituted alkoxycarbonyl ($R_aOCO$), optionally substituted alkylthiocarbonyl, optionally substituted aminocarbonyl (carbamyl, $R_bR_cNCO$) or hydroxyaminocarbonyl, where $R_a$ is optionally substituted lower alkyl; $R_b$ and $R_c$ are independently hydrogen, optionally substituted heteroalkyl, optionally substituted lower alkyl, optionally substituted aryl, optionally substituted heteroaryl or optionally substituted lower aralkyl groups; or $R_b$ and $R_c$ may be taken together with the attached N to form an optionally substituted, saturated or partially saturated 5–7 membered heterocyclo group;

$R_2$ is hydrogen, optionally substituted alkyl, acyl ($R_aCO$), carbamyl ($R_bR_aNCO$) or sulfonyl ($R_dSO_2$), where $R_a$, $R_b$ and $R_c$ are defined above; $R_d$ is hydrogen, optionally substituted lower alkyl, optionally substituted aryl, or optionally substituted lower aralkyl groups;

$R_3$ is prenyl; and $R_4$ is hydrogen, halogen, hydroxy, optionally substituted alkyl, cycloalkyl, alkoxy, alkylthio or amino;

with the proviso that said compound is not gambogic acid, isogambogic acid, morellinol, isomorellinol or gambogin.

9. The method of claim 8, wherein in the compound the dotted lines between C-9 and C-10 of a compound of Formula I or III represent a double bond, $R_4$ is not a cycloalkyl group, the other dotted lines are not epoxy groups, and $R_b$ and $R_c$ are not heteroalkyl groups.

10. The method according to claim 8, wherein the method is for treating Hodgkin's disease, non-Hodgkin's lymphomas, acute and chronic lymphocytic leukemias, multiple myeloma, neuroblastoma, breast carcinomas, ovarian carcinomas, lung carcinomas, Wilms'tumor, cervical carcinomas, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, or prostatic carcinomas.

11. A method for the treatment of drug resistant cancer, comprising administering to an animal in need of such treatment an effective amount of a compound having one of the Formulae I–III:

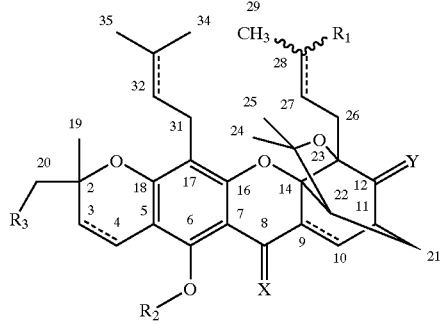

(I)

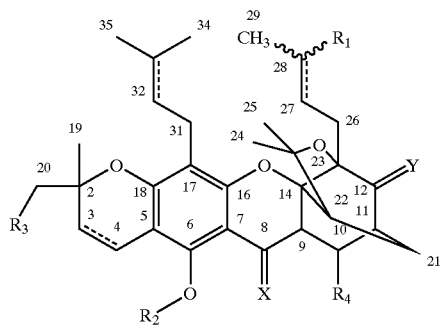

(II)

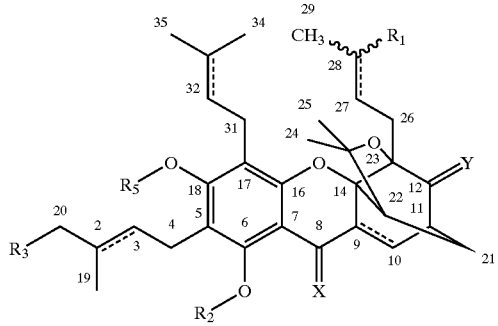

(III)

or a pharmaceutically acceptable salt or prodrug thereof, wherein:
the dotted lines are single bonds, double bonds or epoxy groups;
X together with the attached carbon is a methylene, carbonyl, hydroxymethinyl, alkoxymethinyl, aminomethinyl, an oxime, a hydrazone, an arylhydrazone or semicarbazone;
Y together with the attached carbon is a methylene, carbonyl, hydroxymethinyl, alkoxymethinyl, aminomethinyl, an oxime, a hydrazone, an arylhydrazone or semicarbazone;
$R_1$ is formyl, methylenehydroxy, carboxy, acyl ($R_aCO$), optionally substituted alkoxycarbonyl ($R_aOCO$), optionally substituted alkylthiocarbonyl, optionally substituted aminocarbonyl (carbamyl, $R_bR_cNCO$) or hydroxyaminocarbonyl, where $R_a$ is optionally substituted lower alkyl; $R_b$ and $R_c$ are independently hydrogen, optionally substituted heteroalkyl, optionally substituted lower alkyl, optionally substituted aryl, optionally substituted heteroaryl or optionally substituted lower aralkyl groups; or $R_b$ and $R_c$ may be taken together with the attached N to form an optionally substituted, saturated or partially saturated 5–7 membered heterocyclo group;
$R_2$ is hydrogen, optionally substituted alkyl, acyl ($R_aCO$), carbamyl ($R_bR_cNCO$) or sulfonyl ($R_dSO_2$), where $R_a$, $R_b$ and $R_c$ are defined above; $R_d$ is hydrogen, optionally substituted lower alkyl, optionally substituted aryl, or optionally substituted lower aralkyl groups;
$R_3$ is hydrogen or prenyl;
$R_4$ is hydrogen, halogen, hydroxy, optionally substituted alkyl, cycloalkyl, alkoxy, alkylthio or amino; and
$R_5$ is hydrogen, optionally substituted alkyl, acyl ($R_aCO$), carbamyl ($R_bR_cNCO$) or sulfonyl ($R_dSO_2$), where $R_a$, $R_b$, $R_c$ and $R_d$ are defined above;
with the proviso that said compound is not gambogic acid, isogambogic acid, morellinol, or isomorellinol.

12. The method of claim 11, wherein in the compound the dotted lines between C-9 and C-10 of a compound of Formula I or III represent a double bond, $R_4$ is not a cycloalkyl group, the other dotted lines are not epoxy groups, and $R_b$ and $R_c$ are not heteroalkyl groups.

13. The method according to claim 8 or 11, wherein said compound is administered together with at least one known cancer chemotherapeutic agent, or a pharmaceutically acceptable salt of said agent.

14. The method according to claim 13, wherein said known cancer chemotherapeutic agent is selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Herceptin® (trastuzumab), Rituxan® (rituximab) and alanosine.

15. The method according to claim 8 or 11, wherein said animal is also treated with radiation-therapy.

16. The method according to claim 8 or 11, wherein said compound(s) are administered after surgical treatment for cancer.

17. The method according to claim 1, wherein the mammal has an autoimmune disease.

18. The method according to claim 1, wherein the mammal has rheumatoid arthritis.

19. The method according to claim 1, wherein the mammal has inflammation or inflammatory bowel disease.

20. The method according to claim 1, wherein the mammal has a skin disease.

21. The method according to claim 20, wherein said skin disease is psoriasis.

22. A compound having the Formula I:

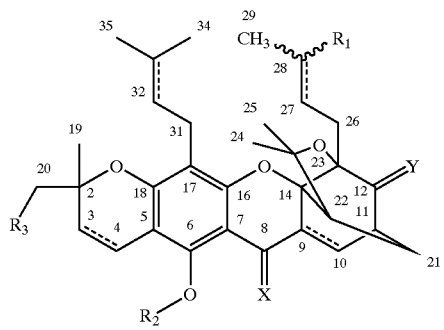

(I)

or a pharmaceutically acceptable salt or prodrug thereof, wherein:

the dotted lines are single bonds, double bonds or epoxy groups;

X together with the attached carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

$R_1$ is formyl, methylenehydroxy, carboxy, acyl ($R_aCO$), optionally substituted alkoxycarbonyl ($R_aOCO$), optionally substituted alkylthiocarbonyl, optionally substituted aminocarbonyl (carbamyl, $R_bR_cNCO$) or hydroxyaminocarbonyl, where $R_a$ is optionally substituted lower alkyl; $R_b$ and $R_c$ are independently hydrogen, optionally substituted heteroalkyl, optionally substituted lower alkyl, optionally substituted aryl, optionally substituted heteroaryl or optionally substituted lower aralkyl groups; or $R_b$ and $R_c$ may be taken together with the attached N to form an optionally substituted, saturated or partially saturated 5–7 membered heterocyclo group;

$R_2$ is hydrogen, optionally substituted alkyl, acyl ($R_aCO$), carbamyl ($R_bR_cNCO$) or sulfonyl ($R_dSO_2$), where $R_a$, $R_b$ and $R_c$ are defined above; $R_d$ is hydrogen, optionally substituted lower alkyl, optionally substituted aryl, or optionally substituted lower aralkyl groups; and $R_3$ is prenyl;

with the proviso that if $R_1$ is methyl, carboxy or methoxycarbonyl, and X and Y are O, then $R_2$ is not a hydrogen, acetyl or methyl.

23. A compound of claim 22, wherein the dotted lines between C-9 and C-10 represent a double bond, the other dotted lines are not epoxy groups, and $R_b$ and $R_a$ are not heteroalkyl groups.

24. A compound according to claim 22, wherein $R_1$ is formyl, acetyl, propionyl, carboxy, methoxycarbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N'-piperazinylcarbonyl, 2-(dimethylamino)-ethylcarbamyl or N-morpholinylcarbonyl, and the dotted lines represent double bonds.

25. A compound according to claim 22, wherein $R_2$ is hydrogen, formyl, acetyl, dimethylcarbamyl, diethylcarbamyl, 2-(dimethylamino)ethylcarbamyl, N-piperidinylcarbonyl, N-methyl-N'-piperazinylcarbonyl, N-morpholinylcarbonyl, methylsulfonyl, ethylsulfonyl, phenylsulfonyl, methyl, ethyl, 2-piperidinylethyl, 2-morpholinylethyl, 2-(dimethylamino)ethyl, or 2-(diethylamino)ethyl, and the dotted lines represent double bonds.

26. A compound having the Formula II:

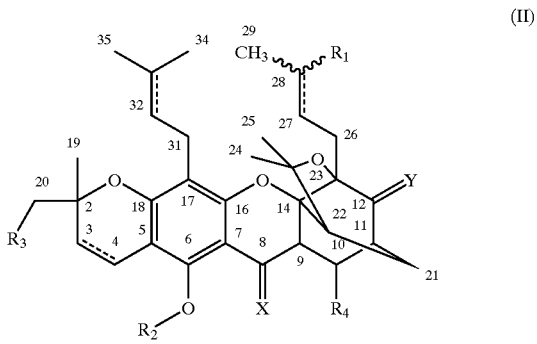

(II)

or a pharmaceutically acceptable salt or prodrug thereof, wherein:

the dotted lines are single bonds, double bonds or epoxy groups;

X together with the attached carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

$R_1$ is formyl, methylenehydroxy, carboxy, acyl ($R_aCO$), optionally substituted alkoxycarbonyl ($R_aOCO$), optionally substituted alkylthiocarbonyl, optionally substituted aminocarbonyl (carbamyl, $R_bR_cNCO$) or hydroxyaminocarbonyl, where $R_a$ is optionally substituted lower alkyl; $R_b$ and $R_c$ are independently hydrogen, optionally substituted heteroalkyl, optionally substituted lower alkyl, optionally substituted aryl, optionally substituted heteroaryl or optionally substituted lower aralkyl groups; or $R_b$ and $R_c$ may be taken together with the attached N to form an optionally substituted, saturated or partially saturated 5–7 membered heterocyclo group;

$R_2$ is hydrogen, optionally substituted alkyl, acyl ($R_a$CO), carbamyl ($R_bR_c$NCO) or sulfonyl ($R_d$SO$_2$), where $R_a$, $R_b$ and $R_c$ are defined above; $R_d$ is hydrogen, optionally substituted lower alkyl, optionally substituted aryl, or optionally substituted lower aralkyl groups;

$R_3$ is hydrogen or prenyl; and $R_4$ is hydrogen, halogen, hydroxy, optionally substituted alkyl, cycloalkyl, alkoxy, alkylthio or amino;

with the proviso that if $R_1$ is formyl or carboxy, $R_2$ is hydrogen, $R_3$ is hydrogen, and X and Y are O, then $R_4$ is not a hydrogen, hydroxy, methoxy or ethoxy.

27. A compound of claim 26, wherein $R_4$ is not a cycloalkyl group, the dotted lines are not epoxy groups, and $R_b$ and $R_c$ are not heteroalkyl groups.

28. A compound according to claim 26, wherein $R_1$ is formyl, acetyl, propionyl, carboxy, methoxycarbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N'-piperazinylcarbonyl, 2-(dimethylamino)-ethylcarbamyl or N-morpholinylcarbonyl, and the dotted lines represent double bonds.

29. A compound according to claim 26, wherein $R_2$ is hydrogen, formyl, acetyl, dimethylcarbamyl, diethylcarbamyl, 2-(dimethylamino)ethylcarbamyl, N-piperidinylcarbonyl, N-methyl-N'-piperazinylcarbonyl, N-morpholinylcarbonyl, methylsulfonyl, ethylsulfonyl, phenylsulfonyl, methyl, ethyl, 2-piperidinylethyl, 2-morpholinylethyl, 2-(dimethylamino)ethyl, or 2-(diethylamino)ethyl, and the dotted lines represent double bonds.

30. A compound according to claim 26, wherein $R_4$ is methyl, ethyl, phenyl, chloro, bromo, hydroxy, hydrogen, methoxy, ethoxy, methylthio, ethylthio, butylthio, dimethylamino, diethylamino, piperidinyl, pyrrolidinyl, imidazolyl, pyrazolyl, N-methylpiperazinyl, 2-(dimethylamino)ethylamino or morpholinyl, and the dotted lines represent double bonds.

31. A compound according to claim 22, wherein said compound is selected from the group consisting of:

Gambogyl dimethylamine;
Gambogyl amine;
Gambogyl diethylamine;
Gambogyl hydroxyamine;
Gambogyl piperidine;
6-Methoxy-gambogic acid;
6-(2-Dimethylaminoethoxy)-gambogic acid;
6-(2-Piperidinylethoxy)-gambogic acid;
6-(2-Morpholinylethoxy)-gambogic acid;
6-Methoxy-gambogyl piperidine;
Gambogyl morpholine;
Gambogyl (2-dimethylaminoethylamine);
Gambogyl (4-methylpiperazine);
N-(2-Gambogylamido-ethyl)biotinamide;
Gambogyl (2-(4-morpholinyl)ethylamine);
Gambogyl (4-(2-pyridyl)piperazine);
6-Acetylgambogic acid;
N-Hydroxysuccinimidyl gambogate;
8-(Gambogylamido)octanoic acid;
6-(Gambogylamido)hexanoic acid;
12-(Gambogylamido)dodecanoic acid;
N-Hydroxysuccinimidyl-8-(gambogylamido)octanoate;
N-Hydroxysuccinimidyl-6-(gambogylamido)hexanoate;
N-Hydroxysuccinimidyl-12-(gambogylamido)dodecanoate;
Gambogyl (4-(2-pyrimidyl)piperazine);
Gambogyl (bis(2-pyridylmethyl)amine);
Gambogyl (N-(3-pyridyl)-N-(2-hydroxybenzyl)amine);
Gambogyl (4-benzylpiperazine);
Gambogyl (4-(3,4-methylenedioxybenzyl)piperazine);
Gambogyl (N-methyl-5-(methylamino)-3-oxapentylamine);
Gambogyl (N-methyl-8-(methylamino)-3,6-dioxaoctylarnine);
Gambogyl (N-ethyl-2-(ethylamino)ethylamine);
Gambogyl (4-isopropylpiperazine);
Gambogyl (4-cyclopentylpiperazine);
Gambogyl (N-(2-oxo-2-ethoxyethyl)-(2-pyridyl)methylamine);
Gambogyl (2,5-dimethylpiperazine);
Gambogyl (3,5-dimethylpiperazine);
Gambogyl (4-(4-acetylphenyl)piperazine);
Gambogyl (4-ethoxycarbonylpiperazine);
Gambogyl (4-(2-oxo-2-pyrrolidylethyl)piperazine);
Gambogyl (4-(2-hydroxyethyl)piperazine);
Gambogyl (N-methyl-2-(methylamino)ethylamine);
Gambogyl (N-methyl-2-(benzylamino)ethylamine);
Gambogyl (N-methyl-(6-methyl-2-pyridyl)methylamine);
Gambogyl (N-methy-2-(2-pyridyl)ethylamine);
Gambogyl (N-methyl-(2-pyridyl)methylamine);
Gambogyl (N-methyl-4-(3-pyridyl)butylamine);
Gambogyl (bis(3-pyridylmethyl)amine);
Gambogyl (2,4-dimethyl-2-imidazoline);
Gambogyl (4-methyl-homopiperazine);
Gambogyl (4-(5-hydroxy-3-oxapentyl)piperazine);
Gambogyl (3-dimethylaminopyrrolidine);
Gambogyl ((2-furanyl)methylamine);
Gambogyl (2-hydroxy-1-methyl-2-phenylethylamine);
Gambogyl (3,4,5-trimethoxybenzylamine);
Gambogyl (2-(2-methoxyphenyl)ethylamine);
Gambogyl (2-methoxybenzylamine);
Gambogyl (3,4-methylenedioxybenzylamine);
Gambogyl (2-(2,5-dimethoxyphenyl)ethylamine);
Gambogyl (2-(3-methoxyphenyl)ethylamine);
Gambogyl (3-(piperidinyl)propylamine);
Gambogyl (2-(piperidinyl)ethylamine);
Gambogyl (3,4-dimethoxybenzylamine);
Gambogyl ((2-tetrahydrofuranyl)methylamine);
Gambogyl ((N-ethyl-2-pyrrolidinyl)methylamine);
Gambogyl (2-diethylaminoethylamine);
Gambogyl (2,2-dimethyl-3-dimethylaminopropylamine);
Gambogyl ((N-ethoxycarbonyl-4-piperidinyl)amine);
Gambogyl (2-carbamylpyrrolidine);
Gambogyl (3-(homopiperidinyl)propylamine);

Gambogyl ((N-benzyl-4-piperidinyl)amine);
Gambogyl (2-(4-methoxyphenyl)ethylamine);
Gambogyl (4-oxa-hex-5-enylamine);
Ganbogyl (6-hydroxyhexylamine);
Gambogyl (2-(3,5-dimethoxyphenyl)ethylamine);
Gambogyl (3,5-dimethoxybenzylamine); and
Gambogyl (2-carbamyl-2-(4-hydroxyphenyl)ethylamine).

32. A compound according to claim 26, wherein said compound is selected from the group consisting of:
9,10-Dihydrogambogyl (4-methylpiperazine);
9,10-Dihydrogambogyl (dimethylamino)ethylamine;
9,10-Dihydro-1 2-hydroxygambogic acid;
9,10-Dihydro-10-(4-methylpiperazinyl)-gambogyl piperidine;
9,10-Dihydro-10-(4-methylpiperazinyl)-gambogyl morpholine;
9,10-Dihydro-10-piperidinyl-gambogyl piperidine;
9,10-Dihydro-10-(4-methylpiperazinyl)-gambogyl (4-methylpiperazine);
9,10-Dihydro-10-(4-methylpiperazinyl)-gambogic acid;
9,10-Dihydro-10-pyrrolidinyl-gambogic acid;
Methyl-9,10-dihydro-10-morpholinyl-gambogate;
9,10-Dihydro-10-morpholinyl-gambogyl morpholine;
9,10-Dihydro-10-morpholinyl-gambogyl piperidine;
9,10-Dihydro-10-methoxy-gambogic acid;
10-Butylthio-9,10-dihydrogambogic acid;
9,10-Dihydro-10-piperidinyl-gambogic acid;
9,10-Dihydro-10-morpholinyl-gambogic acid;
10-Cyclohexyl-9,10-dihydro-gambogic acid;
9,10-Dihydro-10-methyl-gambogic acid;
9,10-Dihydro-10-methoxy-gambogyl piperidine;
9,10-Dihydro-10-(4-(2-pyridyl)piperazinyl)gambogyl (4-(2-pyridyl)piperazine);
9,10-Dihydro-10-(4-(2-pyridyl)piperazinyl)gambogic acid; and
9,10-Epoxygambogic acid.

33. A pharmaceutical composition, comprising a compound of claim 22 or 26, and a pharmaceutically acceptable carrier.

34. The pharmaceutical composition of claim 33, further comprising at least one known cancer chemotherapeutic agent, or a pharmaceutically acceptable salt of said agent.

35. The pharmaceutical composition of claim 34, wherein said known cancer chemotherapeutic agent is selected from the group consisting of busulfan, cis-platin, mitomycin C, carboplatin, colchicine, vinblastine, paclitaxel, docetaxel, caiptothecin, topotecan, doxorubicin, etoposide, 5-azacytidine, 5-fluorouracil, methotrexate, 5-fluoro-2'-deoxy-uridine, ara-C, hydroxyurea, thioguanine, meiphalan, chorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Herceptin® (trastuzumab), Rituxan® (rituximab) and alanosine.

36. The method of claim 1, wherein said compound is of Formula I.

37. The method of claim 36, wherein $R_3$ is prenyl.

38. The method of claim 1, wherein said compound is of Formula II.

39. The method of claim 38, wherein $R_3$ is prenyl.

40. The method of claim 1, wherein said compound is of Formula III.

41. The method of claim 40, wherein $R_3$ is prenyl.

42. The method of claim 1, with the further proviso that said disorder is other than cancer, (a) said compound is not gambogic acid, isogambogic acid, morellinol, isomorellinol or gambogin, (b) the compound is of Formula I or II, and (c) $R_3$ is prenyl.

43. The method of claim 1, wherein said disorder is other than cancer.

44. The method of claim 8, wherein said compound is of Formula I.

45. The method of claim 8, wherein said compound is of Formula II.

46. The method of claim 11, wherein said compound is of Formula I.

47. The method of claim 11, wherein said compound is of Formula II.

48. The method of claim 11, wherein (a) said compound is of Formula I or II, and (b) $R_3$ is prenyl.

49. The compound of claim 26, wherein $R_3$ is prenyl.

50. The compound of claim 26, wherein Y is O.

51. A method of inducing cell apoptosis in a mammal in need thereof, comprising administering to said mammal an effective amount of a compound having the Formula I:

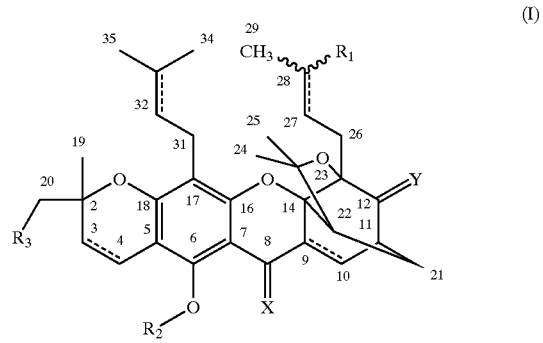

(I)

or a pharmaceutically acceptable salt or prodrug thereof, wherein:
the dotted lines are single bonds, double bonds or epoxy groups;
X together with the attached carbon is a methylene, carbonyl, hydroxymethinyl, alkoxymethinyl, aminomethinyl, an oxime, a hydrazone, an arylhydrazone or semicarbazone;
Y together with the attached carbon is a methylene, carbonyl, hydroxymethinyl, alkoxymethinyl, aminomethinyl, an oxime, a hydrazone, an arylhydrazone or semicarbazone;
$R_1$ is optionally substituted alkylthiocarbonyl, optionally substituted aminocarbonyl (carbamyl, $R_bR_cNCO$) or hydroxyaminocarbonyl, where $R_b$ and $R_c$ are independently hydrogen, optionally substituted heteroalkyl, optionally substituted aryl, optionally substituted heteroaryl or optionally substituted lower aralkyl groups; or $R_b$ and $R_c$ may be taken together with the attached N to form an optionally substituted, saturated or partially saturated 5–7 membered heterocyclo group; and when at least one of X and Y together with the attached carbon is a methylene, hydroxymethinyl, alkoxymethinyl, aminomethinyl, an oxime, a hydrazone, an arylhydrazone or semicarbazone; then $R_1$ is additionally optionally substituted lower alkyl, formyl, methylenehydroxy, carboxy, acyl ($R_aCO$), or optionally substituted alkoxycarbonyl ($R_aOCO$), where $R_a$ is optionally substituted lower alkyl;

R$_2$ is hydrogen, optionally substituted alkyl, acyl (R$_a$CO), carbamyl (R$_b$R$_c$NCO) or sulfonyl (R$_d$SO$_2$), where R$_a$, R$_b$, and R$_c$ are defined above; R$_d$ is hydrogen, optionally substituted lower alkyl, optionally substituted aryl, or optionally substituted lower aralkyl groups; and R$_3$ is hydrogen or prenyl.

52. A method of inducing cell apoptosis in a mammal in need thereof, comprising administering to said mammal an effective amount of a compound having the Formula II:

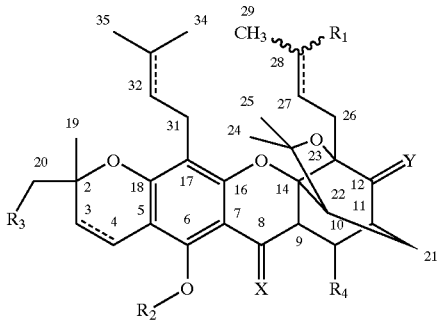

(II)

or a pharmaceutically acceptable salt or prodrug thereof, wherein:

the dotted lines are single bonds, double bonds or epoxy groups;

X together with the attached carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

R$_1$ is optionally substituted alkylthiocarbonyl, optionally substituted aminocarbonyl (carbamyl, R$_b$R$_c$NCO) or hydroxyaminocarbonyl, where R$_b$ and R$_c$ are independently hydrogen, optionally substituted heteroalkyl, optionally substituted lower alkyl, optionally substituted aryl, optionally substituted heteroaryl or optionally substituted lower aralkyl groups; or R$_b$ and R$_c$ may be taken together with the attached N to form an optionally substituted, saturated or partially saturated 5–7 membered heterocyclo group; R$_2$ is hydrogen, optionally substituted alkyl, acyl (R$_a$CO), carbamyl (R$_b$R$_c$NCO) or sulfonyl (R$_d$SO$_2$), where R$_a$, R$_b$, and R$_c$ are defined above; R$_d$ is hydrogen, optionally substituted lower alkyl, optionally substituted aryl, or optionally substituted lower aralkyl groups;

R$_3$ is hydrogen or prenyl; and

R$_4$ is hydrogen, halogen, hydroxy, optionally substituted alkyl, cycloalkyl, alkoxy, alkylthio or amino.

53. A method of inducing cell apoptosis in a mammal in need thereof comprising administering to said mammal an effective amount of a compound having the Formula II:

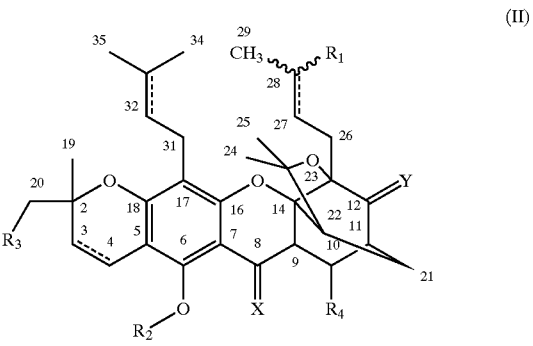

(II)

or a pharmaceutically acceptable salt or prodrug thereof, wherein:

the dotted lines are single bonds, double bonds or epoxy groups;

X together with the attached carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

R$_1$ is optionally substituted alkylthiocarbonyl, optionally substituted aminocarbonyl (carbamyl, R$_b$R$_c$NCO) or hydroxyaminocarbonyl, where R$_b$ and R$_c$ are independently hydrogen, optionally substituted heteroalkyl, optionally substituted lower alkyl, optionally substituted aryl, optionally substituted heteroaryl or optionally substituted lower aralkyl groups; or R$_b$ and R$_c$ may be taken together with the attached N to form an optionally substituted, saturated or partially saturated 5–7 membered heterocyclo group;

R$_2$ is hydrogen, optionally substituted alkyl, acyl (R$_a$CO), carbamyl (R$_b$R$_c$NCO) or sulfonyl (R$_d$SO$_2$), where R$_a$, R$_b$, and R$_c$ are defined above; R$_d$ is hydrogen, optionally substituted lower alkyl, optionally substituted aryl, or optionally substituted lower aralkyl groups;

R$_3$ is hydrogen or prenyl;

R$_4$ is hydrogen, halogen, hydroxy, optionally substituted alkyl, cycloalkyl, alkoxy, alkylthio or amino;

and when R$_4$ is halogen, cycloalkyl, alkylthio or amino, then R$_1$ additionally is optionally substituted lower alkyl, formyl, methylenehydroxy, carboxy, acyl (R$_a$CO), or optionally substituted alkoxycarbonyl (R$_a$OCO), where R$_a$ is optionally substituted lower alkyl.

54. The method of any one of claims 51–53, wherein said disorder is cancer.

* * * * *